US012583930B2

(12) United States Patent
Izquierdo et al.

(10) Patent No.: US 12,583,930 B2
(45) Date of Patent: Mar. 24, 2026

(54) HUMAN GLUCOSE-DEPENDENT INSULINOTROPIC POLYPEPTIDE RECEPTOR (GIPR) ANTIBODIES AND METHODS OF USE THEREOF TO INHIBIT GIP RECEPTOR AND SIGNALING

(71) Applicant: CRYSTAL BIOSCIENCE INC., Emeryville, CA (US)

(72) Inventors: Shelley Izquierdo, Berkeley, CA (US); Shreya Pramanick, Emeryville, CA (US); William Don Harriman, Alameda, CA (US)

(73) Assignee: CRYSTAL BIOSCIENCE INC., Emeryville, CA (US)

( * ) Notice: Subject to any disclaimer, the term of this patent is extended or adjusted under 35 U.S.C. 154(b) by 806 days.

(21) Appl. No.: 17/908,870

(22) PCT Filed: Feb. 22, 2021

(86) PCT No.: PCT/US2021/019096
§ 371 (c)(1),
(2) Date: Sep. 1, 2022

(87) PCT Pub. No.: WO2021/202013
PCT Pub. Date: Oct. 7, 2021

(65) Prior Publication Data
US 2024/0294654 A1      Sep. 5, 2024

Related U.S. Application Data

(60) Provisional application No. 63/001,857, filed on Mar. 30, 2020.

(51) Int. Cl.
*C07K 16/28*          (2006.01)
(52) U.S. Cl.
CPC ...... *C07K 16/2869* (2013.01); *C07K 2317/23* (2013.01); *C07K 2317/33* (2013.01); *C07K 2317/622* (2013.01); *C07K 2317/76* (2013.01); *C07K 2317/92* (2013.01)
(58) Field of Classification Search
CPC ........... C07K 16/2869; C07K 2317/23; C07K 2317/33; C07K 2317/622; C07K 2317/76; C07K 2317/92; C07K 2317/10; C07K 2317/565; A61P 3/10
See application file for complete search history.

(56) References Cited

U.S. PATENT DOCUMENTS

| | | |
|---|---|---|
| 2005/0048628 A1 | 3/2005 | Frank et al. |
| 2017/0066836 A1 | 3/2017 | Naka et al. |
| 2019/0144538 A1 | 5/2019 | Colussi et al. |
| 2019/0233543 A1 | 8/2019 | Agrawal et al. |
| 2019/0263931 A1 | 8/2019 | Rothstein et al. |
| 2019/0276546 A1 | 9/2019 | Me et al. |

FOREIGN PATENT DOCUMENTS

| | | |
|---|---|---|
| WO | WO 2017/189964 A2 | 11/2017 |
| WO | WO 2018/237097 A1 | 12/2018 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig. M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi: 10.1016/S0006-291X(03)01131-8).*
Chen et al. (1995) Embo J., 14(12):2784-2794. (doi: 10.1002/j.1460-2075.1995.tb07278.x).*
Min et al., "Molecular mechanism of an antagonistic antibody against glucose-dependent insulinotropic polypeptide receptor", MABS, Jan. 2020, 12(1): e1710047, 12 pages.
Ravn et al., "Structural and Pharmacological Characterization of Novel Potent and Selective Monoclonal Antibody Antagonists of Glucose-dependent Insulinotropic Polypeptide Receptor", The Journal of Biological Chemistry, 2013, 288(27): 19760-19772.

* cited by examiner

*Primary Examiner* — Robert S Landsman
(74) *Attorney, Agent, or Firm* — James S. Keddie; Bozicevic, Field & Francis LLP

(57)          ABSTRACT
The present disclosure provides antibodies that specifically bind to and in some cases inhibit the human glucose-dependent insulinotropic polypeptide (GIP) receptor. The antibodies find use in a variety of treatment, diagnostic, and monitoring applications, which are also described. For example, the antibodies may be used to treat a metabolic disorder, such as a disorder of glucose metabolism. In some embodiments, the antibody may have CDRs that are selected from any of the antibodies set forth in FIG. 9 or 10.

16 Claims, 15 Drawing Sheets
Specification includes a Sequence Listing.

| | # | mAb2/mAb1 | 1 11270p10.B2 | 2 11270p10.C4 | 3 11270p7.F3 | 4 11270p9.F7 | 5 11270p10.G4 | 6 11270p10.E6 | 7 11270p3.A10 | 8 11270p4.A12 | 9 11270p1.C8 | 10 11270p2.A4 | 11 11270p2.A8 | 12 11270p2.B7 |
|---|---|---|---|---|---|---|---|---|---|---|---|---|---|---|
| Chicken derived Abs | 1 | 11270p10.B2 | 56 | 49 | 29 | 18 | 57 | 72 | 267 | 113 | 170 | 36 | 57 | 51 |
| | 2 | 11270p10.C4 | 68 | 45 | 34 | 22 | 66 | 79 | 239 | 44 | 319 | 60 | 51 | 44 |
| | 3 | 11270p7.F3 | 73 | 46 | 23 | 21 | 71 | 66 | 286 | 86 | 229 | 44 | 43 | 43 |
| | 4 | 11270p9.F7 | 86 | 43 | 25 | 34 | 86 | 89 | 104 | 151 | 221 | 107 | 105 | 91 |
| | 5 | 11270p10.G4 | 29 | 17 | 13 | 7 | 28 | 26 | 148 | 116 | 131 | 94 | 127 | 129 |
| | 6 | 11270p10.E6 | 28 | 17 | 17 | 7 | 27 | 29 | 140 | 131 | 154 | 106 | 147 | 121 |
| | 7 | 11270p3.A10 | 99 | 114 | 99 | 61 | 115 | 105 | 25 | 24 | 65 | 23 | 16 | 11 |
| | 8 | 11270p4.A12 | 178 | 90 | 93 | 90 | 139 | 134 | 33 | 33 | 61 | 25 | 20 | 18 |
| | 9 | 11270p1.C8 | 173 | 57 | 67 | 101 | 179 | 171 | 26 | 19 | 76 | 12 | 9 | 10 |
| | 10 | 11270p2.A4 | 175 | 105 | 130 | 120 | 187 | 187 | 34 | 39 | 83 | 19 | 18 | 17 |
| | 11 | 11270p2.A8 | 174 | 113 | 114 | 108 | 182 | 182 | 22 | 38 | 105 | 22 | 14 | 21 |
| | 12 | 11270p2.B7 | 207 | 98 | 89 | 155 | 224 | 214 | 70 | 61 | 159 | 25 | 39 | 22 |
| | 13 | 11270p1.D1 | 200 | 74 | 83 | 142 | 225 | 194 | 75 | 44 | 136 | 24 | 16 | 15 |
| | 14 | 11270p3.C8 | 101 | 113 | 111 | 66 | 104 | 98 | 118 | 72 | 94 | 78 | 33 | 17 |
| | 15 | 11270p3.E9 | 97 | 112 | 138 | 71 | 98 | 100 | 87 | 79 | 64 | 56 | 37 | 17 |
| | 16 | 11270p2.G3 | 114 | 168 | 130 | 89 | 114 | 109 | 63 | 76 | 125 | 74 | 49 | 22 |
| | 17 | 11270p2.F8 | 105 | 176 | 104 | 70 | 104 | 100 | 101 | 44 | 72 | 40 | 22 | 18 |
| | 18 | 11270p4.E10 | 108 | 101 | 117 | 56 | 113 | 106 | 54 | 54 | 54 | 24 | 32 | 30 |
| | 19 | 11272p2.2.E11 | 111 | 92 | 183 | 45 | 106 | 90 | 13 | 65 | 22 | 50 | 77 | 64 |
| | 20 | 11272p1.H8 | 135 | 78 | 197 | 47 | 103 | 95 | 12 | 83 | 39 | 70 | 97 | 129 |
| | 21 | 11318p5.A4 | 130 | 86 | 168 | 67 | 129 | 124 | 44 | 85 | 60 | 80 | 99 | 92 |
| | 22 | 11272p1.E6 | 105 | 126 | 258 | 48 | 74 | 75 | 49 | 80 | 71 | 88 | 113 | 51 |
| | 23 | 11272p1.F7 | 93 | 138 | 201 | 47 | 96 | 89 | 39 | 86 | 66 | 72 | 85 | 37 |
| | 24 | 11272p1.C8 | 130 | 99 | 232 | 107 | 136 | 115 | 26 | 77 | 59 | 92 | 110 | 57 |
| | 25 | 11272p3.F12 | 103 | 127 | 151 | 78 | 97 | 93 | 41 | 60 | 61 | 72 | 81 | 27 |
| | 26 | 11272p3.E8 | 120 | 187 | 203 | 97 | 119 | 110 | 26 | 56 | 65 | 56 | 78 | 24 |
| | 27 | 11272p1.D6 | 97 | 146 | 244 | 60 | 88 | 89 | 50 | 64 | 37 | 120 | 53 | 38 |
| | 28 | 11272p1.A10 | 121 | 132 | 383 | 79 | 115 | 126 | 29 | 158 | 51 | 109 | 142 | 106 |
| | 29 | 11271p4.B4 | 148 | 131 | 412 | 109 | 156 | 143 | 49 | 244 | 92 | 168 | 204 | 130 |
| | 30 | 11271p2.D8 | 126 | 148 | 289 | 91 | 116 | 116 | 69 | 189 | 165 | 146 | 192 | 110 |
| | 31 | 11272p8.E10 | 107 | 72 | 185 | 85 | 111 | 103 | 43 | 83 | 82 | 122 | 126 | 37 |
| | 32 | 11272p3.E7 | 109 | 116 | 221 | 68 | 99 | 101 | 19 | 65 | 22 | 30 | 60 | 66 |
| | 33 | 11271p3.D12 | 154 | 200 | 367 | 121 | 143 | 140 | 14 | 154 | 36 | 118 | 153 | 175 |
| | 34 | 11271p1.D1 | 119 | 121 | 400 | 75 | 113 | 101 | 18 | 114 | 71 | 150 | 165 | 251 |
| | 35 | 11271p1.C9 | 115 | 133 | 437 | 78 | 118 | 111 | 24 | 189 | 87 | 116 | 130 | 326 |
| | 36 | 11271p2.A8 | 110 | 109 | 286 | 89 | 106 | 111 | 9 | 115 | 40 | 73 | 96 | 196 |
| | 37 | 11271p2.B3 | 193 | 118 | 542 | 104 | 136 | 130 | 3 | 229 | 90 | 122 | 184 | 482 |
| | 38 | 11272p2.2.C4 | 121 | 105 | 202 | 72 | 117 | 107 | 34 | 90 | 60 | 122 | 138 | 155 |
| | 39 | 11271p1.A5 | 91 | 162 | 285 | 50 | 86 | 74 | 36 | 77 | 12 | 91 | 61 | 96 |
| | 40 | 11270p10.B7 | 33 | 34 | 79 | 122 | 140 | 149 | 140 | 74 | 260 | 57 | 40 | 41 |
| Abs from other sources | 41 | Rodent_1 | 32 | 19 | 44 | 47 | 51 | 51 | 44 | 1 | 67 | 31 | 44 | 34 |
| | 42 | Gipg013 | 8 | 2 | 21 | 7 | 25 | 44 | 4 | -8 | 11 | -15 | -10 | 0 |
| | 43 | Rodent_2 | 11 | 6 | 13 | 4 | 27 | 29 | 1 | -4 | 13 | -17 | -12 | -4 |
| | 44 | Rodent_3 | 13 | 40 | 13 | -5 | 30 | 28 | -4 | -6 | -7 | -20 | 31 | -9 |
| | 45 | Rodent_4 | 9 | 35 | 5 | 15 | 83 | 35 | 0 | -6 | 25 | -19 | 113 | -21 |
| | | Pearson | 0.57 | 0.67 | 0.45 | 0.92 | 0.97 | -0.16 | 0.11 | 0.23 | 0.16 | 0.83 | 0.69 | |

FIG. 5

| chicken derived Abs | | | | | | | | | | | | | | | | | |
|---|---|---|---|---|---|---|---|---|---|---|---|---|---|---|---|---|---|
| 13 | 14 | 15 | 16 | 17 | 18 | 19 | 20 | 21 | 22 | 23 | 24 | 25 | 26 | 27 | 28 | 29 | 30 |
| 11270p1.D1 | 11270p3.C8 | 11270p3.E9 | 11270p2.G3 | 11270p2.F8 | 11270p4.E10 | 11272p2.2.E11 | 11272p1.H8 | 11318p5.A4 | 11272p1.E6 | 11272p1.F7 | 11272p1.C8 | 11272p3.F12 | 11272p3.E8 | 11272p1.D6 | 11272p1.A10 | 11271p4.B4 | 11271p2.D8 |
| 193 | 302 | 183 | 44 | 69 | 88 | 161 | 78 | 27 | 150 | 137 | 48 | 109 | 129 | 149 | 159 | 124 | 117 |
| 249 | 258 | 296 | 39 | 43 | 71 | 190 | 47 | 21 | 174 | 247 | 35 | 175 | 170 | 211 | 123 | 156 | 155 |
| 178 | 269 | 351 | 61 | 71 | 61 | 194 | 90 | 70 | 220 | 208 | 47 | 154 | 153 | 179 | 145 | 149 | 158 |
| 177 | 133 | 94 | 65 | 70 | 139 | 146 | 83 | 49 | 128 | 122 | 63 | 100 | 107 | 136 | 94 | 110 | 110 |
| 167 | 153 | 93 | 75 | 83 | 122 | 120 | 112 | 60 | 121 | 102 | 53 | 84 | 85 | 103 | 75 | 77 | 88 |
| 186 | 139 | 127 | 73 | 71 | 141 | 118 | 108 | 57 | 109 | 122 | 76 | 83 | 94 | 99 | 98 | 84 | 80 |
| 32 | 17 | 12 | 13 | 13 | 49 | 45 | 0 | -22 | 46 | 50 | 15 | 32 | 33 | 42 | 31 | 36 | 42 |
| 54 | 17 | 21 | 22 | 23 | 45 | 54 | 29 | -15 | 65 | 68 | 29 | 40 | 56 | 64 | 44 | 49 | 58 |
| 59 | 25 | 20 | 16 | 21 | 17 | 54 | 19 | -10 | 72 | 68 | 18 | 38 | 41 | 54 | 39 | 46 | 63 |
| 88 | 35 | 26 | 30 | 25 | 48 | 87 | 34 | 22 | 87 | 91 | 20 | 66 | 67 | 87 | 75 | 67 | 82 |
| 73 | 22 | 19 | 20 | 18 | 51 | 78 | 30 | 15 | 76 | 79 | 77 | 51 | 46 | 67 | 73 | 60 | 70 |
| 128 | 36 | 22 | 23 | 23 | 62 | 135 | 30 | 30 | 109 | 121 | 81 | 82 | 85 | 104 | 71 | 58 | 66 |
| 68 | 37 | 31 | 18 | 27 | 46 | 113 | 39 | -14 | 113 | 109 | 34 | 69 | 86 | 94 | 70 | 45 | 56 |
| 43 | 21 | 19 | 20 | 22 | 78 | 74 | 63 | -16 | 67 | 73 | 57 | 45 | 59 | 64 | 50 | 36 | 39 |
| 45 | 21 | 20 | 18 | 19 | 69 | 63 | 67 | -4 | 54 | 57 | 65 | 37 | 44 | 59 | 41 | 23 | 31 |
| 57 | 21 | 22 | 22 | 20 | 84 | 69 | 59 | 35 | 57 | 54 | 36 | 41 | 45 | 70 | 47 | 27 | 37 |
| 32 | 13 | 14 | 14 | 20 | 100 | 59 | 68 | 89 | 59 | 48 | 31 | 31 | 43 | 55 | 37 | 27 | 31 |
| 55 | 89 | 65 | 44 | 52 | 32 | 52 | 21 | -20 | 65 | 60 | 38 | 44 | 47 | 58 | 48 | 99 | 105 |
| 24 | 20 | 19 | 23 | 27 | 70 | 31 | 48 | -25 | 63 | 59 | 44 | 50 | 47 | 49 | 47 | 72 | 70 |
| 84 | 26 | 26 | 39 | 30 | 87 | 57 | 68 | -3 | 84 | 86 | 49 | 75 | 73 | 81 | 75 | 78 | 83 |
| 73 | 44 | 38 | 43 | 49 | 99 | 69 | 83 | 21 | 99 | 99 | 124 | 86 | 83 | 99 | 75 | 73 | 98 |
| 22 | 11 | 4 | 15 | 24 | 158 | 47 | 154 | 26 | 42 | 30 | 21 | 29 | 33 | 44 | 28 | 29 | 25 |
| 13 | 3 | 2 | 5 | 11 | 155 | 54 | 119 | -49 | 40 | 44 | 24 | 27 | 33 | 37 | 29 | 31 | 42 |
| 26 | 7 | 8 | 11 | 13 | 123 | 53 | 134 | 26 | 39 | 38 | 22 | 22 | 32 | 33 | 24 | 18 | 32 |
| 24 | 9 | 3 | 11 | 15 | 81 | 54 | 140 | 46 | 38 | 44 | 28 | 20 | 27 | 30 | 35 | 16 | 26 |
| 16 | 4 | 10 | 13 | 22 | 116 | 51 | 127 | 61 | 26 | 30 | 20 | 22 | 26 | 37 | 31 | 25 | 31 |
| 25 | 2 | -3 | 5 | 13 | 147 | 41 | 121 | 71 | 41 | 31 | 19 | 20 | 21 | 30 | 10 | 23 | 21 |
| 29 | 4 | 10 | 21 | 25 | 213 | 47 | 197 | 22 | 48 | 60 | 36 | 37 | 44 | 41 | 39 | 41 | 47 |
| 64 | 25 | 32 | 29 | 31 | 448 | 119 | 2888 | 35 | 86 | 85 | 112 | 74 | 81 | 74 | 69 | 38 | 42 |
| 33 | 42 | 39 | 27 | 37 | 293 | 94 | 270 | -33 | 75 | 70 | 55 | 52 | 62 | 63 | 70 | 26 | 36 |
| 15 | 11 | 8 | 7 | 15 | 159 | 77 | 125 | 33 | 62 | 58 | 33 | 43 | 52 | 55 | 46 | 21 | 26 |
| 30 | 10 | 7 | 23 | 30 | 72 | 31 | 35 | 11 | 44 | 51 | 24 | 47 | 36 | 36 | 25 | 56 | 49 |
| 103 | 59 | 31 | 32 | 34 | 163 | 54 | 65 | 18 | 110 | 96 | 56 | 65 | 70 | 106 | 144 | 107 | 91 |
| 156 | 25 | 29 | 31 | 34 | 142 | 61 | 81 | -31 | 65 | 66 | 24 | 76 | 52 | 59 | 65 | 128 | 117 |
| 176 | 55 | 66 | 32 | 39 | 187 | 33 | 63 | -30 | 55 | 39 | 20 | 44 | 43 | 43 | 32 | 132 | 129 |
| 144 | 45 | 48 | 35 | 29 | 101 | 33 | 45 | -44 | 32 | 38 | 16 | 31 | 28 | 36 | 28 | 99 | 85 |
| 379 | 28 | 54 | 26 | 21 | 164 | 51 | 109 | -25 | 52 | 64 | 14 | 47 | 58 | 51 | 53 | 162 | 150 |
| 70 | 38 | 54 | 37 | 36 | 68 | 67 | 48 | -24 | 123 | 123 | 46 | 93 | 84 | 122 | 88 | 101 | 96 |
| 34 | 13 | 25 | 18 | 28 | 129 | 17 | 41 | 72 | 106 | 69 | 41 | 34 | 29 | 90 | 76 | 84 | 69 |
| 142 | 113 | 90 | 34 | 30 | 119 | 139 | 49 | 13 | 134 | 125 | 59 | 123 | 116 | 125 | 140 | 110 | 95 |
| 55 | 35 | 23 | 39 | 18 | 12 | 33 | 18 | 20 | 14 | 21 | 5 | 43 | 23 | 5 | 21 | 7 | 21 |
| 6 | 2 | -10 | 1 | -12 | -10 | 0 | -2 | 1 | -3 | -1 | -5 | 0 | 3 | 3 | -4 | -7 | -10 |
| 1 | -3 | -13 | -2 | -9 | -5 | 6 | -4 | 2 | 1 | 7 | -11 | 5 | -1 | -10 | 4 | -2 | 1 |
| 4 | -1 | -11 | -8 | 28 | 29 | 1 | 0 | -9 | -4 | -1 | -8 | -3 | -2 | -8 | -5 | -11 | -7 |
| 4 | -4 | -23 | -18 | 50 | 35 | 16 | 10 | 7 | -4 | -4 | -10 | 14 | 12 | -10 | -11 | -8 | -16 |
| 0.68 | 0.64 | 0.93 | 0.64 | 0.78 | 0.16 | 0.21 | 0.25 | 0.20 | 0.29 | 0.95 | 0.54 | 0.54 | 0.97 | 0.96 | 0.91 | 0.73 | 0.98 |

FIG. 5 (Cont. 1)

| | | | | | | | | | | Abs from other sources | | | | | | |
|---|---|---|---|---|---|---|---|---|---|---|---|---|---|---|---|---|
| 31 | 32 | 33 | 34 | 35 | 36 | 37 | 38 | 39 | 40 | 41 | 42 | 43 | 44 | 45 | | |
| 11272p8.E10 | 11272p3.E7 | 11271p3.D12 | 11271p1.D1 | 11271p1.C9 | 11271p2.A8 | 11271p2.B3 | 11272p2.2.C4 | 11271p1.A5 | 11270p10.B7 | Rodent_1 | Gipg013 | Rodent_2 | Rodent_3 | Rodent_4 | Pearson | mAb2/mAb1 cluster |
| 191 | 152 | 260 | 312 | 282 | 156 | 142 | 154 | 186 | 98 | 284 | 333 | 330 | 332 | 310 | | A |
| 271 | 179 | 247 | 323 | 275 | 190 | 182 | 176 | 195 | 106 | 413 | 308 | 382 | 410 | 350 | 0.90 | A |
| 295 | 244 | 238 | 288 | 300 | 185 | 166 | 201 | 195 | 273 | 464 | 267 | 324 | 354 | 302 | 0.92 | A |
| 197 | 119 | 180 | 175 | 202 | 142 | 117 | 104 | 136 | 180 | 241 | 248 | 240 | 295 | 256 | 0.78 | A |
| 138 | 88 | 133 | 117 | 154 | 87 | 91 | 121 | 99 | 124 | 214 | 155 | 243 | 211 | 222 | 0.86 | A |
| 166 | 88 | 125 | 138 | 149 | 91 | 96 | 126 | 143 | 118 | 184 | 161 | 194 | 182 | 183 | 0.94 | A |
| 26 | 71 | 0 | 46 | 74 | 59 | 52 | 31 | 84 | 131 | 166 | 165 | 174 | 168 | 177 | 0.19 | B |
| 33 | 95 | 65 | 71 | 87 | 76 | 67 | 54 | 98 | 204 | 161 | 198 | 174 | 197 | 199 | 0.94 | B |
| 24 | 83 | 63 | 82 | 95 | 80 | 77 | 53 | 102 | 209 | 188 | 193 | 201 | 195 | 200 | 0.98 | B |
| 63 | 71 | 90 | 149 | 110 | 103 | 98 | 76 | 122 | 212 | 248 | 206 | 216 | 209 | 222 | 0.97 | B |
| 62 | 68 | 88 | 114 | 106 | 96 | 84 | 77 | 114 | 204 | 268 | 209 | 214 | 216 | 222 | 0.98 | B |
| 53 | 127 | 142 | 253 | 276 | 201 | 198 | 134 | 164 | 269 | 320 | 278 | 308 | 323 | 303 | 0.92 | B |
| 55 | 179 | 147 | 264 | 306 | 180 | 186 | 124 | 148 | 299 | 403 | 245 | 280 | 289 | 277 | 0.97 | B |
| 47 | 119 | 91 | 176 | 177 | 111 | 115 | 74 | 106 | 115 | 212 | 179 | 189 | 172 | 185 | 0.90 | B |
| 44 | 93 | 83 | 128 | 159 | 107 | 102 | 63 | 85 | 115 | 212 | 161 | 166 | 154 | 169 | 0.97 | B |
| 48 | 123 | 84 | 132 | 186 | 104 | 102 | 69 | 87 | 125 | 190 | 161 | 174 | 189 | 174 | 0.95 | B |
| 43 | 74 | 89 | 142 | 156 | 93 | 95 | 68 | 78 | 120 | 217 | 169 | 176 | 177 | 173 | 0.93 | B |
| 53 | 77 | 57 | 58 | 70 | 65 | 60 | 35 | 81 | 154 | 130 | 132 | 134 | 138 | 140 | 0.61 | B |
| 38 | 70 | 45 | 41 | 54 | 70 | 60 | 25 | 84 | 134 | 106 | 111 | 110 | 119 | 119 | 0.79 | D |
| 44 | 88 | 52 | 47 | 69 | 76 | 68 | 39 | 95 | 135 | 105 | 135 | 123 | 146 | 139 | 0.93 | D |
| 64 | 73 | 73 | 78 | 86 | 108 | 98 | 50 | 118 | 160 | 158 | 160 | 156 | 158 | 160 | 0.89 | D |
| 29 | 93 | 72 | 50 | 56 | 54 | 47 | 40 | 91 | 94 | 132 | 100 | 124 | 135 | 119 | 0.65 | D |
| 37 | 110 | 0 | 57 | 82 | 73 | 71 | 31 | 118 | 147 | 235 | 151 | 169 | 165 | 146 | 0.86 | C |
| 27 | 48 | 68 | 50 | 64 | 51 | 42 | 76 | 82 | 133 | 212 | 120 | 163 | 150 | 154 | 0.89 | C |
| 34 | 39 | 64 | 81 | 66 | 49 | 53 | 65 | 108 | 106 | 147 | 96 | 116 | 111 | 110 | 0.93 | C |
| 40 | 75 | 90 | 48 | 79 | 61 | 52 | 72 | 92 | 125 | 154 | 84 | 116 | 158 | 97 | 0.93 | C |
| 28 | 56 | 77 | 49 | 47 | 44 | 37 | 47 | 72 | 101 | 131 | 99 | 124 | 120 | 108 | 0.91 | C |
| 40 | 37 | 75 | 60 | 59 | 59 | 56 | 31 | 94 | 150 | 150 | 127 | 137 | 133 | 128 | 0.90 | C |
| 57 | 108 | 148 | 126 | 129 | 106 | 109 | 109 | 149 | 179 | 237 | 213 | 240 | 247 | 319 | 0.91 | C |
| 77 | 167 | 169 | 170 | 209 | 157 | 142 | 167 | 144 | 155 | 230 | 195 | 195 | 249 | 148 | 0.88 | C |
| 28 | 71 | 116 | 160 | 187 | 120 | 115 | 89 | 109 | 126 | 202 | 141 | 220 | 193 | 198 | 0.84 | C |
| 23 | 27 | 32 | 32 | 38 | 52 | 38 | 16 | 64 | 105 | 70 | 87 | 99 | 111 | 96 | 0.57 | D |
| 33 | 38 | 32 | 37 | 46 | 52 | 41 | 20 | 69 | 104 | 91 | 114 | 132 | 121 | 115 | 0.86 | D |
| 37 | 92 | 39 | 44 | 51 | 53 | 48 | 18 | 95 | 90 | 104 | 139 | 149 | 153 | 156 | 0.87 | D |
| 21 | 62 | 0 | 37 | 47 | 50 | 40 | 7 | 76 | 85 | 90 | 131 | 147 | 157 | 150 | 0.96 | D |
| 26 | 52 | 22 | 18 | 32 | 29 | 19 | 2 | 56 | 62 | 82 | 104 | 132 | 114 | 107 | 0.96 | D |
| 54 | 96 | 44 | 42 | 63 | 69 | 52 | 26 | 96 | 123 | 92 | 175 | 165 | 199 | 181 | 0.94 | D |
| 43 | 84 | 41 | 39 | 41 | 58 | 52 | 23 | 73 | 101 | 70 | 126 | 137 | 146 | 136 | 0.69 | D |
| 28 | 30 | 11 | 24 | 16 | 33 | 25 | 5 | 38 | 61 | 237 | 96 | 274 | 99 | 86 | 0.62 | D |
| 27 | 84 | 68 | 33 | 41 | 33 | 26 | 21 | 62 | 55 | 70 | 210 | 243 | 252 | 204 | 0.22 | B |
| 21 | 9 | -3 | 5 | 4 | 5 | -4 | 22 | 10 | 3 | 7 | 15 | 50 | 43 | 35 | 0.52 | R |
| 2 | -3 | -2 | 5 | -11 | 1 | -14 | -1 | -7 | -3 | -17 | -7 | 3 | 9 | -5 | 0.58 | R |
| 0 | -4 | -2 | 29 | -13 | -11 | -10 | -4 | 1 | -4 | -17 | -10 | 0 | -10 | -3 | 0.78 | R |
| -3 | -10 | -8 | 2 | 16 | -13 | -19 | -9 | -12 | -6 | -9 | -7 | 4 | -7 | 3 | 0.38 | R |
| 11 | -2 | 0 | 25 | 87 | -16 | -22 | -6 | -18 | -9 | -7 | -10 | 4 | 3 | -21 | 0.78 | R |
| 0.64 | 0.72 | 0.81 | 0.90 | 0.97 | 0.93 | 0.99 | 0.89 | 0.87 | 0.77 | 0.77 | 0.83 | 0.92 | 0.93 | 0.97 | | |

HC CDR3

FIG. 9 (cont.)

SEQUENCE LISTING

```
<160> NUMBER OF SEQ ID NOS: 133

<210> SEQ ID NO 1
<211> LENGTH: 19
<212> TYPE: PRT
<213> ORGANISM: Gallus gallus

<400> SEQUENCE: 1

Ser Gly Asn Arg Asp Tyr Cys Cys Gly Pro Tyr Ser Ser Gly Gln Met
1               5                   10                  15

Asp Ala Trp

<210> SEQ ID NO 2
<211> LENGTH: 19
<212> TYPE: PRT
```

-continued

```
<213> ORGANISM: Gallus gallus

<400> SEQUENCE: 2

Ser Gly Asn Arg Gly Tyr Cys Cys Gly Pro Tyr Ser Ser Gly Gln Met
1               5                   10                  15

Asp Ala Trp

<210> SEQ ID NO 3
<211> LENGTH: 19
<212> TYPE: PRT
<213> ORGANISM: Gallus gallus

<400> SEQUENCE: 3

Ser Ala Asn Arg Gly Tyr Cys Cys Gly Pro Tyr Ser Ser Gly Gln Met
1               5                   10                  15

Asp Ala Trp

<210> SEQ ID NO 4
<211> LENGTH: 19
<212> TYPE: PRT
<213> ORGANISM: Gallus gallus

<400> SEQUENCE: 4

Ser Ala Asn Ser Gly Tyr Cys Cys Gly Pro Tyr Ser Ser Gly Gln Met
1               5                   10                  15

Asp Ala Trp

<210> SEQ ID NO 5
<211> LENGTH: 19
<212> TYPE: PRT
<213> ORGANISM: Gallus gallus

<400> SEQUENCE: 5

Ser Ala Asn Ser Gly Tyr Cys Cys Gly Pro Tyr Ser Ala Gly Gln Met
1               5                   10                  15

Asp Ala Trp

<210> SEQ ID NO 6
<211> LENGTH: 29
<212> TYPE: PRT
<213> ORGANISM: Gallus gallus

<400> SEQUENCE: 6

Ala Ala Val Ser Gly His Cys Tyr Ile Gly Thr Ala Tyr Pro Gly Leu
1               5                   10                  15

Thr Cys Gly Ala Tyr Thr Ala Ile Thr Ile Asp Ser Trp
            20                  25

<210> SEQ ID NO 7
<211> LENGTH: 27
<212> TYPE: PRT
<213> ORGANISM: Gallus gallus

<400> SEQUENCE: 7

Ala Ala Val Ser Gly His Cys Tyr Ile Gly Ala Ser Gly Leu Thr Cys
1               5                   10                  15

Gly Ala Tyr Thr Ala Ile Thr Ile Asp Ser Trp
            20                  25

<210> SEQ ID NO 8
<211> LENGTH: 28
```

-continued

```
<212> TYPE: PRT
<213> ORGANISM: Gallus gallus

<400> SEQUENCE: 8

Ser Ala Gly Ser Gly Tyr Cys Gly Trp Asn Pro Ser Tyr Asn Phe Asn
1               5                   10                  15

Cys Gly Ala Tyr Ile Ala Ala Thr Val Asp Ala Trp
            20                  25

<210> SEQ ID NO 9
<211> LENGTH: 28
<212> TYPE: PRT
<213> ORGANISM: Gallus gallus

<400> SEQUENCE: 9

Ser Ala Ser Gly Gly Tyr Cys Trp Phe Ser Asp Arg Ser Ile Leu Thr
1               5                   10                  15

Cys Asn Gly Gly Gly Gly Ser Ala Ile Asp Ala Trp
            20                  25

<210> SEQ ID NO 10
<211> LENGTH: 28
<212> TYPE: PRT
<213> ORGANISM: Gallus gallus

<400> SEQUENCE: 10

Ser Ala Ser Gly Gly Tyr Cys Trp Phe Thr Asp Arg Ser Ile Leu Thr
1               5                   10                  15

Cys Asn Gly Gly Gly Gly Thr Ala Ile Asp Ala Trp
            20                  25

<210> SEQ ID NO 11
<211> LENGTH: 19
<212> TYPE: PRT
<213> ORGANISM: Gallus gallus

<400> SEQUENCE: 11

Ser Ala Arg Ser Gly Thr Gly Cys Cys Arg Asn Tyr Ile Gly Phe Ile
1               5                   10                  15

Asp Ala Trp

<210> SEQ ID NO 12
<211> LENGTH: 19
<212> TYPE: PRT
<213> ORGANISM: Gallus gallus

<400> SEQUENCE: 12

Ser Ala Tyr Thr Gly Gly Tyr Cys Cys Arg Asn Tyr Ile Gly His Ile
1               5                   10                  15

Asp Ala Trp

<210> SEQ ID NO 13
<211> LENGTH: 19
<212> TYPE: PRT
<213> ORGANISM: Gallus gallus

<400> SEQUENCE: 13

Ser Gly Phe Ser Gly Gly Val Leu Val Val Gly Asp Ala Ala Tyr Ile
1               5                   10                  15

Asp Ala Trp
```

```
<210> SEQ ID NO 14
<211> LENGTH: 13
<212> TYPE: PRT
<213> ORGANISM: Gallus gallus

<400> SEQUENCE: 14

Gly Ala Ala Ser Gly Ser Ala Ala Asp Ile Asp Ala Trp
1               5                   10

<210> SEQ ID NO 15
<211> LENGTH: 19
<212> TYPE: PRT
<213> ORGANISM: Gallus gallus

<400> SEQUENCE: 15

Asp Ser Gly Leu Ile Leu Phe Gly Pro Val Ile Ser Ile Gly Ser Phe
1               5                   10                  15

Asp Ala Trp

<210> SEQ ID NO 16
<211> LENGTH: 19
<212> TYPE: PRT
<213> ORGANISM: Gallus gallus

<400> SEQUENCE: 16

Asp Ser Gly Leu Ile Leu Phe Gly Pro Val Val Ser Ile Gly Ser Ile
1               5                   10                  15

Asp Ala Trp

<210> SEQ ID NO 17
<211> LENGTH: 19
<212> TYPE: PRT
<213> ORGANISM: Gallus gallus

<400> SEQUENCE: 17

Asp Ser Ser Leu Met Leu Phe Gly Ile Val Val Ser Ile Gly Gly Ile
1               5                   10                  15

Asp Val Trp

<210> SEQ ID NO 18
<211> LENGTH: 19
<212> TYPE: PRT
<213> ORGANISM: Gallus gallus

<400> SEQUENCE: 18

Asn Thr Val Gly Trp Ala Ala Val Leu Leu Val Asp Ala Gly Leu Ile
1               5                   10                  15

Asp Ala Trp

<210> SEQ ID NO 19
<211> LENGTH: 14
<212> TYPE: PRT
<213> ORGANISM: Gallus gallus

<400> SEQUENCE: 19

Asp Gly Ser Tyr Gly Cys Gly Ser Gly Cys Leu Asp Ala Trp
1               5                   10

<210> SEQ ID NO 20
<211> LENGTH: 19
<212> TYPE: PRT
<213> ORGANISM: Gallus gallus
```

-continued

```
<400> SEQUENCE: 20

Ala Val Gly Ser Cys Thr Tyr Gly Asn Gly Cys Gly Val Gly Gly Ile
1               5                   10                  15

Asp Ala Trp

<210> SEQ ID NO 21
<211> LENGTH: 16
<212> TYPE: PRT
<213> ORGANISM: Gallus gallus

<400> SEQUENCE: 21

Ser Ala Tyr Gly Cys Cys Gly Thr Asp Ala Tyr Ser Leu Asp Ala Trp
1               5                   10                  15

<210> SEQ ID NO 22
<211> LENGTH: 16
<212> TYPE: PRT
<213> ORGANISM: Gallus gallus

<400> SEQUENCE: 22

Val Ala Gly Gly His Cys Asp Trp Gly Ala Gly Cys Ile Asp Thr Trp
1               5                   10                  15

<210> SEQ ID NO 23
<211> LENGTH: 17
<212> TYPE: PRT
<213> ORGANISM: Gallus gallus

<400> SEQUENCE: 23

Ala Ala Gly Gly Trp Phe Gly Trp Ser Ser Ala Gly Ser Ile Asp Ala
1               5                   10                  15

Trp

<210> SEQ ID NO 24
<211> LENGTH: 17
<212> TYPE: PRT
<213> ORGANISM: Gallus gallus

<400> SEQUENCE: 24

Ala Ala Gly Ser Trp Phe Gly Trp Ser Ser Ala Gly Cys Ile Asp Ser
1               5                   10                  15

Trp

<210> SEQ ID NO 25
<211> LENGTH: 10
<212> TYPE: PRT
<213> ORGANISM: Gallus gallus

<400> SEQUENCE: 25

Gly Ala Tyr Gly Ala Ser Ile Asp Ala Trp
1               5                   10

<210> SEQ ID NO 26
<211> LENGTH: 16
<212> TYPE: PRT
<213> ORGANISM: Gallus gallus

<400> SEQUENCE: 26

Val Ala Gly Gly His Cys Asp Trp Gly Ala Gly Cys Ile Asp Ala Trp
1               5                   10                  15

<210> SEQ ID NO 27
```

```
<211> LENGTH: 16
<212> TYPE: PRT
<213> ORGANISM: Gallus gallus

<400> SEQUENCE: 27

Asn Asp Ile Gly Cys Trp Gly Leu Arg Ala Gly Cys Ile Asp Ala Trp
1               5                   10                  15

<210> SEQ ID NO 28
<211> LENGTH: 19
<212> TYPE: PRT
<213> ORGANISM: Gallus gallus

<400> SEQUENCE: 28

Asn Ala Asp Phe Gly Tyr Ser Trp Ser Trp Thr Tyr Thr Ala Ser Ile
1               5                   10                  15

Asp Ala Trp

<210> SEQ ID NO 29
<211> LENGTH: 26
<212> TYPE: PRT
<213> ORGANISM: Gallus gallus

<400> SEQUENCE: 29

Asn Ala Ala Ser Gly Tyr Cys Gly Trp Ser Val Tyr Ser Gly His Asp
1               5                   10                  15

Phe Asn Cys Ala Ser Thr Ile Asp Ala Trp
            20                  25

<210> SEQ ID NO 30
<211> LENGTH: 17
<212> TYPE: PRT
<213> ORGANISM: Gallus gallus

<400> SEQUENCE: 30

Asp Gly Gly Phe Cys Gly Arg Gly Gly Cys Thr Ala Thr Ile Asp Ala
1               5                   10                  15

Trp

<210> SEQ ID NO 31
<211> LENGTH: 16
<212> TYPE: PRT
<213> ORGANISM: Gallus gallus

<400> SEQUENCE: 31

Cys Ala Tyr Ser Ala Gly Tyr Asp Cys Gly Gly Ala Ile Asp Ala Trp
1               5                   10                  15

<210> SEQ ID NO 32
<211> LENGTH: 151
<212> TYPE: PRT
<213> ORGANISM: Homo sapiens

<400> SEQUENCE: 32

Met Thr Thr Ser Pro Ile Leu Gln Leu Leu Leu Arg Leu Ser Leu Cys
1               5                   10                  15

Gly Leu Leu Leu Gln Arg Ala Glu Thr Gly Ser Lys Gly Gln Thr Ala
            20                  25                  30

Gly Glu Leu Tyr Gln Arg Trp Glu Arg Tyr Arg Arg Glu Cys Gln Glu
        35                  40                  45

Thr Leu Ala Ala Ala Glu Pro Pro Ser Gly Leu Ala Cys Asn Gly Ser
    50                  55                  60
```

-continued

```
Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
    130                 135                 140

Tyr Ser Leu Ser Leu Ala Thr
145                 150

<210> SEQ ID NO 33
<211> LENGTH: 147
<212> TYPE: PRT
<213> ORGANISM: Mus musculus

<400> SEQUENCE: 33

Met Pro Leu Arg Leu Leu Leu Leu Leu Leu Trp Leu Trp Gly Leu Gln
1               5                   10                  15

Trp Ala Glu Thr Asp Ser Glu Gly Gln Thr Thr Thr Gly Glu Leu Tyr
                20                  25                  30

Gln Arg Trp Glu His Tyr Gly Gln Glu Cys Gln Lys Met Leu Glu Thr
            35                  40                  45

Thr Glu Pro Pro Ser Gly Leu Ala Cys Asn Gly Ser Phe Asp Met Tyr
        50                  55                  60

Ala Cys Trp Asn Tyr Thr Ala Ala Asn Thr Thr Ala Arg Val Ser Cys
65                  70                  75                  80

Pro Trp Tyr Leu Pro Trp Phe Arg Gln Val Ser Ala Gly Phe Val Phe
                85                  90                  95

Arg Gln Cys Gly Ser Asp Gly Gln Trp Gly Ser Trp Arg Asp His Thr
            100                 105                 110

Gln Cys Glu Asn Pro Glu Lys Asn Gly Ala Phe Gln Asp Gln Thr Leu
        115                 120                 125

Ile Leu Glu Arg Leu Gln Ile Met Tyr Thr Val Gly Tyr Ser Leu Ser
    130                 135                 140

Leu Thr Thr
145

<210> SEQ ID NO 34
<211> LENGTH: 148
<212> TYPE: PRT
<213> ORGANISM: Rattus norvegicus

<400> SEQUENCE: 34

Met Pro Leu Arg Leu Leu Leu Leu Leu Leu Trp Leu Trp Gly Leu Ser
1               5                   10                  15

Leu Gln Arg Ala Glu Thr Asp Ser Glu Gly Gln Thr Thr Gly Glu Leu
                20                  25                  30

Tyr Gln Arg Trp Glu Arg Tyr Gly Trp Glu Cys Gln Asn Thr Leu Glu
            35                  40                  45

Ala Thr Glu Pro Pro Ser Gly Leu Ala Cys Asn Gly Ser Phe Asp Met
        50                  55                  60

Tyr Ala Cys Trp Asn Tyr Thr Ala Ala Asn Thr Thr Ala Arg Val Ser
65                  70                  75                  80
```

-continued

Cys Pro Trp Tyr Leu Pro Trp Tyr Arg Gln Val Ala Ala Gly Phe Val
                85                  90                  95

Phe Arg Gln Cys Gly Ser Asp Gly Gln Trp Gly Ser Trp Arg Asp His
            100                 105                 110

Thr Gln Cys Glu Asn Pro Glu Lys Asn Gly Ala Phe Gln Asp Gln Lys
        115                 120                 125

Leu Ile Leu Glu Arg Leu Gln Val Val Tyr Thr Val Gly Tyr Ser Leu
    130                 135                 140

Ser Leu Ala Thr
145

<210> SEQ ID NO 35
<211> LENGTH: 128
<212> TYPE: PRT
<213> ORGANISM: Gallus gallus

<400> SEQUENCE: 35

Ala Ala Val Thr Leu Asp Glu Ser Gly Gly Gly Leu Gln Thr Pro Gly
1               5                   10                  15

Gly Thr Leu Ser Leu Val Cys Lys Gly Ser Gly Phe Asp Phe Ser Asp
            20                  25                  30

Tyr Gly Met Gly Trp Val Arg Gln Ala Pro Gly Lys Gly Leu Glu Trp
        35                  40                  45

Val Ala Gly Ile Glu Asn Asp Gly Ser Gly Ala Gly Tyr Gly Ala Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Ile Tyr Tyr
                85                  90                  95

Cys Ala Arg Asp Ser Gly Leu Ile Leu Phe Gly Pro Val Val Ser Ile
            100                 105                 110

Gly Ser Ile Asp Ala Trp Gly His Gly Thr Glu Val Ile Val Ser Ser
        115                 120                 125

<210> SEQ ID NO 36
<211> LENGTH: 128
<212> TYPE: PRT
<213> ORGANISM: Gallus gallus

<400> SEQUENCE: 36

Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Leu Asp Phe Ser Arg
            20                  25                  30

Phe Asn Met Phe Trp Val Arg Gln Ala Pro Gly Lys Gly Leu Glu Phe
        35                  40                  45

Val Ala Gly Thr Asp Ser Thr Gly Ile Trp Lys Asp Tyr Gly Pro Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Ser Ala Lys Ser Ala Asn Ser Gly Tyr Cys Cys Gly Pro Tyr Ser Ala
            100                 105                 110

Gly Gln Met Asp Ala Trp Gly His Gly Thr Glu Val Ile Val Ser Ser
        115                 120                 125

<210> SEQ ID NO 37
<211> LENGTH: 128
<212> TYPE: PRT
<213> ORGANISM: Gallus gallus

<400> SEQUENCE: 37

```
Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Asp Phe Thr Ser
            20                  25                  30

His Gly Met Gly Trp Val Arg Gln Ala Pro Gly Gln Gly Leu Glu Trp
        35                  40                  45

Val Ala Gly Val Glu Ser Asp Gly Ser Ser Ala Gly Tyr Gly Ala Ala
    50                  55                  60

Val Gln Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Ala Ile Tyr Tyr
                85                  90                  95

Cys Val Arg Asp Ser Ser Leu Met Leu Phe Gly Ile Val Val Ser Ile
            100                 105                 110

Gly Gly Ile Asp Val Trp Gly His Gly Thr Glu Val Ile Val Ser Ser
        115                 120                 125
```

<210> SEQ ID NO 38
<211> LENGTH: 128
<212> TYPE: PRT
<213> ORGANISM: Gallus gallus

<400> SEQUENCE: 38

```
Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Asp Phe Thr Ser
            20                  25                  30

His Gly Met Gly Trp Val Arg Gln Ala Pro Gly Lys Gly Leu Glu Trp
        35                  40                  45

Val Ala Gly Ile Glu Ser Asp Gly Ser Ser Ala Gly Tyr Gly Ala Ala
    50                  55                  60

Val Gln Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Ala Ile Tyr Tyr
                85                  90                  95

Cys Val Arg Asp Ser Ser Leu Met Leu Phe Gly Ile Val Val Ser Ile
            100                 105                 110

Gly Gly Ile Asp Val Trp Gly His Gly Thr Glu Val Ile Val Ser Ser
        115                 120                 125
```

<210> SEQ ID NO 39
<211> LENGTH: 128
<212> TYPE: PRT
<213> ORGANISM: Gallus gallus

<400> SEQUENCE: 39

```
Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Asp Phe Ser Arg
            20                  25                  30
```

Phe Asn Met Phe Trp Val Arg Gln Ala Pro Gly Lys Gly Leu Glu Tyr
          35                      40                      45

Val Ala Gly Ile Asp Ala Thr Gly Thr Trp Thr Asp Tyr Gly Pro Ala
      50                      55                      60

Val Lys Gly Arg Ala Thr Ile Ser Arg Asp Asn Gly Gln Ser Thr Leu
65                      70                      75                      80

Arg Leu Gln Leu Asn Thr Leu Arg Ala Glu Asp Thr Ala Thr Tyr Tyr
                  85                      90                      95

Cys Ala Lys Ser Ala Asn Arg Gly Tyr Cys Cys Gly Pro Tyr Ser Ser
              100                     105                     110

Gly Gln Met Asp Ala Trp Gly His Gly Thr Glu Val Ile Val Ser Ser
          115                     120                     125

<210> SEQ ID NO 40
<211> LENGTH: 128
<212> TYPE: PRT
<213> ORGANISM: Gallus gallus

<400> SEQUENCE: 40

Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Thr Phe Ser Ser
              20                      25                      30

Phe Asn Met Phe Trp Val Arg Gln Ala Pro Gly Lys Gly Leu Glu Phe
          35                      40                      45

Val Ala Gly Ile Asp Ala Thr Gly Thr Trp Thr Asp Tyr Gly Pro Ala
      50                      55                      60

Val Lys Ser Arg Ala Thr Ile Ser Arg Asp Asn Gly Gln Ser Thr Val
65                      70                      75                      80

Arg Leu Gln Leu Asn His Leu Arg Ala Glu Asp Thr Ala Thr Tyr Phe
                  85                      90                      95

Cys Thr Arg Ser Gly Asn Arg Asp Tyr Cys Cys Gly Pro Tyr Ser Ser
              100                     105                     110

Gly Gln Met Asp Ala Trp Gly His Gly Thr Glu Val Ile Val Ser Ser
          115                     120                     125

<210> SEQ ID NO 41
<211> LENGTH: 128
<212> TYPE: PRT
<213> ORGANISM: Gallus gallus

<400> SEQUENCE: 41

Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Thr Phe Ser Ser
              20                      25                      30

Phe Asn Met Phe Trp Val Arg Gln Ala Pro Gly Lys Gly Leu Glu Phe
          35                      40                      45

Val Ala Gly Ile Asp Ala Thr Gly Thr Trp Thr Asp Tyr Gly Pro Ala
      50                      55                      60

Val Lys Gly Arg Ala Thr Ile Ser Arg Asp Asn Gly Gln Ser Thr Val
65                      70                      75                      80

Arg Leu Gln Leu Asn His Leu Arg Ala Glu Asp Thr Ala Thr Tyr Phe
                  85                      90                      95

Cys Thr Arg Ser Gly Asn Arg Gly Tyr Cys Cys Gly Pro Tyr Ser Ser
              100                     105                     110

-continued

```
Gly Gln Met Asp Ala Trp Gly His Gly Thr Glu Val Ile Val Ser Ser
        115                 120                 125

<210> SEQ ID NO 42
<211> LENGTH: 128
<212> TYPE: PRT
<213> ORGANISM: Gallus gallus

<400> SEQUENCE: 42

Ala Ala Val Thr Leu Asp Glu Ser Gly Gly Gly Leu Arg Thr Pro Gly
1               5                   10                  15

Gly Thr Leu Ser Leu Val Cys Lys Gly Ser Gly Phe Asp Phe Asn Ser
            20                  25                  30

Tyr Gly Met Gly Trp Val Arg Gln Ala Pro Gly Lys Gly Leu Glu Trp
        35                  40                  45

Val Ala Gly Ile Glu Asn Asp Gly Ser Gly Ala Gly Tyr Gly Pro Ala
    50                  55                  60

Val Arg Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Phe
                85                  90                  95

Cys Ala Arg Asp Ser Gly Leu Ile Leu Phe Gly Pro Val Ile Ser Ile
            100                 105                 110

Gly Ser Phe Asp Ala Trp Gly His Gly Thr Glu Val Ile Val Ser Ser
        115                 120                 125

<210> SEQ ID NO 43
<211> LENGTH: 128
<212> TYPE: PRT
<213> ORGANISM: Gallus gallus

<400> SEQUENCE: 43

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Thr Phe Ser Thr
            20                  25                  30

Phe Asn Met Phe Trp Val Arg Gln Ala Pro Gly Lys Gly Leu Glu Tyr
        35                  40                  45

Val Ala Gly Ile Asp Ala Thr Gly Thr Trp Thr Asp Tyr Gly Pro Ala
    50                  55                  60

Val Lys Gly Arg Ala Thr Ile Ser Arg Asp Asn Gly Gln Ser Thr Leu
65                  70                  75                  80

Arg Leu Gln Leu Asn Asn Leu Arg Ala Glu Asp Thr Gly Thr Tyr Phe
                85                  90                  95

Cys Ala Arg Ser Ala Asn Arg Gly Tyr Cys Cys Gly Pro Tyr Ser Ser
            100                 105                 110

Gly Gln Met Asp Ala Trp Gly His Gly Thr Glu Val Ile Val Ser Ser
        115                 120                 125

<210> SEQ ID NO 44
<211> LENGTH: 128
<212> TYPE: PRT
<213> ORGANISM: Gallus gallus

<400> SEQUENCE: 44

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Thr Phe Ser Arg
```

-continued

```
              20                  25                  30

Phe Asn Leu Phe Trp Val Arg Gln Ala Pro Gly Lys Gly Leu Glu Phe
        35                  40                  45

Val Ala Gly Ile Asp Ala Thr Gly Thr Trp Thr Asp Tyr Gly Pro Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Ala Thr Tyr Tyr
                85                  90                  95

Cys Ala Lys Ser Ala Asn Ser Gly Tyr Cys Cys Gly Pro Tyr Ser Ser
                100                 105                 110

Gly Gln Met Asp Ala Trp Gly His Gly Thr Glu Val Ile Val Ser Ser
            115                 120                 125
```

```
<210> SEQ ID NO 45
<211> LENGTH: 128
<212> TYPE: PRT
<213> ORGANISM: Gallus gallus

<400> SEQUENCE: 45
```

```
Ala Ala Val Thr Leu Asp Glu Ser Gly Gly Gly Leu Gln Thr Pro Gly
1               5                   10                  15

Gly Thr Leu Ser Leu Val Cys Lys Gly Ser Gly Phe Thr Phe Ser Asp
                20                  25                  30

Tyr Gly Met Gly Trp Val Arg Gln Ala Pro Gly Lys Gly Leu Glu Trp
        35                  40                  45

Val Ala Gly Ile Glu Asn Asp Gly Ser Gly Glu Gly Tyr Gly Pro Ala
    50                  55                  60

Val Arg Gly Arg Ala Thr Ile Ser Arg Asp Asn Gly Gln Ser Thr Val
65                  70                  75                  80

Arg Leu Gln Leu Asn Asn Leu Arg Ala Glu Asp Ser Gly Thr Tyr Tyr
                85                  90                  95

Cys Ala Arg Asp Ser Gly Leu Ile Leu Phe Gly Pro Val Ile Ser Ile
            100                 105                 110

Gly Ser Phe Asp Ala Trp Gly His Gly Thr Glu Val Ile Val Ser Ser
            115                 120                 125
```

```
<210> SEQ ID NO 46
<211> LENGTH: 134
<212> TYPE: PRT
<213> ORGANISM: Gallus gallus

<400> SEQUENCE: 46
```

```
Ala Ala Val Thr Leu Asp Glu Ser Gly Gly Gly Leu Arg Thr Pro Gly
1               5                   10                  15

Gly Thr Leu Ser Leu Val Cys Lys Gly Ser Gly Phe Thr Phe Ser Ser
                20                  25                  30

Asn Met Gly Trp Ile Arg Gln Ala Pro Gly Lys Gly Leu Glu Tyr Val
        35                  40                  45

Ala Ala Ile Ser Ser Asp Gly Arg Asp Thr Thr Tyr Gly Ala Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Pro Glu Asp Thr Gly Ile Tyr Tyr Cys
                85                  90                  95

Ala Lys Asn Ala Ala Ser Gly Tyr Cys Gly Trp Ser Val Tyr Ser Gly
```

-continued

```
            100             105             110

His Asp Phe Asn Cys Ala Ser Thr Ile Asp Ala Trp Gly His Gly Thr
        115                 120                 125

Glu Val Ile Val Ser Ser
    130

<210> SEQ ID NO 47
<211> LENGTH: 124
<212> TYPE: PRT
<213> ORGANISM: Gallus gallus

<400> SEQUENCE: 47

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Thr Phe Ser Asp
            20                  25                  30

Tyr Ser Val Gln Trp Val Arg Gln Ala Pro Gly Lys Gly Leu Glu Trp
        35                  40                  45

Val Ala Gly Ile Ser Ser Gly Gly Ser Ala Trp Tyr Gly Ala Ala Val
    50                  55                  60

Lys Gly Arg Ala Thr Ile Ser Arg Gly Asn Gly Gln Ser Thr Leu Arg
65                  70                  75                  80

Leu Gln Leu Asn Asn Leu Arg Ala Glu Asp Thr Ala Thr Tyr Phe Cys
            85                  90                  95

Ala Lys Asn Asp Ile Gly Cys Trp Gly Leu Arg Ala Gly Cys Ile Asp
            100                 105                 110

Ala Trp Gly His Gly Thr Glu Val Ile Val Ser Ser
        115                 120

<210> SEQ ID NO 48
<211> LENGTH: 128
<212> TYPE: PRT
<213> ORGANISM: Gallus gallus

<400> SEQUENCE: 48

Ala Ala Val Thr Leu Asp Glu Ser Gly Gly Gly Leu Gln Thr Pro Gly
1               5                   10                  15

Gly Gly Leu Ser Leu Val Cys Lys Ala Ser Gly Phe Ser Phe Ser Glu
            20                  25                  30

Tyr Gly Met Gly Trp Met Arg Gln Ala Pro Gly Lys Gly Leu Glu Phe
        35                  40                  45

Val Ala Ala Ile Asp Asn Asp Gly Leu Asn Thr Gly Tyr Gly Ser Ala
    50                  55                  60

Val Gln Gly Arg Ala Thr Ile Ser Arg Asp Asn Gly Gln Ser Thr Val
65                  70                  75                  80

Arg Leu Gln Leu Ser Asn Leu Arg Ser Glu Asp Thr Gly Thr Tyr Tyr
            85                  90                  95

Cys Ala Lys Ser Ala Tyr Thr Gly Gly Tyr Cys Cys Arg Asn Tyr Ile
            100                 105                 110

Gly His Ile Asp Ala Trp Gly His Gly Thr Glu Val Ile Val Ser Ser
        115                 120                 125

<210> SEQ ID NO 49
<211> LENGTH: 122
<212> TYPE: PRT
<213> ORGANISM: Gallus gallus

<400> SEQUENCE: 49
```

-continued

```
Ala Ala Val Thr Leu Asp Glu Ser Gly Gly Gly Leu Gln Thr Pro Gly
1               5                   10                  15

Gly Gly Leu Ser Leu Val Cys Lys Gly Ser Gly Phe Thr Phe Ser Ser
            20                  25                  30

Phe Asn Met Tyr Trp Val Arg Gln Ala Pro Gly Lys Gly Leu Glu Phe
        35                  40                  45

Val Ala Gly Ile Ser Pro Asn Gly Ile His Thr Tyr Tyr Ala Ser Ala
    50                  55                  60

Met Lys Gly Arg Ala Thr Ile Ser Arg Asp Asn Gly Gln Ser Thr Val
65                  70                  75                  80

Ser Leu Gln Leu Asn Asn Leu Arg Thr Glu Asp Thr Gly Thr Tyr Phe
                85                  90                  95

Cys Ala Arg Gly Ala Ala Ser Gly Ser Ala Ala Asp Ile Asp Ala Trp
            100                 105                 110

Gly His Gly Thr Glu Val Ile Val Ser Ser
            115                 120
```

<210> SEQ ID NO 50
<211> LENGTH: 126
<212> TYPE: PRT
<213> ORGANISM: Gallus gallus

<400> SEQUENCE: 50

```
Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Asp Phe Thr Ser
            20                  25                  30

Asp Thr Met Gly Trp Met Arg Gln Ala Pro Gly Lys Gly Leu Glu Trp
        35                  40                  45

Val Ala Thr Ile Ser Arg Asp Gly Ser Asp Thr Ala Tyr Gly Ala Ala
    50                  55                  60

Val Lys Gly Arg Ala Thr Ile Ser Arg Asp Asn Gly Gln Ser Thr Val
65                  70                  75                  80

Thr Leu Gln Leu Asn Asn Leu Arg Ala Glu Asp Thr Gly Ile Tyr Tyr
                85                  90                  95

Cys Thr Lys Asp Gly Gly Phe Cys Gly Arg Gly Gly Cys Thr Ala Thr
            100                 105                 110

Ile Asp Ala Trp Gly His Gly Thr Glu Val Ile Val Ser Ser
            115                 120                 125
```

<210> SEQ ID NO 51
<211> LENGTH: 124
<212> TYPE: PRT
<213> ORGANISM: Gallus gallus

<400> SEQUENCE: 51

```
Ala Ala Val Thr Leu Asp Glu Ser Gly Gly Gly Leu Gln Thr Pro Gly
1               5                   10                  15

Gly Gly Leu Gly Leu Val Cys Lys Ala Ser Gly Phe Ile Phe Asn Ser
            20                  25                  30

Tyr Gly Met Gly Trp Met Arg Gln Ala Pro Gly Lys Gly Leu Glu Tyr
        35                  40                  45

Ile Ala Thr Ile Ser Ser Gly Gly Ser Lys Tyr Tyr Ala Ser Ala Val
    50                  55                  60

Gln Gly Arg Val Thr Ile Ser Arg Asp Asn Gly Gln Ser Thr Val Arg
65                  70                  75                  80
```

```
Leu Gln Leu Asn Asp Leu Arg Ala Glu Asp Thr Gly Ile Tyr Tyr Cys
            85                  90                  95

Thr Lys Cys Ala Tyr Ser Ala Gly Tyr Asp Cys Gly Gly Ala Ile Asp
            100                 105                 110

Ala Trp Gly His Gly Thr Glu Val Ile Val Ser Ser
        115                 120

<210> SEQ ID NO 52
<211> LENGTH: 128
<212> TYPE: PRT
<213> ORGANISM: Gallus gallus

<400> SEQUENCE: 52

Ala Ala Val Thr Leu Asp Glu Ser Gly Gly Ser Leu Gln Thr Pro Gly
1               5                   10                  15

Gly Gly Leu Ser Leu Val Cys Lys Ala Ser Gly Phe Thr Phe Ser Ser
            20                  25                  30

Val Asn Met Gly Trp Val Arg Gln Ala Pro Gly Lys Gly Leu Glu Phe
        35                  40                  45

Val Ala Gly Ile Asp Asn Thr Gly Gly Ser Thr Tyr Tyr Gly Ser Ala
        50                  55                  60

Val Asp Gly Arg Ala Thr Ile Ser Arg Asp Asn Gly Gln Asp Thr Val
65                  70                  75                  80

Arg Leu Gln Leu Asp Asn Leu Arg Ala Glu Asp Thr Gly Thr Tyr Tyr
            85                  90                  95

Cys Ala Lys Ser Ala Arg Ser Gly Thr Gly Cys Cys Arg Asn Tyr Ile
            100                 105                 110

Gly Phe Ile Asp Ala Trp Gly His Gly Thr Glu Val Ile Val Ser Ser
        115                 120                 125

<210> SEQ ID NO 53
<211> LENGTH: 128
<212> TYPE: PRT
<213> ORGANISM: Gallus gallus

<400> SEQUENCE: 53

Ala Ala Val Thr Leu Asp Glu Ser Gly Gly Gly Leu Gln Thr Pro Gly
1               5                   10                  15

Gly Thr Leu Ser Leu Val Cys Lys Ala Ser Gly Phe Thr Phe Ser Ser
            20                  25                  30

Val Asn Met Gly Trp Val Arg Gln Ala Pro Gly Lys Gly Leu Glu Phe
        35                  40                  45

Val Ala Gly Ile Asp Asn Thr Gly Gly Ala Thr Tyr Tyr Ala Ser Ala
        50                  55                  60

Val Gly Gly Arg Ala Thr Ile Ser Arg Asp Asn Gly Gln Asp Thr Val
65                  70                  75                  80

Ser Leu Gln Leu Asp Asn Leu Arg Ala Glu Asp Thr Gly Thr Tyr Tyr
            85                  90                  95

Cys Ala Lys Ser Ala Arg Ser Gly Thr Gly Cys Cys Arg Asn Tyr Ile
            100                 105                 110

Gly Phe Ile Asp Ala Trp Gly His Gly Thr Glu Val Ile Val Ser Ser
        115                 120                 125

<210> SEQ ID NO 54
<211> LENGTH: 126
<212> TYPE: PRT
<213> ORGANISM: Gallus gallus
```

```
<400> SEQUENCE: 54

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Thr Phe Asn Asp
            20                  25                  30

Arg Gly Met His Trp Val Arg Gln Ala Pro Gly Lys Gly Leu Glu Tyr
        35                  40                  45

Val Ala Val Ile Ser Lys Asp Gly Gly Glu Ile Tyr Tyr Gly Ala Ala
    50                  55                  60

Val Lys Gly Arg Ala Thr Ile Ser Arg Asp Asn Gly Gln Ser Ile Val
65                  70                  75                  80

Arg Leu Gln Leu Asn Asn Leu Arg Ala Glu Asp Thr Gly Thr Tyr Tyr
                85                  90                  95

Cys Ala Arg Ala Ala Gly Ser Trp Phe Gly Trp Ser Ser Ala Gly Cys
            100                 105                 110

Ile Asp Ser Trp Gly His Gly Thr Glu Val Ile Val Ser Ser
            115                 120                 125

<210> SEQ ID NO 55
<211> LENGTH: 125
<212> TYPE: PRT
<213> ORGANISM: Gallus gallus

<400> SEQUENCE: 55

Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Thr Phe Ser Asn
            20                  25                  30

Tyr Ala Met Gly Trp Met Arg Gln Ala Pro Gly Lys Gly Leu Glu Tyr
        35                  40                  45

Val Ala Gly Ile Arg Ser Asp Gly Ser Tyr Pro Ser Tyr Gly Ala Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Phe
                85                  90                  95

Cys Ala Lys Val Ala Gly Gly His Cys Asp Trp Gly Ala Gly Cys Ile
            100                 105                 110

Asp Thr Trp Gly His Gly Thr Glu Val Ile Val Ser Ser
            115                 120                 125

<210> SEQ ID NO 56
<211> LENGTH: 133
<212> TYPE: PRT
<213> ORGANISM: Gallus gallus

<400> SEQUENCE: 56

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Ser Ile Ser Ser
            20                  25                  30

Tyr Thr Met Tyr Trp Val Arg Gln Ala Pro Gly Glu Gly Leu Glu Phe
        35                  40                  45

Val Ala Gly Ile Asp Asn Thr Ala Asn Tyr Arg Gly Tyr Gly Ser Ala
    50                  55                  60
```

```
Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Phe
                85                  90                  95

Cys Ala Lys Asp Val Tyr Asp Phe Ser Arg Ile Phe Asp Gly Thr Tyr
            100                 105                 110

Ser Gly Gly Gly Ala Pro Asn Ile Asp Ala Trp Gly His Gly Thr Glu
        115                 120                 125

Val Ile Val Ser Ser
    130

<210> SEQ ID NO 57
<211> LENGTH: 126
<212> TYPE: PRT
<213> ORGANISM: Gallus gallus

<400> SEQUENCE: 57

Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Thr Phe Ser Asn
            20                  25                  30

Tyr Ala Met Gly Trp Met Arg Gln Ala Pro Gly Lys Gly Leu Glu Phe
        35                  40                  45

Val Ala Gly Ile Val Gly Ser Ser Gly Thr Ser Thr Ala Tyr Gly Ala
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Phe Cys Ala Lys Val Ala Gly Gly His Cys Asp Trp Gly Ala Gly Cys
            100                 105                 110

Ile Asp Ala Trp Gly His Gly Thr Glu Val Ile Val Ser Ser
        115                 120                 125

<210> SEQ ID NO 58
<211> LENGTH: 125
<212> TYPE: PRT
<213> ORGANISM: Gallus gallus

<400> SEQUENCE: 58

Ala Ala Val Thr Leu Asp Glu Ser Gly Gly Gly Leu Gln Thr Pro Gly
1               5                   10                  15

Gly Ala Leu Ser Leu Ala Cys Lys Gly Ser Gly Phe Thr Phe Ser Asn
            20                  25                  30

Tyr Ala Met Gly Trp Met Arg Gln Ala Pro Gly Lys Gly Leu Glu Tyr
        35                  40                  45

Val Ala Gly Ile Arg Ser Asp Gly Ser Tyr Pro Ser Tyr Gly Ala Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Phe
                85                  90                  95

Cys Ala Lys Val Ala Gly Gly His Cys Asp Trp Gly Ala Gly Cys Ile
            100                 105                 110

Asp Thr Trp Gly His Gly Thr Glu Val Ile Val Ser Ser
        115                 120                 125
```

```
<210> SEQ ID NO 59
<211> LENGTH: 125
<212> TYPE: PRT
<213> ORGANISM: Gallus gallus

<400> SEQUENCE: 59

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Thr Phe Ser Ser
            20                  25                  30

His Gly Met His Trp Val Arg Gln Ala Pro Gly Lys Gly Leu Glu Trp
        35                  40                  45

Val Ala Gly Ile Asp Asp Gly Gly Ser Tyr Arg Asn Tyr Gly Ala Ala
    50                  55                  60

Val Lys Gly Arg Ala Thr Ile Ser Arg Asp Asp Gly Glu Ser Thr Val
65                  70                  75                  80

Arg Leu Gln Met Asn Asn Leu Arg Ala Glu Asp Thr Gly Ile Tyr Phe
                85                  90                  95

Cys Val Lys Ser Ala Tyr Gly Cys Cys Gly Thr Asp Ala Tyr Ser Leu
            100                 105                 110

Asp Ala Trp Gly His Gly Thr Glu Val Ile Val Ser Ser
        115                 120                 125

<210> SEQ ID NO 60
<211> LENGTH: 126
<212> TYPE: PRT
<213> ORGANISM: Gallus gallus

<400> SEQUENCE: 60

Ala Ala Val Thr Leu Asp Glu Ser Gly Gly Gly Leu Gln Thr Pro Gly
1               5                   10                  15

Gly Ala Leu Ser Leu Val Cys Arg Ala Ser Gly Phe Ser Phe Ser Asp
            20                  25                  30

Arg Gly Met His Trp Val Arg Gln Ala Pro Gly Lys Gly Leu Glu Trp
        35                  40                  45

Val Gly Val Ile Asn Gly Gly Gly Tyr Glu Glu Tyr Tyr Gly Thr Ala
    50                  55                  60

Val Lys Gly Arg Ala Thr Ile Ser Arg Asp Asn Gly Gln Ser Thr Val
65                  70                  75                  80

Arg Leu His Leu Asn Asn Leu Arg Thr Glu Asp Ser Gly Ile Tyr Tyr
                85                  90                  95

Cys Ala Arg Ala Ala Gly Gly Trp Phe Gly Trp Ser Ser Ala Gly Ser
            100                 105                 110

Ile Asp Ala Trp Gly His Gly Thr Glu Val Ile Val Ser Ser
        115                 120                 125

<210> SEQ ID NO 61
<211> LENGTH: 125
<212> TYPE: PRT
<213> ORGANISM: Gallus gallus

<400> SEQUENCE: 61

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Thr Phe Ser Ser
            20                  25                  30

Tyr Val Leu Gln Trp Val Arg Gln Ala Pro Gly Lys Gly Leu Glu Trp
```

```
            35                  40                  45
Val Ala Gly Ile Asp Asp Ala Gly Ser Tyr Arg Asn Tyr Gly Ala Ala
    50                  55                  60

Val Lys Gly Arg Ala Thr Ile Ser Arg Asp Asn Gly Gln Ser Thr Met
65                  70                  75                  80

Arg Leu Gln Leu Asn Asn Leu Arg Ala Glu Asp Thr Gly Ile Tyr Phe
                85                  90                  95

Cys Ala Lys Ser Ala Tyr Gly Cys Cys Gly Thr Asp Ala Tyr Ser Leu
                100                 105                 110

Asp Ala Trp Gly His Gly Thr Glu Val Ile Val Ser Ser
            115                 120                 125

<210> SEQ ID NO 62
<211> LENGTH: 137
<212> TYPE: PRT
<213> ORGANISM: Gallus gallus

<400> SEQUENCE: 62

Ala Ala Val Thr Leu Asp Glu Ser Gly Gly Gly Leu Gln Thr Pro Gly
1               5                   10                  15

Gly Gly Leu Ser Leu Val Cys Lys Ala Ser Gly Phe Thr Phe Ser Ser
                20                  25                  30

His Gly Met Gly Trp Val Arg Gln Ala Pro Gly Lys Gly Leu Glu Trp
            35                  40                  45

Val Ala Asp Ile Asp Arg Thr Gly Ser Trp Thr Gly Tyr Gly Ala Ala
    50                  55                  60

Val Lys Gly Arg Ala Thr Ile Ser Arg Asp Asp Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Arg Ser Ala Ser Gly Gly Tyr Cys Trp Phe Thr Asp Arg Ser
                100                 105                 110

Ile Leu Thr Cys Asn Gly Gly Gly Thr Ala Ile Asp Ala Trp Gly
            115                 120                 125

His Gly Thr Glu Val Ile Val Ser Ser
    130                 135

<210> SEQ ID NO 63
<211> LENGTH: 137
<212> TYPE: PRT
<213> ORGANISM: Gallus gallus

<400> SEQUENCE: 63

Ala Ala Val Thr Leu Asp Glu Ser Gly Gly Gly Leu Gln Thr Pro Gly
1               5                   10                  15

Gly Thr Leu Ser Leu Val Cys Lys Ala Ser Gly Phe Thr Phe Ser Asp
                20                  25                  30

Tyr Ala Met Gly Trp Val Arg Gln Ala Pro Gly Lys Gly Leu Glu Trp
            35                  40                  45

Val Ala Asp Ile Asp Arg Thr Ser Ser Trp Thr Ser Tyr Gly Ser Gly
    50                  55                  60

Val Glu Gly Arg Ala Thr Ile Ser Arg Asp Asn Gly Gln Ser Thr Leu
65                  70                  75                  80

Arg Leu Gln Leu Asn Asn Leu Arg Ala Glu Asp Thr Gly Thr Tyr Phe
                85                  90                  95

Cys Ala Lys Ser Ala Gly Ser Gly Tyr Cys Gly Trp Asn Pro Ser Tyr
```

-continued

```
                100                 105                 110

Asn Phe Asn Cys Gly Ala Tyr Ile Ala Ala Thr Val Asp Ala Trp Gly
        115                 120                 125

His Gly Thr Glu Val Ile Val Ser Ser
    130                 135

<210> SEQ ID NO 64
<211> LENGTH: 137
<212> TYPE: PRT
<213> ORGANISM: Gallus gallus

<400> SEQUENCE: 64

Ala Ala Val Thr Leu Asp Glu Ser Gly Gly Gly Leu Gln Thr Pro Gly
1               5                   10                  15

Gly Gly Leu Ser Leu Val Cys Lys Ala Ser Gly Phe Asp Phe Thr Ser
            20                  25                  30

His Gly Met Gly Trp Val Arg Gln Ala Pro Gly Lys Gly Leu Glu Trp
        35                  40                  45

Val Ala Asp Ile Asp Arg Thr Gly Ser Trp Thr Ala Tyr Gly Ala Ala
    50                  55                  60

Val Lys Gly Arg Ala Thr Ile Ser Arg Asp Asp Gly Gln Ser Thr Val
65                  70                  75                  80

Arg Leu Gln Leu Ser Ser Leu Arg Ala Glu Asp Thr Gly Thr Tyr Tyr
                85                  90                  95

Cys Ala Arg Ser Ala Ser Gly Gly Tyr Cys Trp Phe Ser Asp Arg Ser
            100                 105                 110

Ile Leu Thr Cys Asn Gly Gly Gly Ser Ala Ile Asp Ala Trp Gly
        115                 120                 125

His Gly Thr Glu Val Ile Val Ser Ser
    130                 135

<210> SEQ ID NO 65
<211> LENGTH: 137
<212> TYPE: PRT
<213> ORGANISM: Gallus gallus

<400> SEQUENCE: 65

Ala Ala Val Thr Leu Asp Glu Ser Gly Gly Gly Leu Gln Thr Pro Gly
1               5                   10                  15

Gly Gly Leu Ser Leu Val Cys Lys Ala Ser Gly Phe Asp Phe Thr Ser
            20                  25                  30

His Gly Met Gly Trp Val Arg Gln Ala Pro Gly Lys Gly Leu Glu Trp
        35                  40                  45

Val Ala Asp Ile Asp Arg Thr Gly Ser Trp Thr Ala Tyr Gly Ala Ala
    50                  55                  60

Val Lys Gly Arg Ala Thr Ile Ser Arg Asp Asp Gly Gln Ser Thr Val
65                  70                  75                  80

Arg Leu Gln Leu Ser Ser Leu Arg Ala Glu Asp Thr Gly Thr Tyr Tyr
                85                  90                  95

Cys Ala Arg Ser Ala Ser Gly Gly Tyr Cys Trp Phe Ser Asp Arg Ser
            100                 105                 110

Ile Leu Thr Cys Asn Gly Gly Gly Ser Ala Ile Asp Ala Trp Gly
        115                 120                 125

His Gly Thr Glu Val Ile Val Ser Ser
    130                 135
```

-continued

```
<210> SEQ ID NO 66
<211> LENGTH: 137
<212> TYPE: PRT
<213> ORGANISM: Gallus gallus

<400> SEQUENCE: 66

Ala Ala Val Thr Leu Asp Glu Ser Gly Gly Gly Leu Gln Thr Pro Gly
1               5                   10                  15

Gly Gly Leu Ser Leu Val Cys Lys Thr Ser Gly Phe Asp Phe Thr Ser
            20                  25                  30

His Gly Met Gly Trp Val Arg Gln Ala Pro Gly Lys Gly Leu Glu Trp
        35                  40                  45

Val Ala Asp Ile Asp Arg Thr Gly Ser Trp Thr Ala Tyr Gly Ala Ala
        50                  55                  60

Val Lys Gly Arg Ala Thr Ile Ser Arg Gly Asp Gly Gln Ser Thr Val
65                  70                  75                  80

Arg Leu Gln Leu Ser Ser Leu Arg Ala Glu Asp Thr Gly Thr Tyr Tyr
                85                  90                  95

Cys Ala Arg Ser Ala Ser Gly Gly Tyr Cys Trp Phe Ser Asp Arg Ser
                100                 105                 110

Ile Leu Thr Cys Asn Gly Gly Gly Ser Ala Ile Asp Ala Trp Gly
            115                 120                 125

His Gly Thr Glu Val Ile Val Ser Ser
        130                 135

<210> SEQ ID NO 67
<211> LENGTH: 122
<212> TYPE: PRT
<213> ORGANISM: Gallus gallus

<400> SEQUENCE: 67

Ala Ala Val Thr Leu Asp Glu Ser Gly Gly Gly Leu Gln Thr Pro Gly
1               5                   10                  15

Arg Thr Leu Ser Leu Val Cys Lys Ala Ser Gly Phe Thr Phe Ser Ser
            20                  25                  30

Tyr Ala Met Tyr Trp Val Arg Gln Ala Pro Gly Lys Gly Leu Glu Phe
        35                  40                  45

Val Ala Gly Ile Asp Ser Gly Ser Gly Thr Gly Tyr Ala Pro Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Val Arg Asp Gly Ser Tyr Gly Cys Gly Ser Gly Cys Leu Asp Ala Trp
                100                 105                 110

Gly His Gly Thr Glu Val Ile Val Ser Ser
            115                 120

<210> SEQ ID NO 68
<211> LENGTH: 128
<212> TYPE: PRT
<213> ORGANISM: Gallus gallus

<400> SEQUENCE: 68

Ala Ala Val Thr Leu Asp Glu Ser Gly Gly Gly Leu Gln Thr Pro Gly
1               5                   10                  15

Gly Gly Leu Ser Leu Val Cys Lys Ala Ser Gly Phe Thr Phe Ser Ser
            20                  25                  30
```

```
Phe Tyr Asp Met Phe Trp Leu Arg Gln Ala Pro Gly Lys Gly Leu Glu
        35                  40                  45

Phe Val Ala Gly Ile Asp Ile Gly Ser Gly Thr Tyr Tyr Ala Pro Ala
        50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Ala Val Gly Ser Cys Thr Tyr Gly Asn Gly Cys Gly Val
                100                 105                 110

Gly Gly Ile Asp Ala Trp Gly His Gly Thr Glu Val Ile Val Ser Ser
        115                 120                 125

<210> SEQ ID NO 69
<211> LENGTH: 128
<212> TYPE: PRT
<213> ORGANISM: Gallus gallus

<400> SEQUENCE: 69

Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Asp Phe Ser Ser
                20                  25                  30

Tyr Ala Met Asn Trp Val Arg Gln Ala Pro Gly Lys Gly Leu Glu Trp
        35                  40                  45

Val Ala Gly Ile Gly Asn Ser Gly Ser Ser Thr Tyr Tyr Ala Pro Ala
        50                  55                  60

Val Lys Gly Arg Val Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Asn Thr Val Gly Trp Ala Ala Val Leu Leu Val Asp Ala
                100                 105                 110

Gly Leu Ile Asp Ala Trp Gly His Gly Thr Glu Val Ile Val Ser Ser
        115                 120                 125

<210> SEQ ID NO 70
<211> LENGTH: 128
<212> TYPE: PRT
<213> ORGANISM: Gallus gallus

<400> SEQUENCE: 70

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Asp Phe Arg Ser
                20                  25                  30

Tyr Glu Met Gln Trp Val Arg Gln Ala Pro Gly Lys Gly Leu Glu Phe
        35                  40                  45

Val Ala Glu Ile Ser Gly Ser Gly Ser Thr Pro Lys Tyr Gly Glu Ala
        50                  55                  60

Val Lys Gly Arg Ala Thr Ile Ser Arg Asp Asn Gly Gln Ser Thr Leu
65                  70                  75                  80

Arg Leu Gln Leu Asn Asn Leu Arg Ala Glu Asp Thr Gly Thr Tyr Tyr
                85                  90                  95

Cys Ala Lys Asn Ala Asp Phe Gly Tyr Ser Trp Ser Trp Thr Tyr Thr
                100                 105                 110
```

-continued

```
Ala Ser Ile Asp Ala Trp Gly His Gly Thr Glu Val Ile Val Ser Ser
        115                 120                 125

<210> SEQ ID NO 71
<211> LENGTH: 138
<212> TYPE: PRT
<213> ORGANISM: Gallus gallus

<400> SEQUENCE: 71

Ala Ala Val Thr Leu Asp Glu Ser Gly Gly Gly Leu Gln Thr Pro Gly
1               5                   10                  15

Arg Ala Leu Ser Leu Val Cys Lys Ala Ser Gly Phe Thr Phe Ser Asp
            20                  25                  30

Tyr Ala Met Gly Trp Val Arg Gln Ala Pro Gly Lys Gly Leu Glu Phe
        35                  40                  45

Val Ala Asp Ile Asp Lys Thr Gly Ser Leu Thr Ala Tyr Gly Ala Ala
    50                  55                  60

Val Gln Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Phe
                85                  90                  95

Cys Ala Lys Ala Ala Val Ser Gly His Cys Tyr Ile Gly Thr Ala Tyr
            100                 105                 110

Pro Gly Leu Thr Cys Gly Ala Tyr Thr Ala Ile Thr Ile Asp Ser Trp
        115                 120                 125

Gly His Gly Thr Glu Val Ile Val Ser Ser
    130                 135

<210> SEQ ID NO 72
<211> LENGTH: 136
<212> TYPE: PRT
<213> ORGANISM: Gallus gallus

<400> SEQUENCE: 72

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Ser Phe Ser Asp
            20                  25                  30

Tyr Gly Met Gly Trp Val Arg Gln Ala Pro Gly Lys Gly Leu Glu Phe
        35                  40                  45

Val Ala Asp Ile Asp Lys Thr Gly Ser Trp Thr Ala Tyr Gly Ala Ala
    50                  55                  60

Val Gln Gly Arg Ala Thr Ile Ser Arg Asp Asp Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Ala Ala Val Ser Gly His Cys Tyr Ile Gly Ala Ser Gly
            100                 105                 110

Leu Thr Cys Gly Ala Tyr Thr Ala Ile Thr Ile Asp Ser Trp Gly His
        115                 120                 125

Gly Thr Glu Val Ile Val Ser Ser
    130                 135

<210> SEQ ID NO 73
<211> LENGTH: 119
<212> TYPE: PRT
<213> ORGANISM: Gallus gallus
```

<400> SEQUENCE: 73

Ala Ala Val Thr Leu Asp Glu Ser Gly Gly Gly Leu Gln Thr Pro Gly
1               5                   10                  15

Gly Ala Leu Ser Leu Val Cys Lys Ala Ser Gly Phe Ile Phe Ser Asp
                20                  25                  30

Arg Gly Met Leu Trp Val Arg Gln Ala Pro Gly Lys Gly Leu Glu Trp
            35                  40                  45

Val Ala Gly Ile Asp Asp Asp Gly Gly Phe Thr Asp Tyr Gly Ala Ala
        50                  55                  60

Val Lys Gly Arg Ala Thr Ile Ser Arg Asp Asn Gly Gln Ser Thr Val
65                  70                  75                  80

Arg Leu Gln Leu Ile Asn Leu Arg Ala Glu Asp Thr Gly Thr Tyr Tyr
                85                  90                  95

Cys Ala Arg Gly Ala Tyr Gly Ala Ser Ile Asp Ala Trp Gly His Gly
            100                 105                 110

Thr Glu Val Ile Val Ser Ser
            115

<210> SEQ ID NO 74
<211> LENGTH: 128
<212> TYPE: PRT
<213> ORGANISM: Gallus gallus

<400> SEQUENCE: 74

Ala Ala Val Thr Leu Asp Glu Ser Gly Gly Gly Leu Gln Thr Pro Gly
1               5                   10                  15

Gly Ala Leu Ser Leu Val Cys Lys Gly Ser Gly Phe Thr Phe Ser Asn
                20                  25                  30

Phe Asn Ile Phe Trp Val Arg Gln Ala Pro Gly Lys Gly Leu Glu Tyr
            35                  40                  45

Val Ala Glu Ile Ser Gly Thr Gly Ser Gly Thr Gly Tyr Gly Ser Ala
        50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Arg Ser Gly Phe Ser Gly Gly Val Leu Val Val Gly Asp Ala
            100                 105                 110

Ala Tyr Ile Asp Ala Trp Gly His Gly Thr Glu Val Ile Val Ser Ser
            115                 120                 125

<210> SEQ ID NO 75
<211> LENGTH: 116
<212> TYPE: PRT
<213> ORGANISM: Gallus gallus

<400> SEQUENCE: 75

Ala Leu Thr Gln Pro Ala Ser Val Ser Ala Asn Pro Gly Glu Thr Val
1               5                   10                  15

Glu Ile Thr Cys Ser Gly Ser Gly Gly Ser Gly Ile Tyr Gly Trp Tyr
                20                  25                  30

Gln Gln Lys Ser Pro Gly Ser Ala Pro Val Thr Val Ile Tyr Arg Asn
            35                  40                  45

Asn Gln Arg Pro Ser Asp Ile Pro Ser Arg Phe Ser Gly Ser Thr Ser
        50                  55                  60

```
Gly Ser Thr Ala Thr Leu Thr Ile Thr Gly Val Gln Ala Glu Asp Glu
65                  70                  75                  80

Ala Val Tyr Phe Cys Gly Thr Arg Asp Ser Ser Arg Ser Arg Asp Ser
                85                  90                  95

Ser Thr Asp Tyr Val Gly Tyr Val Gly Ile Phe Gly Ala Gly Thr Thr
            100                 105                 110

Leu Thr Val Leu
        115

<210> SEQ ID NO 76
<211> LENGTH: 106
<212> TYPE: PRT
<213> ORGANISM: Gallus gallus

<400> SEQUENCE: 76

Ala Leu Thr Gln Pro Ala Ser Val Ser Ala Asn Leu Gly Gly Thr Val
1               5                   10                  15

Glu Ile Thr Cys Ser Gly Gly Ser Ile Ser Tyr Tyr Tyr Gly Trp Tyr
                20                  25                  30

Gln Gln Lys Ser Pro Gly Ser Ala Pro Val Thr Val Ile Tyr Ser Asn
            35                  40                  45

Asp Gln Arg Pro Ser Asp Ile Pro Ser Arg Phe Ser Gly Ser Ala Ser
        50                  55                  60

Asp Ser Thr Gly Thr Leu Thr Ile Thr Gly Val Gln Ala Asp Asp Glu
65                  70                  75                  80

Ala Val Tyr Phe Cys Gly Ser Gly Asp Gly Asn Ala Gly His Ser Thr
                85                  90                  95

Phe Gly Ala Gly Thr Thr Leu Thr Val Leu
            100                 105

<210> SEQ ID NO 77
<211> LENGTH: 106
<212> TYPE: PRT
<213> ORGANISM: Gallus gallus

<400> SEQUENCE: 77

Ala Leu Thr Gln Pro Ala Ser Val Ser Ala Asn Pro Gly Glu Thr Val
1               5                   10                  15

Lys Ile Thr Cys Ser Gly Ser Gly Gly Thr Tyr Ala Trp Tyr Gln Gln
                20                  25                  30

Lys Ser Pro Gly Ser Ala Pro Val Thr Leu Ile Tyr His Asp Asn Asn
            35                  40                  45

Arg Pro Ser Asp Ile Pro Ser Arg Phe Ser Gly Ser Ala Ser Gly Ser
        50                  55                  60

Thr Ala Thr Leu Thr Ile Thr Gly Val Gln Ala Glu Asp Glu Ala Val
65                  70                  75                  80

Tyr Tyr Cys Gly Ser Arg Asp Gly Ser Tyr Val Gly Tyr Val Gly Val
                85                  90                  95

Phe Gly Ala Gly Thr Thr Leu Thr Val Leu
            100                 105

<210> SEQ ID NO 78
<211> LENGTH: 106
<212> TYPE: PRT
<213> ORGANISM: Gallus gallus

<400> SEQUENCE: 78

Ala Leu Thr Gln Pro Ala Ser Val Ser Ala Asn Pro Gly Glu Thr Val
```

```
1               5                    10                   15

Lys Ile Thr Cys Ser Gly Ser Gly Gly Thr Tyr Ala Trp Tyr Gln His
            20                  25                  30

Arg Ser Pro Gly Ser Ala Pro Val Thr Leu Ile Tyr His Asp Asn Asn
        35                  40                  45

Arg Pro Ser Asp Ile Pro Ser Arg Phe Ser Gly Ser Ala Ser Gly Ser
    50                  55                  60

Thr Ala Thr Leu Thr Ile Thr Gly Val Gln Ala Glu Asp Glu Ala Val
65                  70                  75                  80

Tyr Tyr Cys Gly Ser Arg Asp Gly Ser Tyr Val Gly Tyr Val Gly Val
            85                  90                  95

Phe Gly Ala Gly Thr Thr Leu Thr Val Leu
            100                 105

<210> SEQ ID NO 79
<211> LENGTH: 106
<212> TYPE: PRT
<213> ORGANISM: Gallus gallus

<400> SEQUENCE: 79

Ala Leu Ile Gln Pro Ser Ser Leu Ser Ala Asn Pro Gly Glu Thr Val
1               5                    10                   15

Glu Ile Thr Cys Ser Gly Gly Ser Ser Ser Tyr Tyr Tyr Gly Trp Tyr
            20                  25                  30

Gln Gln Lys Ser Pro Gly Ser Ala Pro Val Thr Val Ile Tyr Ser Ser
        35                  40                  45

Asp Lys Arg Pro Ser Asp Ile Pro Ser Arg Phe Ser Gly Ser Ala Ser
    50                  55                  60

Gly Ser Thr Ala Thr Leu Thr Ile Thr Gly Val Gln Ala Asp Asp Glu
65                  70                  75                  80

Ala Val Tyr Phe Cys Gly Ser Gly Asp Gly Asn Ala Gly His Ser Thr
            85                  90                  95

Phe Gly Ala Gly Thr Thr Leu Thr Val Leu
            100                 105

<210> SEQ ID NO 80
<211> LENGTH: 106
<212> TYPE: PRT
<213> ORGANISM: Gallus gallus

<400> SEQUENCE: 80

Ala Leu Thr Gln Pro Phe Ser Val Ser Ala Asn Pro Gly Glu Thr Val
1               5                    10                   15

Glu Ile Thr Cys Ser Gly Gly Ser Ser Ser Tyr Tyr Tyr Gly Trp Tyr
            20                  25                  30

Gln Gln Lys Ser Pro Gly Ser Thr Pro Val Thr Val Ile Tyr Ser Ser
        35                  40                  45

Asp Lys Arg Pro Ser Asp Ile Pro Ser Arg Phe Ser Gly Ser Ala Ser
    50                  55                  60

Gly Ser Thr Ala Thr Leu Thr Ile Thr Gly Val Gln Ala Asp Asp Glu
65                  70                  75                  80

Ala Val Tyr Phe Cys Gly Asn Gly Asp Gly Asn Ala Gly His Ser Thr
            85                  90                  95

Phe Gly Ala Gly Thr Thr Leu Thr Val Leu
            100                 105
```

<210> SEQ ID NO 81
<211> LENGTH: 106
<212> TYPE: PRT
<213> ORGANISM: Gallus gallus

<400> SEQUENCE: 81

Ala Leu Thr Gln Pro Ser Ser Val Ser Ala Asn Pro Gly Glu Thr Val
1               5                   10                  15

Glu Ile Thr Cys Ser Gly Gly Ser Ser Tyr Tyr Tyr Gly Trp Tyr
            20                  25                  30

Gln Gln Lys Ser Pro Gly Ser Thr Pro Val Thr Val Ile Tyr Ser Ser
        35                  40                  45

Asp Lys Arg Pro Ser Asp Ile Pro Ser Arg Phe Ser Gly Ser Ala Ser
        50                  55                  60

Gly Ser Thr Ala Thr Leu Thr Ile Thr Gly Val Gln Ala Asp Asp Glu
65                  70                  75                  80

Ala Val Tyr Phe Cys Gly Asn Gly Asp Gly Asn Ala Gly His Ser Thr
                85                  90                  95

Phe Gly Ala Gly Thr Thr Leu Thr Val Leu
                100                 105

<210> SEQ ID NO 82
<211> LENGTH: 116
<212> TYPE: PRT
<213> ORGANISM: Gallus gallus

<400> SEQUENCE: 82

Ala Leu Ser Gln Pro Ala Ser Val Ser Ala Asn Pro Gly Glu Thr Val
1               5                   10                  15

Lys Ile Thr Cys Ser Gly Ser Gly Gly Ser Gly Ile Tyr Gly Trp Tyr
            20                  25                  30

Gln Gln Lys Ser Pro Gly Ser Ala Pro Val Thr Val Ile Tyr Ser Asn
        35                  40                  45

Asn Lys Arg Pro Ser Asp Ile Pro Ser Arg Phe Ser Gly Ser Ala Ser
        50                  55                  60

Asp Ser Thr Ala Thr Leu Thr Ile Thr Gly Val Gln Val Glu Asp Glu
65                  70                  75                  80

Ala Val Tyr Phe Cys Gly Thr Arg Gly Ser Ser Arg Ser Arg Asp Ser
                85                  90                  95

Ser Ala Asp Tyr Val Gly Tyr Val Ser Ile Phe Gly Ala Gly Thr Thr
                100                 105                 110

Leu Thr Val Leu
        115

<210> SEQ ID NO 83
<211> LENGTH: 106
<212> TYPE: PRT
<213> ORGANISM: Gallus gallus

<400> SEQUENCE: 83

Ala Leu Thr Gln Pro Ser Ser Val Ser Ala Asn Pro Gly Glu Thr Ile
1               5                   10                  15

Glu Ile Thr Cys Ser Gly Gly Ser Ser Tyr Tyr Tyr Gly Trp Tyr
            20                  25                  30

Gln Gln Lys Ser Pro Gly Ser Ala Pro Val Thr Val Ile Tyr Ser Ser
        35                  40                  45

Asn Gln Arg Pro Ser Asp Ile Pro Ser Arg Phe Ser Gly Ser Ala Ser
        50                  55                  60

-continued

Gly Ser Thr Ala Thr Leu Ala Ile Thr Gly Ala Gln Ala Asp Asp Glu
65                  70                  75                  80

Ala Val Tyr Phe Cys Gly Ser Gly Asp Gly Asn Ala Gly His Ser Thr
                85                  90                  95

Phe Gly Ala Gly Thr Thr Leu Thr Val Leu
            100                 105

<210> SEQ ID NO 84
<211> LENGTH: 106
<212> TYPE: PRT
<213> ORGANISM: Gallus gallus

<400> SEQUENCE: 84

Ala Leu Thr Gln Pro Ser Ser Val Ser Ala Asn Pro Gly Glu Thr Val
1               5                   10                  15

Glu Ile Ser Cys Ser Gly Gly Ser Ser Arg Tyr Tyr Tyr Gly Trp Tyr
                20                  25                  30

Gln Gln Lys Ser Pro Gly Ser Ala Pro Val Thr Val Ile Tyr Ser Asn
            35                  40                  45

Asp Lys Arg Pro Ser Asp Ile Pro Ser Arg Phe Ser Gly Ser Thr Ser
        50                  55                  60

Gly Ser Thr Ser Thr Leu Thr Ile Thr Gly Val Gln Ala Asp Asp Glu
65                  70                  75                  80

Ala Val Tyr Phe Cys Gly Ser Gly Asp Gly Asn Ala Gly His Ser Thr
                85                  90                  95

Phe Gly Ala Gly Thr Thr Leu Thr Val Leu
            100                 105

<210> SEQ ID NO 85
<211> LENGTH: 116
<212> TYPE: PRT
<213> ORGANISM: Gallus gallus

<400> SEQUENCE: 85

Glu Leu Ser Gln Pro Ala Ser Val Ser Ala Asn Pro Gly Glu Thr Val
1               5                   10                  15

Lys Ile Thr Cys Ser Gly Ser Gly Gly Ser Gly Ile Tyr Gly Trp Tyr
                20                  25                  30

Gln Gln Lys Ser Pro Asp Ser Ala Leu Val Thr Val Ile Tyr Ser Asn
            35                  40                  45

Asn Lys Arg Pro Ser Asp Ile Pro Ser Arg Phe Ser Gly Ser Ala Ser
        50                  55                  60

Asp Ser Ile Ala Thr Leu Thr Ile Thr Gly Val Gln Val Glu Asp Glu
65                  70                  75                  80

Ala Val Tyr Phe Cys Gly Thr Arg Gly Ser Ser Arg Ser Ser Glu Ser
                85                  90                  95

Ser Ala Asp Tyr Val Gly Tyr Val Val Ile Phe Gly Ala Gly Thr Thr
            100                 105                 110

Leu Thr Val Leu
        115

<210> SEQ ID NO 86
<211> LENGTH: 106
<212> TYPE: PRT
<213> ORGANISM: Gallus gallus

<400> SEQUENCE: 86

-continued

```
Ala Leu Thr Gln Pro Ala Ser Val Ser Ala Asn Leu Gly Gly Thr Val
1               5                   10                  15

Glu Ile Thr Cys Ser Gly Asp Asp Arg Gly Tyr Gly Tyr Gly Trp Tyr
                20                  25                  30

Gln Gln Lys Ser Pro Gly Ser Ala Pro Val Thr Val Ile Tyr Arg Asn
            35                  40                  45

Asp Lys Arg Pro Ser Asp Ile Pro Ser Arg Phe Ser Gly Ser Leu Ser
        50                  55                  60

Gly Ser Thr Gly Thr Leu Thr Ile Thr Gly Val Gln Ile Asp Asp Glu
65                  70                  75                  80

Ala Val Tyr Phe Cys Gly Ser Trp Asp Ser Ser Ser Thr Ala Gly Ile
                85                  90                  95

Phe Gly Ala Gly Thr Thr Leu Thr Val Leu
            100                 105

<210> SEQ ID NO 87
<211> LENGTH: 105
<212> TYPE: PRT
<213> ORGANISM: Gallus gallus

<400> SEQUENCE: 87

Ala Leu Thr Gln Gln Pro Ala Ser Val Ser Ala Ser Pro Gly Glu Thr
1               5                   10                  15

Val Lys Ile Thr Cys Ser Gly Gly Ser Tyr Ser Ser Tyr Tyr Gly Trp
                20                  25                  30

Tyr Gln Gln Lys Ser Pro Gly Ser Ala Pro Val Thr Leu Ile Tyr Ser
            35                  40                  45

Asn Asp Lys Arg Pro Ser Asp Ile Pro Ser Arg Phe Ser Gly Ser Lys
        50                  55                  60

Ser Gly Ser Thr Gly Thr Leu Ile Ile Thr Gly Val Gln Ala Glu Asp
65                  70                  75                  80

Glu Ala Val Tyr Phe Cys Gly Ser Ser Asp Ser Ser Ser Gly Ile Phe
                85                  90                  95

Gly Ala Gly Thr Thr Leu Thr Val Leu
            100                 105

<210> SEQ ID NO 88
<211> LENGTH: 104
<212> TYPE: PRT
<213> ORGANISM: Gallus gallus

<400> SEQUENCE: 88

Ala Leu Thr Gln Pro Ala Ser Val Ser Ala Asn Leu Gly Gly Thr Val
1               5                   10                  15

Glu Ile Thr Cys Ser Gly Gly Ser Ser Ser Tyr Gly Tyr Ser Trp His
                20                  25                  30

Gln Gln Lys Ser Pro Gly Ser Ala Pro Val Thr Val Ile Tyr Val Asn
            35                  40                  45

Asp Arg Arg Pro Ser Asp Ile Pro Ser Arg Phe Ser Gly Ser Thr Ser
        50                  55                  60

Gly Pro Thr Gly Thr Leu Ile Ile Thr Gly Val Arg Ala Asp Asp Glu
65                  70                  75                  80

Ala Val Tyr Phe Cys Gly Ser Tyr Asp Thr Asn Thr Tyr Thr Phe Gly
                85                  90                  95

Ala Gly Thr Thr Leu Thr Val Leu
            100
```

-continued

<210> SEQ ID NO 89
<211> LENGTH: 106
<212> TYPE: PRT
<213> ORGANISM: Gallus gallus

<400> SEQUENCE: 89

Ala Leu Ile Gln Pro Ala Ser Val Ser Val Asn Leu Gly Gly Thr Val
1               5                   10                  15

Glu Ile Thr Cys Ser Gly Gly His Ser Gly Phe Gly Tyr Gly Trp Tyr
            20                  25                  30

Gln Gln Lys Ser Pro Gly Arg Ala Pro Val Thr Val Ile Tyr Ser Ser
        35                  40                  45

Asp Lys Arg Pro Ser Asn Ile Pro Ser Arg Phe Ser Gly Ser Arg Ser
    50                  55                  60

Gly Ser Thr Gly Thr Leu Val Ile Thr Gly Val Gln Ala Glu Asp Glu
65                  70                  75                  80

Ala Val Tyr Phe Cys Gly Ser Ala Asp Ser Ser Ser Tyr Ile Asp Ile
                85                  90                  95

Phe Gly Thr Gly Thr Thr Leu Thr Val Leu
            100                 105

<210> SEQ ID NO 90
<211> LENGTH: 102
<212> TYPE: PRT
<213> ORGANISM: Gallus gallus

<400> SEQUENCE: 90

Ala Leu Thr Gln Pro Ala Ser Val Ser Ala Asn Pro Gly Glu Thr Val
1               5                   10                  15

Glu Ile Thr Cys Ser Gly Gly Arg Tyr Ser Tyr Gly Trp Phe Gln Gln
            20                  25                  30

Lys Ser Pro Gly Ser Ala Pro Val Thr Val Ile Tyr Gln Asn Tyr Tyr
        35                  40                  45

Arg Pro Ser Asp Ile Pro Ser Arg Phe Ser Gly Ser Ala Ser Gly Ser
    50                  55                  60

Thr Ala Thr Leu Thr Ile Thr Gly Val Gln Val Glu Asp Glu Gly Val
65                  70                  75                  80

Tyr Tyr Cys Gly Ala Tyr Asp Ser Lys Ala Gly Met Phe Gly Ala Gly
                85                  90                  95

Thr Thr Leu Thr Val Leu
            100

<210> SEQ ID NO 91
<211> LENGTH: 105
<212> TYPE: PRT
<213> ORGANISM: Gallus gallus

<400> SEQUENCE: 91

Ala Leu Thr Gln Pro Ala Ser Val Ser Ala Asp Leu Gly Gly Thr Val
1               5                   10                  15

Glu Ile Thr Cys Ser Gly Gly Thr Ser Asp Tyr Gly Tyr Gly Trp Tyr
            20                  25                  30

Gln Gln Lys Ser Pro Gly Ser Ala Leu Val Thr Leu Ile Tyr Gln Asn
        35                  40                  45

Asn Tyr Arg Pro Ser Asp Ile Pro Ser Arg Phe Ser Gly Ser Thr Ser
    50                  55                  60

Gly Ser Thr Ala Thr Leu Thr Val Thr Gly Val Arg Val Glu Asp Glu

-continued

```
65                    70                    75                    80
Ala Val Tyr Phe Cys Gly Thr Arg Gly Ser Ser Thr Pro Ala Ile Phe
                 85                    90                    95

Gly Ala Gly Thr Thr Leu Thr Val Leu
             100                   105

<210> SEQ ID NO 92
<211> LENGTH: 105
<212> TYPE: PRT
<213> ORGANISM: Gallus gallus

<400> SEQUENCE: 92

Ala Leu Thr Gln Pro Ser Ser Val Ser Val Asn Leu Gly Gly Thr Val
1               5                   10                  15

Glu Ile Thr Cys Ser Gly Gly Asn Ser Gly Tyr Gly Tyr Ser Trp His
             20                  25                  30

Gln Gln Lys Ala Pro Gly Ser Ala Pro Val Thr Leu Ile Tyr Phe Asn
         35                  40                  45

Asp Lys Arg Pro Ser Asp Ile Pro Ser Arg Phe Ser Gly Ser Thr Ser
     50                  55                  60

Gly Ser Thr Gly Thr Leu Thr Ile Thr Gly Val Arg Ala Glu Asp Glu
65                  70                  75                  80

Ala Val Tyr Tyr Cys Gly Ser Pro Asp Phe Ile Asn Thr Pro Val Phe
                 85                  90                  95

Gly Ala Gly Thr Thr Leu Thr Val Leu
             100                   105

<210> SEQ ID NO 93
<211> LENGTH: 105
<212> TYPE: PRT
<213> ORGANISM: Gallus gallus

<400> SEQUENCE: 93

Ala Leu Thr Gln Pro Ala Ser Val Ser Ala Asn Leu Gly Gly Thr Val
1               5                   10                  15

Glu Ile Thr Cys Ser Gly Gly Asn Ser Gly Tyr Gly Tyr Ser Trp His
             20                  25                  30

Gln Gln Lys Ala Pro Gly Ser Ala Pro Val Thr Leu Ile Tyr Phe Asn
         35                  40                  45

Asp Lys Arg Pro Ser Asp Ile Pro Ser Arg Phe Ser Gly Ser Thr Ser
     50                  55                  60

Gly Ser Thr Gly Thr Leu Ile Ile Thr Gly Val Gln Ala Glu Asp Glu
65                  70                  75                  80

Ala Val Tyr Phe Cys Gly Ser Pro Asp Phe Ile Asn Thr Pro Ile Phe
                 85                  90                  95

Gly Ala Gly Thr Thr Leu Thr Val Leu
             100                   105

<210> SEQ ID NO 94
<211> LENGTH: 108
<212> TYPE: PRT
<213> ORGANISM: Gallus gallus

<400> SEQUENCE: 94

Val Leu Thr Gln Gln Pro Ala Ser Val Ser Ala Asn Pro Gly Glu Thr
1               5                   10                  15

Val Met Ile Thr Cys Ser Gly Gly Val Ser Ile Tyr Gly Ser Tyr Tyr
             20                  25                  30
```

```
Tyr Gly Trp Tyr Gln Gln Lys Ser Pro Asp Ser Ala Pro Val Thr Val
    35                  40                  45

Ile Tyr Asn Asn Asn Gln Arg Pro Ser Asp Ile Pro Ser Arg Phe Ser
    50                  55                  60

Gly Ser Ala Ser Gly Ser Thr Asn Thr Leu Ile Ile Thr Gly Val Gln
65                  70                  75                  80

Val Glu Asp Glu Ala Ile Tyr Phe Cys Gly Thr His Glu Asp Thr Thr
                85                  90                  95

Ser Ile Phe Gly Ala Gly Thr Thr Leu Thr Val Leu
            100                 105
```

```
<210> SEQ ID NO 95
<211> LENGTH: 107
<212> TYPE: PRT
<213> ORGANISM: Gallus gallus

<400> SEQUENCE: 95
```

```
Ala Leu Thr Gln Pro Ala Ser Val Ser Ala Asn Leu Gly Gly Thr Val
1               5                   10                  15

Glu Ile Thr Cys Ser Gly Gly Tyr Ser Glu Ala Tyr Gly Trp Tyr Gln
            20                  25                  30

Gln Lys Ser Pro Gly Ser Ala Pro Val Thr Leu Ile Tyr Ser Asn Asp
    35                  40                  45

Lys Arg Pro Ser Asn Ile Pro Ser Arg Phe Ser Gly Ser Thr Ser Gly
    50                  55                  60

Ser Thr Ala Thr Leu Thr Ile Thr Gly Val Arg Ala Glu Asp Glu Ala
65                  70                  75                  80

Val Tyr Leu Cys Gly Ser Phe Asp Ser Ser Tyr Leu Gly Tyr Val Asn
                85                  90                  95

Leu Phe Gly Ala Gly Thr Thr Leu Thr Val Leu
            100                 105
```

```
<210> SEQ ID NO 96
<211> LENGTH: 107
<212> TYPE: PRT
<213> ORGANISM: Gallus gallus

<400> SEQUENCE: 96
```

```
Ala Val Thr Gln Pro Ala Ser Val Ser Ala Asn Pro Gly Glu Thr Val
1               5                   10                  15

Lys Ile Thr Cys Ser Gly Gly Gly Ser Arg Ser Asn Tyr Gly Trp Tyr
            20                  25                  30

Gln Gln Lys Ser Pro Gly Ser Ala Pro Val Thr Leu Ile Tyr Tyr Asn
    35                  40                  45

Asp Lys Arg Pro Ser Asp Ile Pro Ser Arg Phe Ser Gly Ser Lys Ser
    50                  55                  60

Asp Ser Thr Gly Thr Leu Thr Ile Thr Gly Val Gln Ala Glu Asp Glu
65                  70                  75                  80

Ala Val Tyr Phe Cys Gly Asn Trp Asn Phe Asp Ser Ser Tyr Asp Gly
                85                  90                  95

Ile Phe Gly Ala Gly Thr Thr Leu Thr Val Leu
            100                 105
```

```
<210> SEQ ID NO 97
<211> LENGTH: 107
<212> TYPE: PRT
<213> ORGANISM: Gallus gallus
```

-continued

<400> SEQUENCE: 97

Ala Leu Thr Gln Pro Ala Ser Val Ser Ala Asn Leu Gly Glu Thr Val
1               5                   10                  15

Asp Ile Thr Cys Ser Gly Gly Tyr Ser Asp Ala Tyr Gly Trp Tyr Gln
            20                  25                  30

Gln Lys Ser Pro Gly Ser Ala Pro Val Thr Leu Ile Tyr His Asn Asn
        35                  40                  45

Lys Arg Pro Ser Asp Ile Pro Ser Arg Phe Ser Gly Ser Ala Ser Gly
        50                  55                  60

Ser Thr Ala Thr Leu Thr Ile Thr Gly Val Arg Ala Glu Asp Glu Ala
65                  70                  75                  80

Val Tyr Phe Cys Gly Ser Phe Asp Ser Ser Tyr Leu Gly Tyr Val Asn
                85                  90                  95

Leu Phe Gly Ala Gly Thr Thr Leu Thr Val Leu
            100                 105

<210> SEQ ID NO 98
<211> LENGTH: 107
<212> TYPE: PRT
<213> ORGANISM: Gallus gallus

<400> SEQUENCE: 98

Ala Leu Thr Gln Pro Ala Ser Val Ser Ala Asn Leu Gly Gly Ala Val
1               5                   10                  15

Glu Ile Thr Cys Ser Gly Gly Tyr Ser Glu Ala Tyr Gly Trp Tyr Gln
            20                  25                  30

Gln Lys Ser Pro Gly Ser Ala Pro Val Thr Leu Ile Tyr Ser Asn Asp
        35                  40                  45

Lys Arg Pro Ser Asn Ile Pro Ser Arg Phe Ser Gly Ser Thr Ser Gly
        50                  55                  60

Ser Thr Ala Thr Leu Thr Ile Thr Gly Val Arg Ala Glu Asp Glu Ala
65                  70                  75                  80

Val Tyr Leu Cys Gly Ser Phe Asp Ser Ser Tyr Leu Gly Tyr Val Asn
                85                  90                  95

Leu Phe Gly Ala Gly Thr Thr Leu Thr Val Leu
            100                 105

<210> SEQ ID NO 99
<211> LENGTH: 105
<212> TYPE: PRT
<213> ORGANISM: Gallus gallus

<400> SEQUENCE: 99

Ala Leu Thr Gln Pro Ala Ser Val Ser Ala Asn Pro Gly Gly Thr Val
1               5                   10                  15

Lys Ile Thr Cys Ser Gly Gly Ser Gly Asn Tyr Tyr Ala Trp Tyr Gln
            20                  25                  30

Gln Lys Ala Pro Gly Ser Ala Pro Val Thr Leu Ile Tyr Glu Asn Asn
        35                  40                  45

Leu Arg Pro Ser Asn Ile Pro Ser Arg Phe Ser Gly Ala Leu Ser Gly
        50                  55                  60

Ser Thr Ala Thr Leu Ile Ile Thr Gly Val Gln Ala Glu Asp Glu Ala
65                  70                  75                  80

Val Tyr Phe Cys Gly Gly Tyr Asp Ser Ser Tyr Ser Ala Ile Phe
                85                  90                  95

```
Gly Ala Gly Thr Thr Leu Thr Val Leu
            100                 105

<210> SEQ ID NO 100
<211> LENGTH: 108
<212> TYPE: PRT
<213> ORGANISM: Gallus gallus

<400> SEQUENCE: 100

Ala Leu Thr Gln Gln Pro Ala Ser Val Ser Ala Asn Pro Gly Glu Thr
1               5                   10                  15

Val Lys Ile Ala Cys Ser Gly Gly Val Tyr Ile Tyr Gly Ser Tyr Tyr
            20                  25                  30

Tyr Gly Trp Tyr Gln Gln Lys Ser Pro Gly Ser Ala Pro Val Thr Leu
        35                  40                  45

Ile Tyr Glu Asn Asp Lys Arg Pro Ser Asp Ile Pro Ser Arg Phe Ser
    50                  55                  60

Gly Ser Ala Ser Gly Ser Thr Ala Thr Leu Thr Ile Thr Gly Val Gln
65                  70                  75                  80

Val Glu Asp Glu Ala Val Tyr Phe Cys Gly Ser His Glu Asp Thr Ser
                85                  90                  95

Ser Leu Phe Gly Ala Gly Thr Thr Leu Thr Val Leu
            100                 105

<210> SEQ ID NO 101
<211> LENGTH: 105
<212> TYPE: PRT
<213> ORGANISM: Gallus gallus

<400> SEQUENCE: 101

Ala Leu Thr Gln Pro Ala Ser Val Ser Ala Asn Pro Gly Glu Thr Val
1               5                   10                  15

Lys Ile Thr Cys Ser Gly Gly Ser Gly Gly Tyr Tyr Gly Trp Tyr Gln
            20                  25                  30

Gln Lys Ser Pro Gly Ser Ala Pro Val Ser Leu Ile Tyr Glu Asn Asn
        35                  40                  45

Gln Arg Pro Ser Asn Ile Pro Ser Arg Phe Ser Gly Ser Glu Ser Gly
    50                  55                  60

Ser Thr Ala Thr Leu Thr Ile Thr Gly Val Gln Ala Glu Asp Glu Ala
65                  70                  75                  80

Val Tyr Phe Cys Gly Gly Tyr Asp Ser Ser Thr Tyr Ser Ala Val Phe
                85                  90                  95

Gly Ala Gly Thr Thr Leu Thr Val Leu
            100                 105

<210> SEQ ID NO 102
<211> LENGTH: 105
<212> TYPE: PRT
<213> ORGANISM: Gallus gallus

<400> SEQUENCE: 102

Ala Leu Thr Gln Pro Ala Ser Val Ser Ala Asn Leu Gly Gly Thr Val
1               5                   10                  15

Glu Ile Thr Cys Ser Gly Gly Ala Gly Ser Ser Asp Tyr Gly Trp Tyr
            20                  25                  30

Gln Gln Lys Ser Pro Gly Ser Ala Pro Val Thr Val Ile Tyr Glu Ser
        35                  40                  45

Thr Lys Arg Pro Ser Asn Leu Pro Ser Arg Phe Ser Gly Ser Lys Ser
```

-continued

```
        50                  55                  60

Gly Ser Thr Ala Thr Leu Thr Ile Thr Gly Val Gln Ala Glu Asp Glu
65                  70                  75                  80

Ala Val Tyr Tyr Cys Gly Ser Tyr Asp Asn Thr Asp Gly Asp Ile Phe
                85                  90                  95

Gly Ala Gly Thr Thr Leu Thr Val Leu
            100                 105

<210> SEQ ID NO 103
<211> LENGTH: 105
<212> TYPE: PRT
<213> ORGANISM: Gallus gallus

<400> SEQUENCE: 103

Ala Leu Thr Gln Pro Ala Ser Val Ser Ala Asn Pro Gly Glu Thr Val
1                   5                   10                  15

Glu Ile Thr Cys Ser Gly Gly Gly Ser Ser Tyr Tyr Gly Trp Tyr
                20                  25                  30

Gln Gln Lys Ser Pro Gly Ser Ala Pro Val Ser Leu Ile Tyr Glu Ser
            35                  40                  45

Asn Lys Arg Pro Ser Asn Ile Pro Ser Arg Phe Ser Gly Ser Thr Ser
        50                  55                  60

Gly Ser Thr Ser Thr Leu Thr Ile Thr Gly Val Gln Ala Asp Asp Glu
65                  70                  75                  80

Ala Val Tyr Tyr Cys Gly Ser Ala Asp Ser Ser Ala Ser Asn Leu Phe
                85                  90                  95

Gly Ala Gly Thr Thr Leu Thr Val Leu
            100                 105

<210> SEQ ID NO 104
<211> LENGTH: 104
<212> TYPE: PRT
<213> ORGANISM: Gallus gallus

<400> SEQUENCE: 104

Ala Val Thr Gln Pro Ala Ser Val Ser Ala Asn Leu Gly Glu Thr Val
1                   5                   10                  15

Glu Ile Thr Cys Ser Arg Gly Gly Ser Ser Asp Tyr Gly Trp Tyr
                20                  25                  30

Gln Gln Lys Ser Pro Gly Ser Ala Pro Val Thr Leu Ile Tyr Glu Ser
            35                  40                  45

Thr Lys Arg Pro Ser Asn Ile Pro Ser Arg Phe Ser Gly Ser Lys Ser
        50                  55                  60

Gly Ser Thr Ser Thr Leu Thr Ile Thr Gly Val Gln Ala Glu Asp Glu
65                  70                  75                  80

Ala Val Tyr Tyr Cys Gly Ser Tyr Asp Ser Ser Ala Asp Ile Phe Gly
                85                  90                  95

Ala Gly Thr Thr Leu Thr Val Leu
            100

<210> SEQ ID NO 105
<211> LENGTH: 104
<212> TYPE: PRT
<213> ORGANISM: Gallus gallus

<400> SEQUENCE: 105

Ala Val Thr Gln Pro Ala Ser Val Ser Ala Asn Leu Gly Glu Thr Val
1                   5                   10                  15
```

-continued

```
Glu Ile Thr Cys Ser Gly Gly Gly Ser Ser Asp Tyr Gly Trp Tyr
            20                  25                  30

Gln Gln Lys Ser Pro Gly Ser Ala Pro Val Thr Leu Ile Tyr Glu Ser
            35                  40                  45

Thr Lys Arg Pro Ser Asn Ile Pro Ser Arg Phe Ser Gly Ser Lys Ser
            50                  55                  60

Gly Ser Thr Ser Thr Leu Thr Ile Thr Gly Val Gln Ala Glu Asp Glu
65                  70                  75                  80

Ala Val Tyr Tyr Cys Gly Ser Tyr Asp Ser Ser Ala Asp Ile Phe Gly
                85                  90                  95

Ala Gly Thr Thr Leu Thr Val Leu
            100
```

```
<210> SEQ ID NO 106
<211> LENGTH: 104
<212> TYPE: PRT
<213> ORGANISM: Gallus gallus

<400> SEQUENCE: 106
```

```
Ala Val Thr Gln Pro Ala Ser Val Ser Ala Asn Leu Gly Glu Thr Val
1                   5                   10                  15

Glu Ile Thr Cys Ser Gly Gly Gly Ser Ser Asp Tyr Gly Trp Tyr
            20                  25                  30

Gln Gln Lys Ser Pro Gly Ser Ala Pro Val Thr Leu Ile Tyr Glu Ser
            35                  40                  45

Thr Lys Arg Pro Ser Asn Ile Pro Ser Arg Phe Ser Gly Ser Lys Ser
            50                  55                  60

Gly Ser Thr Ser Thr Leu Thr Ile Thr Gly Val Gln Ala Glu Asp Glu
65                  70                  75                  80

Ala Val Tyr Tyr Cys Gly Ser Tyr Asp Ser Ser Ala Asp Ile Phe Gly
                85                  90                  95

Ala Gly Thr Thr Leu Thr Val Leu
            100
```

```
<210> SEQ ID NO 107
<211> LENGTH: 106
<212> TYPE: PRT
<213> ORGANISM: Gallus gallus

<400> SEQUENCE: 107
```

```
Ala Val Thr Gln Pro Ala Ser Val Ser Ala Asn Pro Gly Glu Thr Val
1                   5                   10                  15

Lys Ile Thr Cys Ser Gly Ser Ser Gly Ser Tyr Gly Trp Tyr Gln Gln
            20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Lys Ser Gly Ser
            50                  55                  60

Thr Ala Thr Leu Thr Ile Thr Gly Val Gln Ala Glu Asp Glu Ala Val
65                  70                  75                  80

Tyr Tyr Cys Gly Asn Val Gly Tyr Thr Asp Thr Ser Tyr Asp Gly Ile
                85                  90                  95

Phe Gly Ala Gly Thr Thr Leu Thr Val Leu
            100                 105
```

```
<210> SEQ ID NO 108
```

<211> LENGTH: 103
<212> TYPE: PRT
<213> ORGANISM: Gallus gallus

<400> SEQUENCE: 108

Ala Leu Thr Gln Pro Ser Ser Val Ser Ala Asn Pro Gly Glu Thr Val
1               5                   10                  15

Lys Ile Thr Cys Ser Gly Ser Ser Gly Ser Tyr Gly Trp Tyr Gln Gln
                20                  25                  30

Lys Ser Pro Gly Ser Ala Pro Val Thr Val Ile Tyr Thr Asn Asn Gln
            35                  40                  45

Arg Pro Ser Asp Ile Pro Ser Arg Phe Ser Gly Ser Leu Ser Gly Ser
        50                  55                  60

Thr Asn Thr Leu Thr Ile Thr Gly Val Gln Ala Asp Asp Glu Ala Val
65                  70                  75                  80

Tyr Phe Cys Gly Ser Thr Asp Ser Ser Thr Asp Gly Ala Phe Gly Ala
                85                  90                  95

Gly Thr Thr Leu Thr Val Leu
            100

<210> SEQ ID NO 109
<211> LENGTH: 105
<212> TYPE: PRT
<213> ORGANISM: Gallus gallus

<400> SEQUENCE: 109

Ala Leu Thr Gln Gln Pro Ala Ser Val Ser Ala Asn Pro Gly Glu Thr
1               5                   10                  15

Val Lys Ile Thr Cys Ser Gly Asp Thr Tyr His Tyr Gly Trp Tyr Gln
                20                  25                  30

Gln Lys Ser Pro Gly Ser Ala Pro Val Thr Val Ile Tyr Ser Asn Asp
            35                  40                  45

Lys Arg Pro Ser Asn Ile Pro Ser Arg Phe Ser Gly Ser Lys Ser Gly
        50                  55                  60

Ser Thr His Thr Leu Thr Ile Thr Gly Val Gln Ala Glu Asp Glu Ala
65                  70                  75                  80

Ile Tyr Tyr Cys Gly Cys Glu Asp Ser Ser Ser Tyr Val Gly Met Phe
                85                  90                  95

Gly Ala Gly Thr Thr Leu Thr Val Leu
            100                 105

<210> SEQ ID NO 110
<211> LENGTH: 103
<212> TYPE: PRT
<213> ORGANISM: Gallus gallus

<400> SEQUENCE: 110

Ala Val Thr Gln Pro Ala Ser Val Ser Ala Asn Leu Gly Gly Thr Val
1               5                   10                  15

Lys Ile Thr Cys Ser Gly Ser Ser Gly Thr Tyr Gly Trp Tyr Gln Gln
                20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Lys Ser Gly Ser
        50                  55                  60

Thr Gly Thr Leu Thr Ile Thr Gly Val Gln Ala Glu Asp Glu Ala Val
65                  70                  75                  80

-continued

```
Tyr Phe Cys Gly Ser Ala Asp Ser Asn Tyr Val Gly Leu Phe Gly Ala
                85                  90                  95

Gly Thr Thr Leu Thr Val Leu
            100

<210> SEQ ID NO 111
<211> LENGTH: 105
<212> TYPE: PRT
<213> ORGANISM: Gallus gallus

<400> SEQUENCE: 111

Ala Val Thr Gln Pro Ala Ser Val Ser Ala Asn Leu Gly Gly Thr Val
1               5                   10                  15

Glu Ile Thr Cys Ser Gly Gly Gly Asp Ser Asn Tyr Gly Trp Tyr Gln
                20                  25                  30

Gln Lys Ser Pro Gly Ser Ala Pro Val Thr Leu Ile Tyr Asp Asn Thr
            35                  40                  45

Asn Arg Pro Thr Gly Ile Pro Ser Arg Phe Ser Gly Ser Arg Ser Gly
        50                  55                  60

Ser Thr Ala Thr Leu Thr Ile Thr Gly Val Gln Ala Asp Asp Glu Ala
65                  70                  75                  80

Val Tyr Tyr Cys Gly Asn Ala Asp Ser Ser Ser Ser Ala Gly Ile Phe
                85                  90                  95

Gly Ala Gly Thr Thr Leu Thr Val Leu
            100                 105

<210> SEQ ID NO 112
<211> LENGTH: 105
<212> TYPE: PRT
<213> ORGANISM: Gallus gallus

<400> SEQUENCE: 112

Ala Val Thr Gln Pro Ala Ser Val Ser Ala Asn Leu Gly Gly Thr Val
1               5                   10                  15

Lys Ile Thr Cys Ser Gly Gly Gly Asp Ser Asn Tyr Gly Trp Tyr Gln
                20                  25                  30

Gln Lys Ser Pro Gly Ser Ala Pro Val Thr Val Ile Tyr Asp Asn Thr
            35                  40                  45

Asn Arg Pro Ser Asn Ile Pro Ser Arg Phe Ser Gly Ser Lys Ser Gly
        50                  55                  60

Ser Thr Ala Thr Leu Thr Ile Thr Gly Val Gln Ala Glu Asp Glu Ala
65                  70                  75                  80

Val Tyr Phe Cys Gly Ser Ala Asp Ser Ser Ser Ser Ala Gly Met Phe
                85                  90                  95

Gly Ala Gly Thr Thr Leu Thr Val Leu
            100                 105

<210> SEQ ID NO 113
<211> LENGTH: 109
<212> TYPE: PRT
<213> ORGANISM: Gallus gallus

<400> SEQUENCE: 113

Ala Val Thr Gln Pro Ala Ser Val Ser Ala Asn Pro Gly Glu Thr Val
1               5                   10                  15

Lys Ile Thr Cys Ser Gly Gly Gly Thr Tyr Gly Tyr Gly Ser Tyr Tyr
                20                  25                  30

Tyr Gly Trp Tyr Gln Gln Lys Ala Pro Gly Ser Ala Pro Val Thr Val
```

```
          35                  40                  45

Ile Tyr Asp Asn Thr Asn Arg Pro Ser Asn Ile Pro Ser Arg Phe Ser
    50                  55                  60

Gly Ser Thr Ser Gly Ser Thr Ala Thr Leu Thr Val Thr Gly Val Gln
65                  70                  75                  80

Val Glu Asp Glu Ala Val Tyr Tyr Cys Gly Ser Ile Asp Ser Ser Asn
                85                  90                  95

Val Gly Ile Phe Gly Ala Gly Thr Thr Leu Thr Val Leu
            100                 105

<210> SEQ ID NO 114
<211> LENGTH: 104
<212> TYPE: PRT
<213> ORGANISM: Gallus gallus

<400> SEQUENCE: 114

Ala Leu Thr Gln Gln Pro Ala Ser Val Ser Ala Ser Pro Gly Glu Thr
1               5                   10                  15

Val Lys Ile Thr Cys Ser Gly Gly Ser Tyr Ser Tyr Gly Trp Phe Gln
                20                  25                  30

Gln Lys Ser Pro Gly Ser Ala Leu Val Thr Leu Ile Tyr Gly Asn Thr
            35                  40                  45

Asp Arg Pro Ser Asp Thr Pro Ser Arg Phe Ser Gly Ser Ala Ser Gly
    50                  55                  60

Ser Thr Ala Thr Leu Thr Ile Thr Gly Val Gln Ala Asp Asp Glu Ala
65                  70                  75                  80

Val Tyr Tyr Cys Gly Thr Ala Asp Asn Thr Tyr Val Ala Ile Phe Gly
                85                  90                  95

Ala Gly Thr Thr Leu Thr Val Leu
            100

<210> SEQ ID NO 115
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: REPEAT
<222> LOCATION: (1)..(5)
<223> OTHER INFORMATION: The sequence repeats n times, where n is an
      integer of at least one

<400> SEQUENCE: 115

Gly Ser Gly Gly Ser
1               5

<210> SEQ ID NO 116
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: REPEAT
<222> LOCATION: (1)..(4)
<223> OTHER INFORMATION: The sequence repeats n times, where n is an
      integer of at least one

<400> SEQUENCE: 116

Gly Gly Gly Ser
1
```

```
<210> SEQ ID NO 117
<211> LENGTH: 4
<212> TYPE: PRT
<213> ORGANISM: Artificial sequence
<220> FEATURE:
<223> OTHER INFORMATION: synthetic sequence

<400> SEQUENCE: 117

Gly Gly Ser Gly
1

<210> SEQ ID NO 118
<211> LENGTH: 5
<212> TYPE: PRT
<213> ORGANISM: Artificial sequence
<220> FEATURE:
<223> OTHER INFORMATION: synthetic sequence

<400> SEQUENCE: 118

Gly Gly Ser Gly Gly
1               5

<210> SEQ ID NO 119
<211> LENGTH: 5
<212> TYPE: PRT
<213> ORGANISM: Artificial sequence
<220> FEATURE:
<223> OTHER INFORMATION: synthetic sequence

<400> SEQUENCE: 119

Gly Ser Gly Ser Gly
1               5

<210> SEQ ID NO 120
<211> LENGTH: 5
<212> TYPE: PRT
<213> ORGANISM: Artificial sequence
<220> FEATURE:
<223> OTHER INFORMATION: synthetic sequence

<400> SEQUENCE: 120

Gly Ser Gly Gly Gly
1               5

<210> SEQ ID NO 121
<211> LENGTH: 5
<212> TYPE: PRT
<213> ORGANISM: Artificial sequence
<220> FEATURE:
<223> OTHER INFORMATION: synthetic sequence

<400> SEQUENCE: 121

Gly Gly Gly Ser Gly
1               5

<210> SEQ ID NO 122
<211> LENGTH: 5
<212> TYPE: PRT
<213> ORGANISM: Artificial sequence
<220> FEATURE:
<223> OTHER INFORMATION: synthetic sequence

<400> SEQUENCE: 122

Gly Ser Ser Ser Gly
1               5
```

-continued

```
<210> SEQ ID NO 123
<211> LENGTH: 10
<212> TYPE: PRT
<213> ORGANISM: Artificial sequence
<220> FEATURE:
<223> OTHER INFORMATION: synthetic sequence

<400> SEQUENCE: 123

Cys Tyr Pro Tyr Asp Val Pro Asp Tyr Ala
1               5                   10

<210> SEQ ID NO 124
<211> LENGTH: 8
<212> TYPE: PRT
<213> ORGANISM: Artificial sequence
<220> FEATURE:
<223> OTHER INFORMATION: synthetic sequence

<400> SEQUENCE: 124

Asp Tyr Lys Asp Asp Asp Asp Lys
1               5

<210> SEQ ID NO 125
<211> LENGTH: 11
<212> TYPE: PRT
<213> ORGANISM: Artificial sequence
<220> FEATURE:
<223> OTHER INFORMATION: synthetic sequence

<400> SEQUENCE: 125

Cys Glu Gln Lys Leu Ile Ser Glu Glu Asp Leu
1               5                   10

<210> SEQ ID NO 126
<211> LENGTH: 5
<212> TYPE: PRT
<213> ORGANISM: Artificial sequence
<220> FEATURE:
<223> OTHER INFORMATION: synthetic sequence

<400> SEQUENCE: 126

His His His His His
1               5

<210> SEQ ID NO 127
<211> LENGTH: 6
<212> TYPE: PRT
<213> ORGANISM: Artificial sequence
<220> FEATURE:
<223> OTHER INFORMATION: synthetic sequence

<400> SEQUENCE: 127

His His His His His His
1               5

<210> SEQ ID NO 128
<211> LENGTH: 10
<212> TYPE: PRT
<213> ORGANISM: Artificial sequence
<220> FEATURE:
<223> OTHER INFORMATION: synthetic sequence

<400> SEQUENCE: 128

Glu Gln Lys Leu Ile Ser Glu Glu Asp Leu
1               5                   10

<210> SEQ ID NO 129
```

-continued

```
<211> LENGTH: 8
<212> TYPE: PRT
<213> ORGANISM: Artificial sequence
<220> FEATURE:
<223> OTHER INFORMATION: synthetic sequence

<400> SEQUENCE: 129

Trp Ser His Pro Gln Phe Glu Lys
1               5

<210> SEQ ID NO 130
<211> LENGTH: 9
<212> TYPE: PRT
<213> ORGANISM: Artificial sequence
<220> FEATURE:
<223> OTHER INFORMATION: synthetic sequence

<400> SEQUENCE: 130

Tyr Pro Tyr Asp Val Pro Asp Tyr Ala
1               5

<210> SEQ ID NO 131
<211> LENGTH: 5
<212> TYPE: PRT
<213> ORGANISM: Artificial sequence
<220> FEATURE:
<223> OTHER INFORMATION: synthetic sequence

<400> SEQUENCE: 131

Arg Tyr Ile Arg Ser
1               5

<210> SEQ ID NO 132
<211> LENGTH: 4
<212> TYPE: PRT
<213> ORGANISM: Artificial sequence
<220> FEATURE:
<223> OTHER INFORMATION: synthetic sequence

<400> SEQUENCE: 132

Phe His His Thr
1

<210> SEQ ID NO 133
<211> LENGTH: 17
<212> TYPE: PRT
<213> ORGANISM: Artificial sequence
<220> FEATURE:
<223> OTHER INFORMATION: synthetic sequence

<400> SEQUENCE: 133

Trp Glu Ala Ala Ala Arg Glu Ala Cys Cys Arg Glu Cys Cys Ala Arg
1               5                   10                  15

Ala
```

HUMAN GLUCOSE-DEPENDENT INSULINOTROPIC POLYPEPTIDE RECEPTOR (GIPR) ANTIBODIES AND METHODS OF USE THEREOF TO INHIBIT GIP RECEPTOR AND SIGNALING

CROSS-REFERENCING

This application is a § 371 national phase of International Application No. PCT/US2021/019096, filed on Feb. 22, 2021, which claims the benefit of U.S. provisional application Ser. No. 63/001,857, filed on Mar. 30, 2020, which applications are incorporated by reference herein.

BACKGROUND

Glucose-dependent Insulinotropic Polypeptide, also named Gastric Inhibitory Polypeptide (or GIP), has long been known as one of the incretins stimulating insulin secretion in response to food intake. However, in the context of diabetes the insulinotropic action of GIP is markedly diminished. In contrast, effects of GIP on fat deposition and lipid metabolism in adipose tissue are not impaired, thus promoting the development of insulin resistance and obesity. Furthermore, GIP stimulates the secretion of glucagon, which might contribute to the lack of postprandial glucagon suppression and hyperglycemia seen in patients with type 2 diabetes.

GIP, a 42-amino acid peptide, is released into circulation from K cells in the duodenum and small intestine upon nutrient ingestion. GIP exerts is activity via its receptor, GIPR. GIPR is expressed primarily in the pancreas, adipose tissue, stomach, small intestine, bone and central nervous system. The GIP receptor is a member of the Class B (Secretin) family of G protein-coupled receptors and activation results in the stimulation of adenylyl cyclase and Ca(2+)-independent phospholipase A(2) and activation of protein kinase (PK) A and PKB. The GIP receptor is coupled to $G\alpha_s$, and activation of the receptor leads to an increase of the second messenger cAMP. GIPR is characterized by a large extracellular loop (extracellular domain—ECD) that serves as the site of specific interaction with its ligand, binding with low affinity ($\mu$M range). The ECD confers the selectivity of the receptor to its ligand, and upon binding a conformational change leads to receptor activation with potency in the pM range.

Various groups have shown that GIPR antagonism has a beneficiary impact on disease phenotype in rodent models. Under a high fat diet, GIPR knock-out mice show an increased insulin-sensitivity, a resistance against diet-induced obesity, suppression of liver steatosis, and reduced plasma cholesterol and triglyceride levels. Similar effects are seen with a variety of antagonistic peptides, and recently with antagonistic antibodies raised in a phage display campaign.

GPCRs, however, are difficult targets for antibody campaigns. Often, GPCRs occur in low density on the cell surface and are very unstable when purified from the cellular membrane, presenting a challenge in obtaining sufficient amounts of immunogen in which native epitopes are maintained for antibody recognition. Furthermore, a particular therapeutic concept may require an antibody that does not just bind the GPCR but acts as an agonist or antagonist, which may necessitate the recognition of particular, potentially ligand-sensitive, epitopes. These additional requirements may further reduce the effective hit rate in antibody generation campaigns.

In addition to the challenges of preparing native GCPR protein for use as an immunogen, the receptor structure itself offers relatively few antigenic determinants at the cell surface that are potentially available for antibody binding. This paucity, when combined with the further restriction imposed by immunological tolerance, can lead to very poor immunogenicity for sequence-conserved GPCR targets.

SUMMARY OF THE INVENTION

The present disclosure provides antibodies that specifically bind to and in some cases inhibit the human glucose-dependent insulinotropic polypeptide (GIP) receptor. The antibodies find use in a variety of treatment, diagnostic, and monitoring applications, which are also described.

In some embodiments, the antibody may comprise: (a) a variable domain comprising: i. heavy chain CDR1, CDR2 and CDR3 regions that are identical to the heavy chain CDR1, CDR2 and CDR3 regions of an antibody selected from FIG. 9; and ii. light chain CDR1, CDR2 and CDR3 regions that are identical to the light chain CDR1, CDR2 and CDR3 regions of an antibody selected from FIG. 10; or (b) a variant of said variable domain of (a) that is otherwise identical to said antibody variable domain except for up to 10 (e.g., up to 9, 8, 7, 6, 5, 4, 3, 2, or 1) amino acid substitutions in the collective CDR regions of the variable domain of (a).

In some embodiments, the antibody comprises: a heavy chain variable domain comprising an amino acid sequence that is at least 90% (e.g., at least 95%) identical to the amino acid sequence of the heavy chain variable domain of an antibody selected from FIG. 9; and a light chain variable domain comprising an amino acid sequence that is at least 90% (e.g., at least 95%) identical to the light chain variable domain of the antibody, selected from FIG. 10.

Human and murine GIPR have 81% identity at the protein level. Previous studies in which mice and rats were used to raise antibodies against the human GIPR resulted in a very small panel of functional antibody clones with limited epitope coverage. In the present study, chicken was used as an alternative host in order to generate a more diverse panel of antibodies. There is greater evolutionary distance between humans and chickens compared to humans and other mammals such as mice. This evolutionary distance allows chickens to produce a more vigorous and diverse immune response when challenged with human proteins. In the specific case of GIPR, the chicken has no known ortholog, and thus it is effectively a "knockout" for this target. Another major advantage of chicken immunization is the generation of antibodies that recognize "pan-mammalian" epitopes; such antibodies are difficult or impossible to generate in mammalian hosts. An additional advantage of chicken antibodies comes with the broad species cross-reactivity, obviating the need to generate surrogate antibodies for the purpose of experimentation in various disease models.

The present disclosure also provides a method of treating a metabolic disorder, such as a disorder of glucose metabolism (e.g. Type 2 diabetes, elevated glucose levels, elevated insulin levels, dyslipidemia, metabolic syndrome (Syndrome X or insulin resistance syndrome), glucosuria, metabolic acidosis, Type 1 diabetes, obesity and conditions exacerbated by obesity) by blocking or interfering with the biological activity of GIP. In one embodiment, a therapeutically effective amount of subject antibody is administered to a subject in need thereof. Methods of administration and delivery are also provided.

For example, in one aspect, the present disclosure provides a method of treating a subject with a metabolic disorder, the method comprising administering to the subject a therapeutically effective amount of a subject antibody. In one embodiment, the metabolic disorder is a disorder of glucose metabolism. In another embodiment, the glucose metabolism disorder comprises hyperglycemia and administering the antibody protein reduces plasma glucose. In another embodiment, the glucose metabolism disorder comprises hyperinsulinemia and administering the antibody reduces plasma insulin. In another embodiment, the glucose metabolism disorder comprises glucose intolerance and administering the antibody reduces increases glucose tolerance. In another embodiment, the glucose metabolism disorder comprises insulin resistance and administering the antibody reduces insulin resistance. In another embodiment, the glucose metabolism disorder comprises diabetes mellitus. In another embodiment, the subject is obese. In another embodiment, administering the antibody reduces body weight in an obese subject. In another embodiment, administering the antibody reduces body weight gain in an obese subject. In another embodiment, administering the antibody reduces fat mass in an obese subject. In another embodiment, the glucose metabolism disorder comprises insulin resistance and administering the antibody reduces insulin resistance in an obese subject. In another embodiment, administering the antibody reduces liver steatosis in an obese subject having increased liver steatosis. In another embodiment, administering the antibody reduces liver fat content in an obese subject having increased liver fat content.

Thus, the present antibodies have a number of advantages over antibodies that are produced in mammalian hosts.

BRIEF DESCRIPTION OF THE DRAWINGS

FIG. 5: Biolayer interferometry derived epitope clustering for anti-GIPR antibodies. A two dimensional matrix of the normalized biolayer interferometry assay data used for epitope clustering is shown. 45 anti-GIPR antibodies were assessed, 40 derived from chicken, 5 from other sources (rodent & phage display). The secondary antibodies are shown as rows, the primary antibodies as columns. Rows were sorted by their Pearson correlation coefficient (penultimate column on the right). Following Pearson row sorting, the columns were sorted to match the rows—hence the self-blocking value for each antibody is found on the diagonal (values marked in red). In addition, the Pearson correlation coefficient for the columns is shown in the bottom row. A color gradient from blue (0) to white (100) was applied to the data to highlight cross-blocking or competition. The last-most column indicates the epitope cluster an antibody was assigned based on the dendrogram shown in FIG. 6.

FIG. 8: GIPR-N terminal extracellular domain sequences. Shown are the human (SEQ ID NO:32), mouse (SEQ ID NO:33) and rat (SEQ ID NO:34) extracellular domain amino acids (22-139) that were used to generate recombinant rabbit (for biophysical analyses) or human (as antigen for immunization) Fc fusion proteins respectively.

Figure 9:
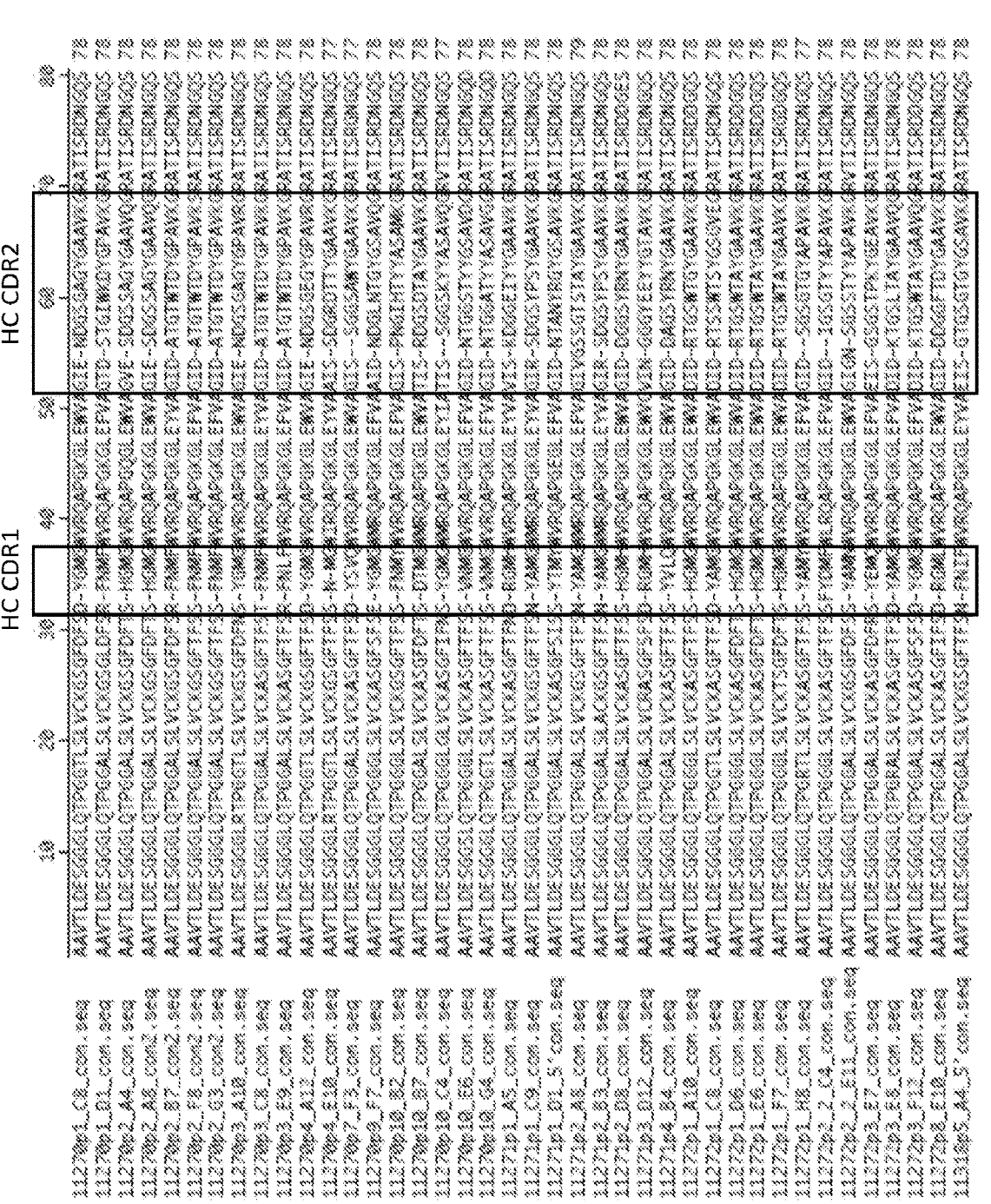

FIG. 9: Heavy chain sequences. FIG. 9 provides the amino acid sequence of 40 anti-GIPR antibody heavy chain variable regions, in which the complementarity determining regions (CDRs) as defined by the Chothia method are indicated by boxes. From top to bottom: SEQ ID NOS: 35-74.

Figure 10:
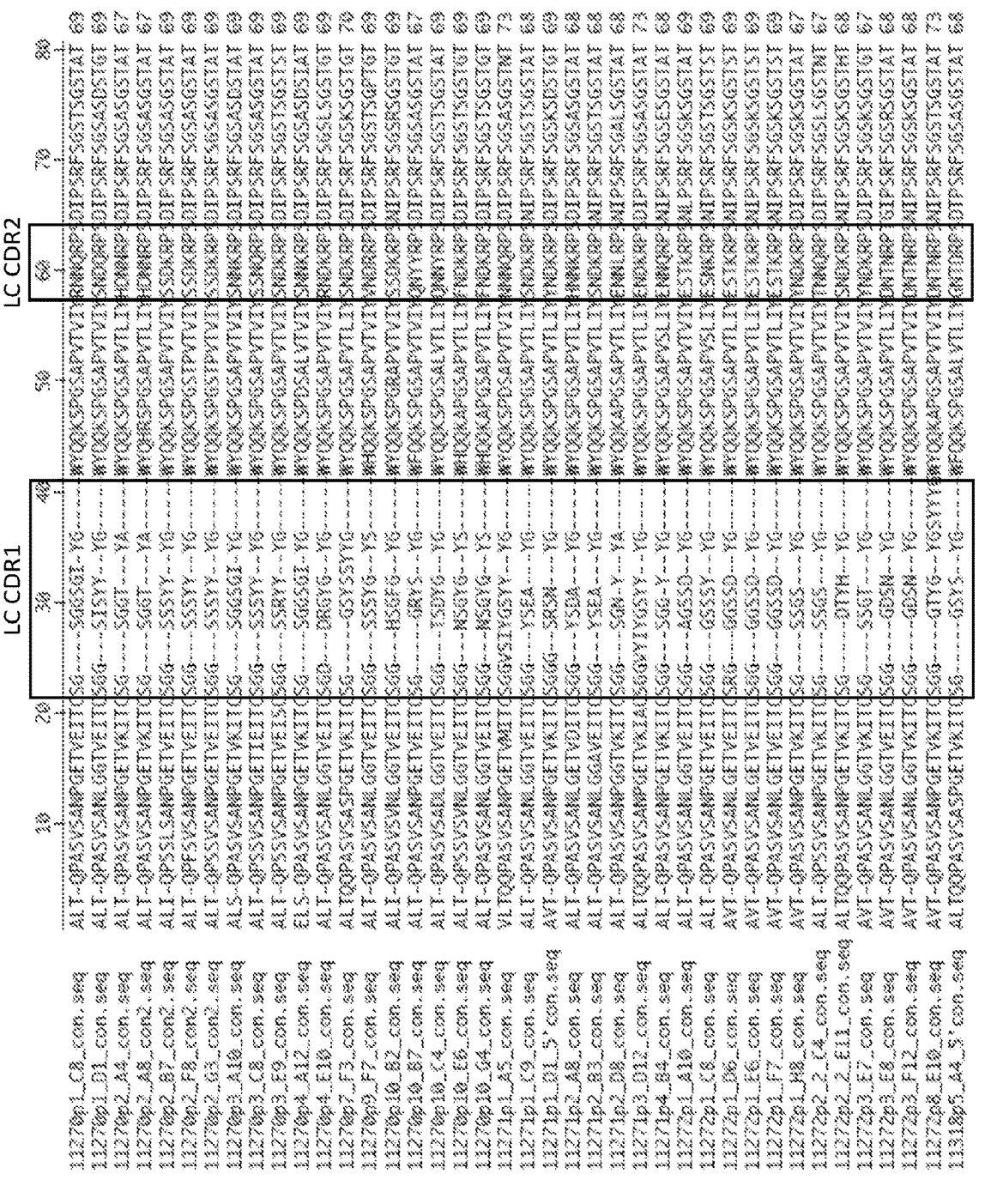
Figure 10:
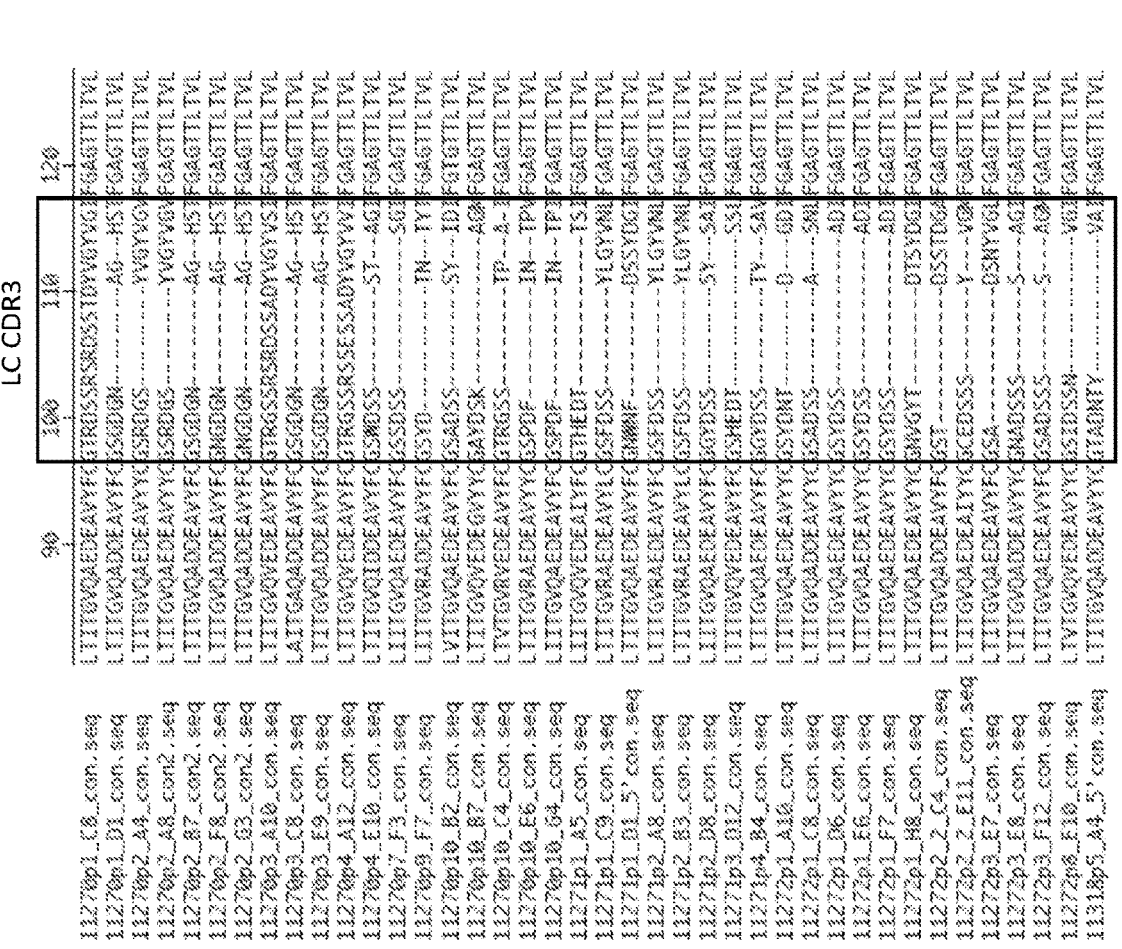

FIG. 10: Light chain sequences. FIG. 10 provides the amino acid sequence of 40 anti-GIPR antibody light chain variable regions, in which the complementarity determining regions (CDRs) as defined by the Chothia method are indicated by boxes. From top to bottom: SEQ ID NOS: 75-114.

DEFINITIONS

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the V$_H$-V$_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH$_1$) of the heavy chain. Fab fragments differ from Fab' fragments by the addition of a few residues at the carboxyl terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the V$_H$ and V$_L$ domains of antibody, wherein these domains are present in a single polypeptide chain. In some embodiments, the Fv polypeptide further comprises a polypeptide linker between the V$_H$ and V$_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (V$_H$) connected to a light-chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/ or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. An anti-GIPR antibody binds specifically to an epitope within a GIPR polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The CDRs indicated in FIGS. 9 and 10 are defined by the Chothia method. However, as indicated below, the Kabat and MacCallum method could also be used to define the CDRs.

TABLE 1

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of an anti-GIPR antibody that, when administered to a mammal or other subject for treating a disease, is sufficient to effect such treatment for the disease. The "therapeutically effective amount" will vary depending on the anti-GIPR antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the term "collectively" in the context of a variant of an antibody variable domain that is otherwise identical to the antibody variable domain except for a defined number of amino acid substitutions "in the collective CDR regions of the antibody variable domain", indicates that the number of amino acid substitutions is counted using all six CDRs. Explained by example, if the variant has 5 amino acid substitutions relative to the antibody variable domain, then the six CDRs of the variant, combined, have a total of 5 amino acid substitutions relative to the antibody variable domain. This phrase is not intended to mean that each CDR has a defined number of amino acid substitutions.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the anti-GIPR antibody" includes reference to one or more anti-GIPR antibodies and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibodies that bind to human GIPR. The antibodies are useful in various treatment, diagnostic, and monitoring applications, which are also provided.

In some embodiments, a subject antibody specifically binds GIPR from humans and other mammals, e.g., monkey and mouse.

For example, a subject antibody may bind to human, monkey and/or mouse GIPR with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject antibody binds to an epitope present on human, monkey and/or mouse GIPR with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

A subject antibody can in some embodiments reduce binding of GIPR to a GIP. For example, in some embodiments a subject antibody can reduce binding of GIPR to GIP by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of binding between GIPR and GIP in the absence of the antibody.

In some embodiments a subject antibody may reduce GIPR activity, i.e., signaling in response to GIP. For example, in some embodiments a subject antibody may reduce GIPR signaling by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to GIPR signaling in the absence of the antibody.

The term "antibody" refers to a protein comprising one or more (e.g., one or two) heavy chain variable regions (VH) and/or one or more (e.g., one or two) light chain variable regions (VL), or subfragments thereof capable of binding an epitope. The VH and VL regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) Sequences of Proteins of Immunological Interest, Fifth Edition, U.S. Department of Health and Human Services, NIH Publication No. 91-3242; Chothia et al. (1987) J. Mol. Biol. 196: 901-917). A VH can comprise three CDRs and four FRs arranged from N-terminus to C-terminus in the following order: FR1, CDR1, FR2, CDR2, FR3, CDR3, FR4. Similarly, a VL can comprise three CDRs and four FRs arranged from N-terminus to C-terminus in the following order: FR1, CDR1, FR2, CDR2, FR3, CDR3, FR4.

The VH or VL chain of an antibody can further include all or part of a heavy or light chain constant region, to thereby form a heavy or light immunoglobulin chain, respectively. In one embodiment, the antibody is a tetramer of two heavy and two light chains, wherein the heavy and light chains are interconnected by, for example, disulfide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes intact immunoglobulins of types IgA, IgG, IgE, IgD, IgM and subtypes thereof. In some embodiments, a subject antibody is an IgG isotype.

As used herein the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

In some embodiments, a subject antibody does not comprise a full-length immunoglobulin heavy chain and a full-length immunoglobulin light chain, and instead comprises antigen-binding fragments of a full-length immunoglobulin heavy chain and/or a full-length immunoglobulin light chain. In some embodiments, the antigen-binding fragments are contained on separate polypeptide chains; in other embodiments, the antigen-binding fragments are contained within a single polypeptide chain. The term "antigen-binding fragment" refers to one or more fragments of a full-length antibody that are capable of specifically binding to GIPR as described above. Examples of binding fragments include (i) a Fab fragment (a monovalent fragment consisting of the VL, VH, CL and CH1 domains; (ii) a F(ab')$_2$ fragment (a bivalent fragment comprising two Fab fragments linked by a disulfide bridge at the hinge region; (iii)

an Fd fragment (consisting of the VH and CH1 domains); (iv) an Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) dia-bodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). In some embodiments, a subject antibody fragment is a Fab fragment. In some embodiments, a subject antibody fragment is a single-chain antibody (scFv).

In some embodiments, a subject antibody is a recombi-nant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) anti-bodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

In some embodiments, a subject antibody comprises: a variable domain comprising: a) a heavy chain variable domain comprising: i. a CDR1 region that is identical in amino acid sequence to the sequence of a heavy chain CDR1 region of an antibody selected from the antibodies shown in FIGS. 9 and 10; ii. a CDR2 region that is identical in amino acid sequence to the sequence of a heavy chain CDR2 region of the selected antibody; and iii. a CDR3 region that is identical in amino acid sequence to the sequence of a heavy chain CDR3 region of the selected antibody; and b) a light chain variable domain comprising: i. a CDR1 region that is identical in amino acid sequence to the sequence of a light chain CDR1 region of the selected antibody; ii. a CDR2 region that is identical in amino acid sequence to that of a light chain CDR2 region of the selected antibody sequence; and iii. a CDR3 region that is identical in amino acid sequence to that of a light chain CDR3 region of the selected antibody; wherein the antibody specifically binds human, monkey, rat and/or mouse GIPR.

In certain embodiments, an antibody comprising: (a) a variable domain comprising: i. a CDR1 region that is identical in amino acid sequence to the heavy chain CDR1 region of an antibody selected from the antibodies shown in FIGS. 9 and 10; ii. a CDR2 region that is identical in amino acid sequence to the heavy chain CDR2 region of the selected antibody; and iii. a CDR3 region that is identical in amino acid sequence to the heavy chain CDR3 region of the selected antibody; and a light chain variable domain com-prising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; or (b) a variant of the variable domain of part (a) that is otherwise identical to the variable domain of part (a) except for up to 10 (e.g., up to 9, 8, 7, 6, 5, 4, 3, 2, or 1) amino acid substitutions in the collective CDR regions of the variable domain of (a), wherein the antibody binds to GIPR.

In some embodiments, the antibody may contain only a heavy chain variable domain described herein. In these embodiments, the antibody may be a "heavy chain only" antibody.

The heavy and light chain sequences disclosed herein can be analyzed via lineage analysis in order obtain consensus sequences for the CDRs. Groups of sequences that are believed to be related by lineage are indicated in FIGS. 9 and 10. Analysis of these sequences reveals which amino acid positions can tolerate amino acid substitutions and, as such, can be used to make variants of the present antibodies that have, for example, amino acid substitutions in the CDRs.

In some embodiments, a subject antibody (e.g., a subject antibody that specifically binds GIPR may comprises: a) a light chain region comprising: i) one, two, or three comple-mentarity determining regions (CDRs) from a light chain variable region sequence of a selected anti-GIPR antibody; and ii) a light chain framework region, e.g., a framework region from a human immunoglobulin light chain; and b) a heavy chain region comprising: i) one, two, or three CDRs from the heavy chain variable region sequence of a selected antibody; and ii) a heavy chain framework region, e.g., a framework region from a human immunoglobulin heavy chain.

A subject antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to a sequence depicted in FIG. 9 and set forth in SEQ ID NOS: 35-74. A subject antibody can comprise a heavy chain variable region comprising one, two, or three of the heavy chain complementarity determin-ing regions (CDRs) of a selected anti-GIPR antibody.

A subject antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 10 and set forth in SEQ ID NO: 75-114. A subject antibody can comprise a light chain variable region comprising one, two, or three of the light chain CDRs of a selected anti-GIPR antibody.

In some embodiments, a subject antibody comprises anti-GIPR antibody heavy chain CDRs and anti-GIPR anti-body light chain CDRs in a single polypeptide chain, e.g., in some embodiments, a subject antibody is a scFv. In some embodiments, a subject antibody comprises, in order from N-terminus to C-terminus: a first amino acid sequence of from about 5 amino acids to about 25 amino acids in length; an light chain CDR1 of a selected anti-GIPR antibody; a second amino acid sequence of from about 5 amino acids to about 25 amino acids in length; a light chain CDR2 of a selected anti-GIPR antibody; a third amino acid sequence of from about 5 amino acids to about 25 amino acids in length; a light chain CDR3 of a selected anti-GIPR antibody; a fourth amino acid sequence of from about 5 amino acids to about 25 amino acids in length; a heavy chain CDR1 of a selected anti-GIPR antibody; a fifth amino acid sequence of from about 5 amino acids to about 25 amino acids in length; a heavy chain CDR2 of a selected anti-GIPR antibody; a sixth amino acid sequence of from about 5 amino acids to about 25 amino acids in length; a heavy chain CDR3 of a selected anti-GIPR antibody; and a seventh amino acid sequence of from about 5 amino acids to about 25 amino acids in length.

In some embodiments, a subject antibody may comprise, in order from N-terminus to C-terminus: a light chain FR1 region; a light chain CDR1 of a selected anti-GIPR antibody; a light chain FR2 region; a light chain CDR2 of a selected anti-GIPR antibody; a light chain FR3 region; a light chain CDR3 of a selected anti-GIPR antibody; optionally a light chain FR4 region; a linker region; optionally a heavy chain FR1 region; a heavy chain CDR1 of a selected anti-GIPR antibody; a heavy chain FR2 region; a heavy chain CDR2 of a selected anti-GIPR antibody; a heavy chain FR3 region; a heavy chain CDR3 of a selected anti-GIPR antibody; and a heavy chain FR4 region. In some of these embodiments, each of the FR regions is a human FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO:115) and $GGGS_n$ (SEQ ID NO:116), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGSG (SEQ ID NO:117), GGSGG (SEQ ID NO:118), GSGSG (SEQ ID NO:119), GSGGG (SEQ ID NO:120), GGGSG (SEQ ID NO:121), GSSSG (SEQ ID NO:122), and the like. The ordinarily skilled artisan will recognize that design of a peptide conjugated to any elements described above can include linkers that are all or partially flexible, such that the linker can include a flexible linker as well as one or more portions that confer less flexible structure.

The antibodies shown in FIGS. 9 and 10 are already chicken sequences. In some embodiments, a subject antibody may be "humanized." The term "humanized antibody" refers to an antibody comprising at least one chain comprising variable region framework residues substantially from a human antibody chain (referred to as the acceptor immunoglobulin or antibody) and at least one CDR substantially from a a non-human antibody (referred to as the donor immunoglobulin or antibody). See, Queen et al., Proc. Natl. Acad. Sci. USA 86:10029 10033 (1989), U.S. Pat. Nos. 5,530,101, 5,585,089, 5,693,761, WO 90/07861, and U.S. Pat. No. 5,225,539. The constant region(s), if present, can also be substantially or entirely from a human immunoglobulin. In some embodiments, a subject antibody comprises one or more of the CDRs and one or more FR regions from a human antibody. Methods of making humanized antibodies are known in the art. See, e.g., U.S. Pat. No. 7,256,273.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, a subject antibody comprises scFv multimers. For example, in some embodiments, a subject antibody is an scFv dimer (e.g., comprises two tandem scFv (scFv$_2$)), an scFv trimer (e.g., comprises three tandem scFv (scFv$_3$)), an scFv tetramer (e.g., comprises four tandem scFv (scFv$_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., (Gly)$_x$, where x is an integer from 2 to 10. Other suitable linkers are those discussed above. In some embodiments, each of the scFv monomers in a subject scFV multimer is humanized, as described above.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to an the subject antibody that comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetyl-glucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula R(O—CH$_2$—CH$_2$)$_n$ O—R, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., comprise a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866, 132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-dephenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from Aequoria victoria or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) Nature Biotechnol. 17:969-973; and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., CYPYDVPDYA; SEQ ID NO:123), FLAG (e.g., DYKDDDDK; SEQ ID NO:124), c-myc (e.g., CEQKLISEEDL; SEQ ID NO:125), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:126), HisX6 (HHHHHH) (SEQ ID NO:127), C-myc (EQKLISEEDL) (SEQ ID NO:128), Flag (DYKDDDDK) (SEQ ID NO:124), StrepTag (WSHPQFEK) (SEQ ID NO:129), hemagglutinin, e.g., HA Tag (YPYDVPDYA; SEQ ID NO:130), glutathinone-S-transferase (GST), thioredoxin, cellulose binding domain, RYIRS (SEQ ID NO:131), Phe-His-His-Thr (SEQ ID NO:132), chitin binding domain, S-peptide, T7 peptide, SH2 domain, C-end RNA tag, WEAAAREACCRECCARA (SEQ ID NO: 133), metal binding domains, e.g., zinc binding domains or calcium binding domains such as those from calcium-binding proteins, e.g., calmodulin, troponin C, calcineurin B, myosin light chain, recoverin, S-modulin, visinin, VILIP. neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

A subject antibody will in some embodiments be fused to a polypeptide that binds to an endogenous blood brain barrier (BBB) receptor. Linking a subject antibody to a polypeptide that binds to an endogenous BBB receptor facilitates crossing the BBB, e.g., in a subject treatment method (see below) involving administration of a subject antibody to an individual in need thereof. Suitable polypeptides that bind to an endogenous BBB include antibodies, e.g., monoclonal antibodies, or antigen-binding fragments thereof, that specifically bind to an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-deaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_XH_YN_Z$, can be cyclic or acyclic, branched or unbranched, hydrocarbon chains of 3-12 carbon atoms that further include 1-6 NR or $N(R)_2$ moieties, wherein R is H, $(C_1-C_4)$ alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

Methods of Producing a Subject Antibody

A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A et al. 2005 *Protein Pept. Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella*, *Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/tre hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject antibody. A subject nucleic acid can comprise a nucleotide sequence encoding heavy- and light-chain CDRs. In some embodiments, a subject nucleic acid comprises a nucleotide sequence encoding heavy- and light-chain CDRs, where the CDR-encoding sequences are interspersed with FR-encoding nucleotide sequences. In some embodiments, the FR-encoding nucleotide sequences are human FR-encoding nucleotide sequences.

Cells

The present disclosure provides isolated genetically modified host cells (e.g., in vitro cells) that are genetically modified with a subject nucleic acid. In some embodiments, a subject isolated genetically modified host cell can produce a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, Hela cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Neurospora crassa, Chlamydomonas reinhardtii,* and the like.

Suitable prokaryotic cells include, but are not limited to, any of a variety of laboratory strains of *Escherichia coli, Lactobacillus sp., Salmonella sp., Shigella sp.,* and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium.* Suitable *Shigella* strains include, but are not limited to, *Shigella flexneri, Shigella sonnei,* and *Shigella disenteriae.* Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus sp.,* and the like. In some embodiments, the host cell is *Escherichia coli.*

Formulations and Pharmaceutical Compositions

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in weight or blood glucose. Generally, the desired result is at least a reduction in a symptom of a metabolic disorder or condition as compared to a control. A subject antibody can be delivered in such a manner as to avoid the blood-brain barrier, as described in more detail below. A subject antibody can be formulated and/or modified to enable the antibody to cross the blood-brain barrier, if necessary. A treatment involves administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with the subject invention. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pennsylvania, 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, Novel Drug Delivery Systems, 1992 (Marcel Dekker, Inc.). Some of these formulations are discussed herein.

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

In some embodiments, the antibody can be administered to the patient as an intravenous infusion (200 mg or 2 mg/kg, up to 200 mg) over 10-60 (e.g., 30 minutes), every 2-4 (e.g., three) weeks in a pharmaceutically acceptable carrier, e.g., PBS.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as metabolic disorder or condition. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Treatment Methods

As noted above, the present disclosure provides a method of treating a metabolic disorder, such as a disorder of glucose metabolism (e.g. Type 2 diabetes, elevated glucose levels, elevated insulin levels, dyslipidemia, metabolic syndrome (Syndrome X or insulin resistance syndrome), glucosuria, metabolic acidosis. Type 1 diabetes, obesity and conditions exacerbated by obesity) by blocking or interfering with the biological activity of GIP. In one embodiment, a therapeutically effective amount of a subject antibody is administered to a subject in need thereof. Methods of administration and delivery are also provided A subject antibody can be used to treat, diagnose or ameliorate, a metabolic condition or disorder. In one embodiment, the metabolic disorder to be treated is diabetes, e.g., type 2 diabetes. In another embodiment, the metabolic condition or disorder is obesity. In other embodiments the metabolic condition or disorder is dyslipidemia, elevated glucose levels, elevated insulin levels or diabetic nephropathy. For example, a metabolic condition or disorder that can be treated or ameliorated using a subject antibody includes a state in which a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a subject antibody can also be found in the American Diabetes Association Standards of Medical Care in Diabetes Care-2011, American Diabetes Association, Diabetes Care Vol. 34, No. Supplement 1, S11-S61, 2010, incorporated herein by reference.

A metabolic disorder or condition, such as Type 2 diabetes, elevated glucose levels, elevated insulin levels, dyslipidemia, obesity or diabetic nephropathy, can be treated by administering a therapeutically effective dose of a subject antibody to a patient in need thereof. The administration can be performed as described herein, such as by IV injection, intraperitoneal (IP) injection, subcutaneous injection, intramuscular injection, or orally in the form of a tablet or liquid formation. In some situations, a therapeutically effective or preferred dose of a subject antibody can be determined by a clinician. A therapeutically effective dose of subject antibody will depend, inter alia, upon the administration schedule, the unit dose of agent administered, whether the subject antibody is administered in combination with other therapeutic agents, the immune status and the health of the recipient. The term "therapeutically effective dose," as used herein, means an amount of subject antibody that elicits a biological or medicinal response in a tissue system, animal, or human being sought by a researcher, medical doctor, or other clinician, which includes alleviation or amelioration of the symptoms of the disease or disorder being treated, i.e., an amount of a subject antibody that supports an observable level of one or more desired biological or medicinal response, for example lowering blood glucose, insulin, triglyceride, or cholesterol levels; reducing body weight; or improving glucose tolerance, energy expenditure, or insulin sensitivity.

It is noted that a therapeutically effective dose of a subject antibody can also vary with the desired result. Thus, for example, in situations in which a lower level of blood glucose is indicated a dose of subject antibody will be correspondingly higher than a dose in which a comparatively lower level of blood glucose is desired. Conversely, in situations in which a higher level of blood glucose is indicated a dose of subject antibody will be correspondingly lower than a dose in which a comparatively higher level of blood glucose is desired. In various embodiments, a subject is a human having a blood glucose level of 100 mg/dL or greater can be treated with a subject antibody.

In one embodiment, a method of the instant disclosure comprises first measuring a baseline level of one or more metabolically-relevant compounds such as glucose, insulin, cholesterol, lipid in a subject. A pharmaceutical composition comprising a subject antibody is then administered to the subject. After a desired period of time, the level of the one or more metabolically-relevant compounds (e.g., blood glucose, insulin, cholesterol, lipid) in the subject is again measured. The two levels can then be compared in order to determine the relative change in the metabolically-relevant compound in the subject. Depending on the outcome of that comparison another dose of the pharmaceutical composition comprising a subject antibody can be administered to achieve a desired level of one or more metabolically-relevant compound.

It is noted that a pharmaceutical composition comprising a subject antibody can be co-administered with another compound. The identity and properties of compound co-administered with the GIPR binding protein will depend on the nature of the condition to be treated or ameliorated. A non-limiting list of examples of compounds that can be administered in combination with a pharmaceutical composition comprising a GIPR binding protein include rosiglitizone, pioglitizone, repaglinide, nateglitinide, metformin, exenatide, stiagliptin, pramlintide, glipizide, glimeprirideacarbose, and miglitol.

Also provided are kits for practicing the disclosed methods. Such kits can comprise a pharmaceutical composition such as those described herein, including nucleic acids encoding the peptides or proteins provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a subject antibody; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, obesity, type 2 diabetes, dyslipidemia or diabetic nephropathy.

Instructions can be printed on a substrate, such as paper or plastic, etc., and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded.

Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

In some embodiments, an effective amount of a subject antibody is an amount that, when administered alone (e.g., in monotherapy) or in combination (e.g., in combination therapy) with one or more additional therapeutic agents, in one or more doses, is effective to reduce an adverse symptom of a metabolic disorder or condition by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the severity of the adverse symptom in the absence of treatment with the antibody.

Subjects Suitable for Treatment

A variety of subjects are suitable for treatment with a subject method. Suitable subjects include any individual, e.g., a human, who has a metabolic disorder or condition, who has been diagnosed with a metabolic disorder or condition, who is at risk for developing a metabolic disorder or condition, who has had a metabolic disorder or condition and is at risk for recurrence of the metabolic disorder or condition, or who is recovering from a metabolic disorder or condition.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Summary

Raising functional antibodies against G protein-coupled receptors can be challenging due to their low density expression, instability in the absence of the cell membrane's lipid bilayer and frequently short extracellular domains that can serve as antigens. In addition, a particular therapeutic concept may require an antibody to not just bind the receptor but also act as a functional receptor agonist or antagonist. Antagonizing the Glucose-dependent Insulinotropic Polypeptide (GIP) Receptor may open up new therapeutic modalities in the treatment of diabetes and obesity. As such, a panel of monoclonal antagonistic antibodies would be a useful tool for in vitro and in vivo studies and as therapeutics. The receptor is highly conserved between rodents and humans, which has contributed to previous mouse and rat immunization campaigns generating very few usable antibodies. Switching the immunization host to chicken, which is phylogenetically distant from mammals, enabled raising a large and diverse panel of monoclonal antibodies containing 172 unique sequences. Three quarters of all chicken-derived antibodies were functional antagonists, exhibited high-affinities to the receptor extracellular domain and sampled a broad epitope repertoire. For difficult targets, including GPCRs such as GIPR, chickens are emerging as valuable immunization hosts for therapeutic antibody discovery.

In the following study, chicken immunization to obtain antagonistic antibodies against GIPR and compare those to antibodies previously raised in mice and rats. The data shows that for GIPR, chickens were the superior host, resulting in a larger number of antibodies, a higher frequency of functional antagonists and antibodies covering a broader epitope space.

Results

Enriching for Species Cross Reactive Clones with Immunization and Screening Strategies Initially GEM screens were performed with lymphocytes from chicken 11272 (hGIPR-Fc immunization) using cellular reporters, parental CHO cells dyed blue with vital dye and CHO cells stably expressing mGIPR. This cellular reporter GEM screen yielded a high frequency of species cross-reactive clones (38% cross-reactive). Secondly, lymphocytes from chicken 11272 were used in GEM screens with reporter beads featuring hGIPR-Fc and hFc were coated onto white or blue beads, respectively. The reporter bead GEM screen was not as efficient as the cellular screen in obtaining species cross-reactive clones (4.8% cross-reactive). Therefore going forward cellular reporters were used when GEM screens were set up for the remaining chicken lymphocytes.

Large and Diverse Antibody Panels Generated to GIPR

A total of 694 clones were generated from the chicken immunization. Of those, 462 were unique sequences. 206 were cross-reactive with human, cyno, murine and/or rat GPCR and were moved along the screening cascade to EC50 determinations. 125 clones had an EC50 on human GPCR expressing CHO cells that were within 4 fold of the control antibody. A total of 172 unique clones were advanced to further study.

Figure 1:
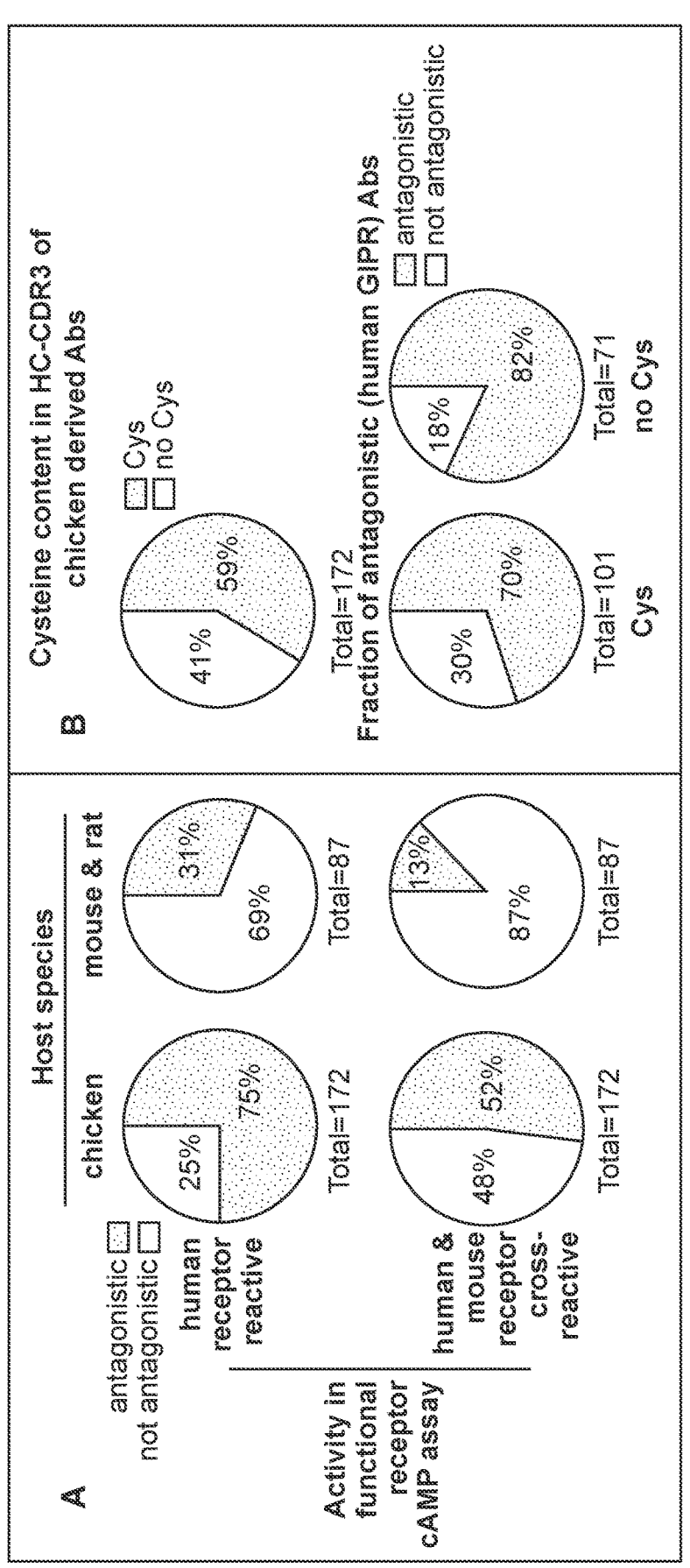
FIG. 1: Anti-GIPR antibodies raised in chicken vs. mouse and rat hybridoma antibodies. Panel A illustrates the number and functional activity (antagonism as measured in GIPR specific cAMP assay) of anti-GIPR antibodies raised in chicken versus previous campaigns using classic mouse and rat hybridoma technology. In panel B, the chicken antibodies are broken down into those containing cysteines in the CDR3 of the heavy chain (Cys) and those without (no Cys) while also giving the fraction of antagonistic versus not antagonistic antibodies in each population.

Immunizing Chickens with GIPR Yields More Antagonistic Antibodies Than Classic Hybridoma Technology Using Mouse and Rat as Host Species The chicken immunization campaign yielded a total of 172 antibodies with unique sequences that were screened for functional activity, i.e. their ability to antagonize GIPR in a cAMP assay in vitro. In comparison, classic mouse and rat immunizations in conjunction with hybridoma technology, resulted in just 87 hybridoma supernatant samples whose activity could be assessed (FIG. 1A). Notably, multiple prior rodent immunization campaigns, which used a combination of GIPR cDNA, GIPR-Fc fusion protein and cell lines overexpressing GIPR as antigen and employed both GIPR$^{+/+}$ and GIPR$^{-/-}$ host strains, failed to produce antagonistic anti-GIPR antibodies.

Among the chicken derived antibodies, 129 (75%) were tested to be antagonistic in a human-GIPR specific assay whereas 82 (48%) showed additional murine cross-reactivity by also exhibiting antagonistic behavior in a mouse-GIPR specific assay. For the population of hybridoma antibodies raised in mouse and rat, this fraction was only 31% (27) and 13% (11), respectively. During the antibody generation process, each chicken antibody was sequenced and only unique sequences were taken forward.

One feature of chicken antibodies is the presence of non-canonical cysteine residues in the CDR3 region of the heavy chain. These cysteine residues can potentially form intra-chain disulfide bonds, and are particularly likely to occur in long CDR3s, where they are thought to play a role in stabilizing the secondary structure of the CDR3 loop.[20] Among the population of GIPR antibodies tested in this work, 101 (59%) contained cysteines in the HC-CDR3 (FIG. 1B). The presence of cysteines, however, had no apparent impact on the likelihood of an antibody exhibiting antagonistic behavior in the GIPR cAMP assay. 71 (70%) and 58 (82%) of the antibodies possessed antagonistic activity among the cysteine-containing and cysteine-free antibody populations, respectively.

The antibodies used in this work were derived from 5 chickens (Table 1). The likelihood of antibody antagonism and the fraction of antibodies containing HC-CDR3 cysteines varied considerably by the host chicken, suggesting multiple chickens should be used in each immunization to obtain the best possible antibody diversity.

Chicken Antibodies Reveal a Wide Range of Affinities to Human and Murine GIPR

Figure 2:
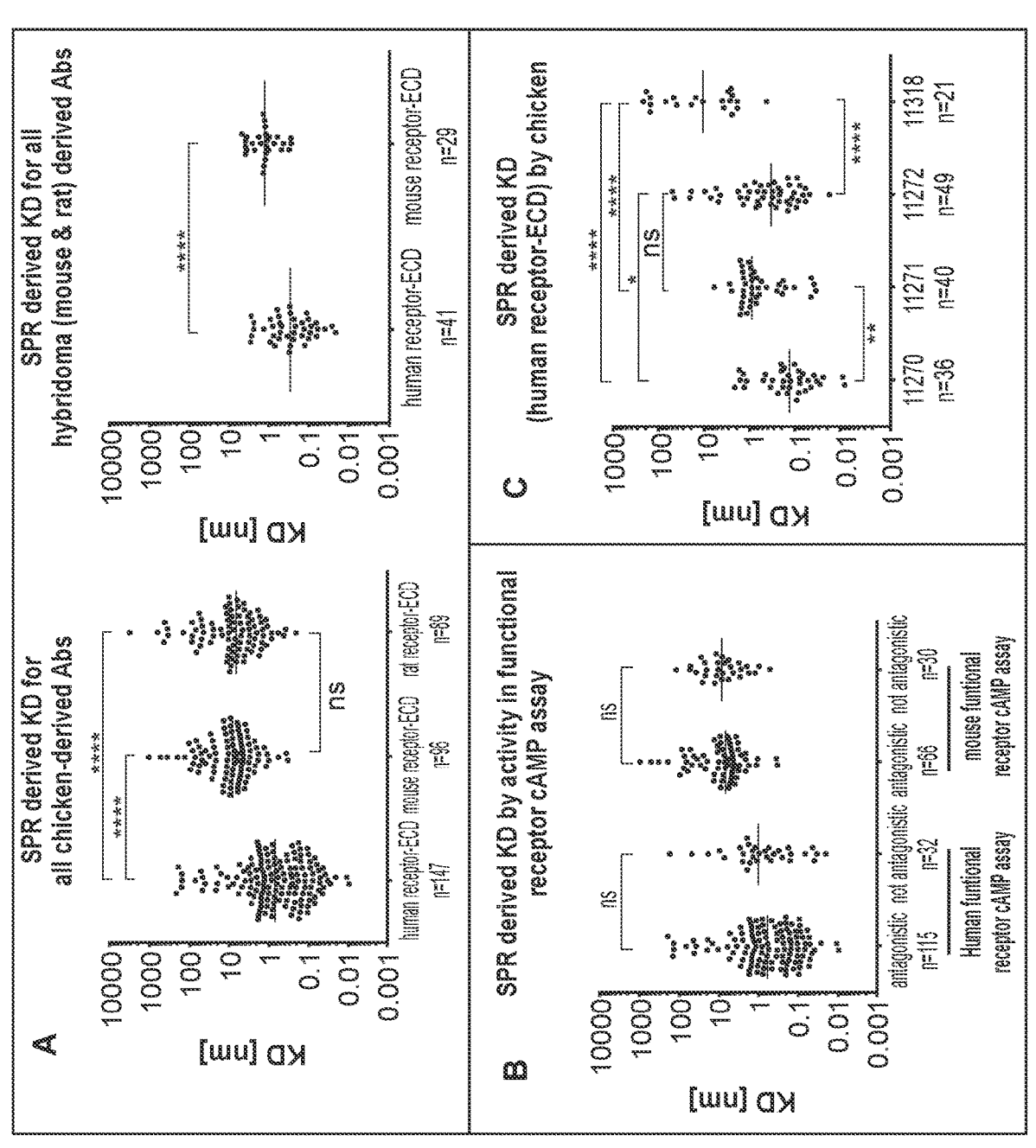
FIG. 2: Affinity data measured by surface plasmon resonance (SPR) for anti-GIPR antibodies. Panel A summarizes the SPR derived KD values for anti-GIPR antibodies. The left hand side shows chicken-derived antibody affinities against human. mouse and rat-GIP receptor extracellular domain (ECD), whereas the right hand side provides human and mouse GIP receptor ECD affinities for the legacy mouse and rat hybridoma campaigns for comparison. All affinities are shown, irrespective of whether an antibody is antagonistic or not. Panel B breaks down the KD values by the antagonistic activity of the chicken derived antibodies in human or mouse receptor G specific functional cAMP assays. In Panel C. antibody KD values are grouped by the host chicken, whereas panel D lists chicken derived antibody affinities based on whether or not they contain a cysteine in the heavy chain CDR3 (left hand side) as well as by functional activity against human and mouse GIPR and cysteine content (right hand side). The red lines indicate the population medians. P-values were calculated using Kruskal-Wallis and Mann-Whitney tests. ns—not significant; *$p<0.05$; $p<0.01$; *$p<0.001$; ****$p<0.0001$.
Figure 2:
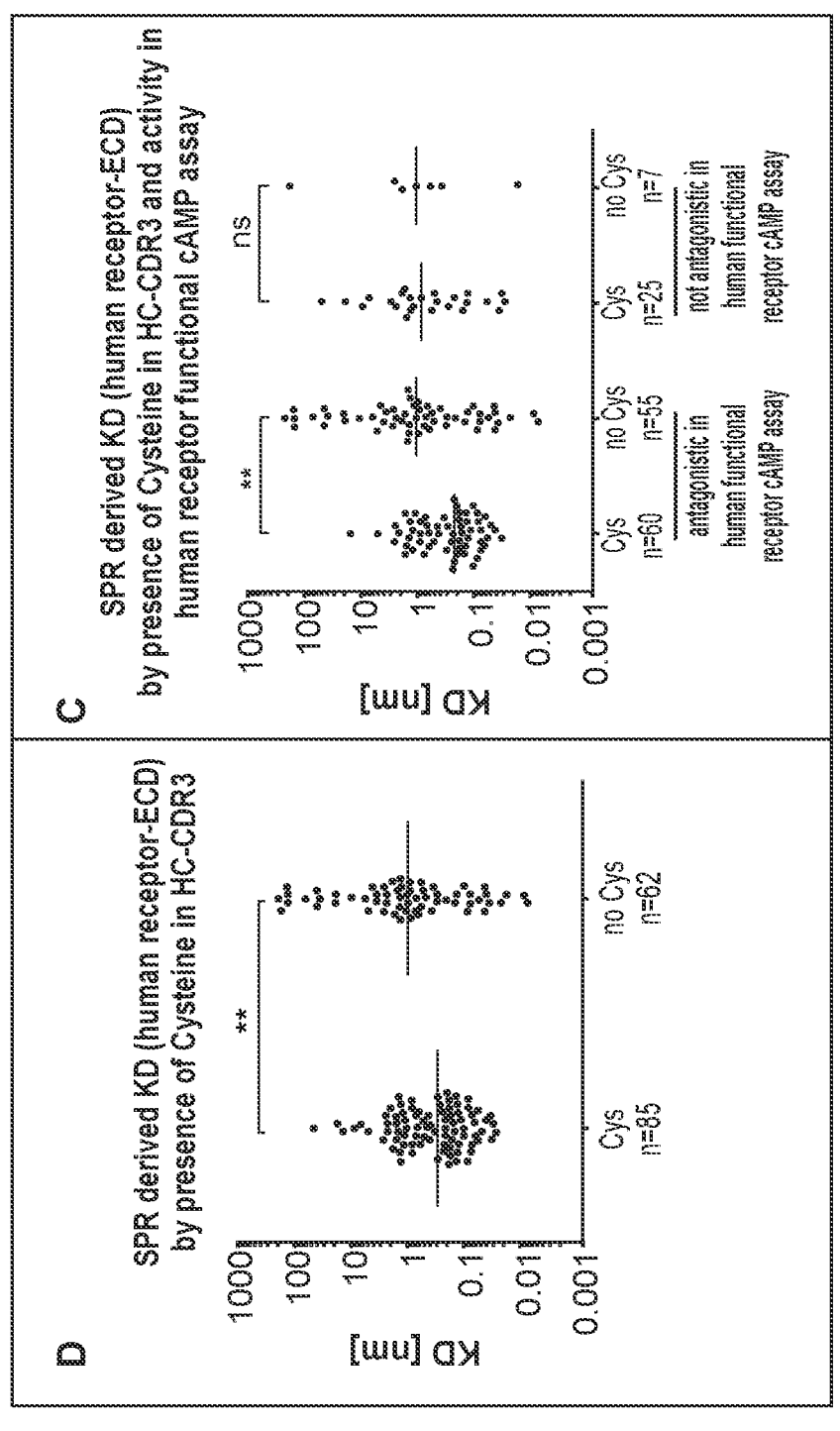

The KD values of GIPR antibodies against human, mouse and rat recombinant antigen (using immobilized extracellular domain protein, see Material & Methods) were determined by surface plasmon resonance (FIG. 2). Affinities against all species antigens were spread over several orders of magnitude (FIG. 2A). The chicken derived antibodies (FIG. 2A, left panel) showed significantly higher affinities—i.e. lower KD values—for human (median 0.7 nM; range 0.009 nM-212 nM) than for either mouse (median 8.1 nM; range 0.3 nM-1043 nM) or rat (median 6.7 nM; range 0.2 nM-3110 nM) antigens. The same trend was present for the mouse and rat hybridoma antibodies (FIG. 2B, right panel), which were assessed against human (median 0.3 nM; range 0.02 nM-3.0 nM) and mouse (median 0.9 nM; range 0.3 nM-5.2 nM) GIPR antigen. The absolute KD values between chicken and hybridoma derived antibodies, however, are not comparable, as they were captured on separate chips due to possessing different Fc domains (murine or rat for hybridoma supernatants and human for chicken derived Abs, see Material & Methods).

Among the chicken antibody population, antigen affinity was not correlated to functional antagonistic activity in either the human or mouse-GIPR CAMP assay (FIG. 2B). The individual host chicken, however, had a strong impact (FIG. 2C). Animal 11270 produced antibodies with the lowest KD values against human GIPR antigen (median 0.2 nM; range 0.009 nM-2.3 nM), whereas bird 11318 yielded antibodies with the highest KD (median 0.9 nM; range 11.1 nM-212 nM). Antibody populations obtained from animals 11271 (median 1.0 nM; range 0.03 nM-6.4 nM) and 11272 (median 0.4 nM; range 0.02 nM-51.2 nM) occupied an intermediate position in affinity and were comparable to each other.

Against the human GIPR antigen, the cysteine containing antibodies displayed a lower median KD (0.3 nM) than the cysteine free group (1.2 nM) (FIG. 2D. left panel). However, the antibodies with the lowest overall KD were found in the cysteine-free group, which exhibited a wider spread of measured KDs (range: 0.009 nM-212 nM) than the cysteine containing population (range: 0.03 nM-51.2 nM). When additionally grouping the chicken derived antibodies by their activity profile (FIG. 2D, right panel), the median KD of the cysteine containing population was only lower in the antagonistic group, whereas no difference was observed for cysteine containing versus cysteine free antibodies that fail to antagonize GIPR.

Figure 3:
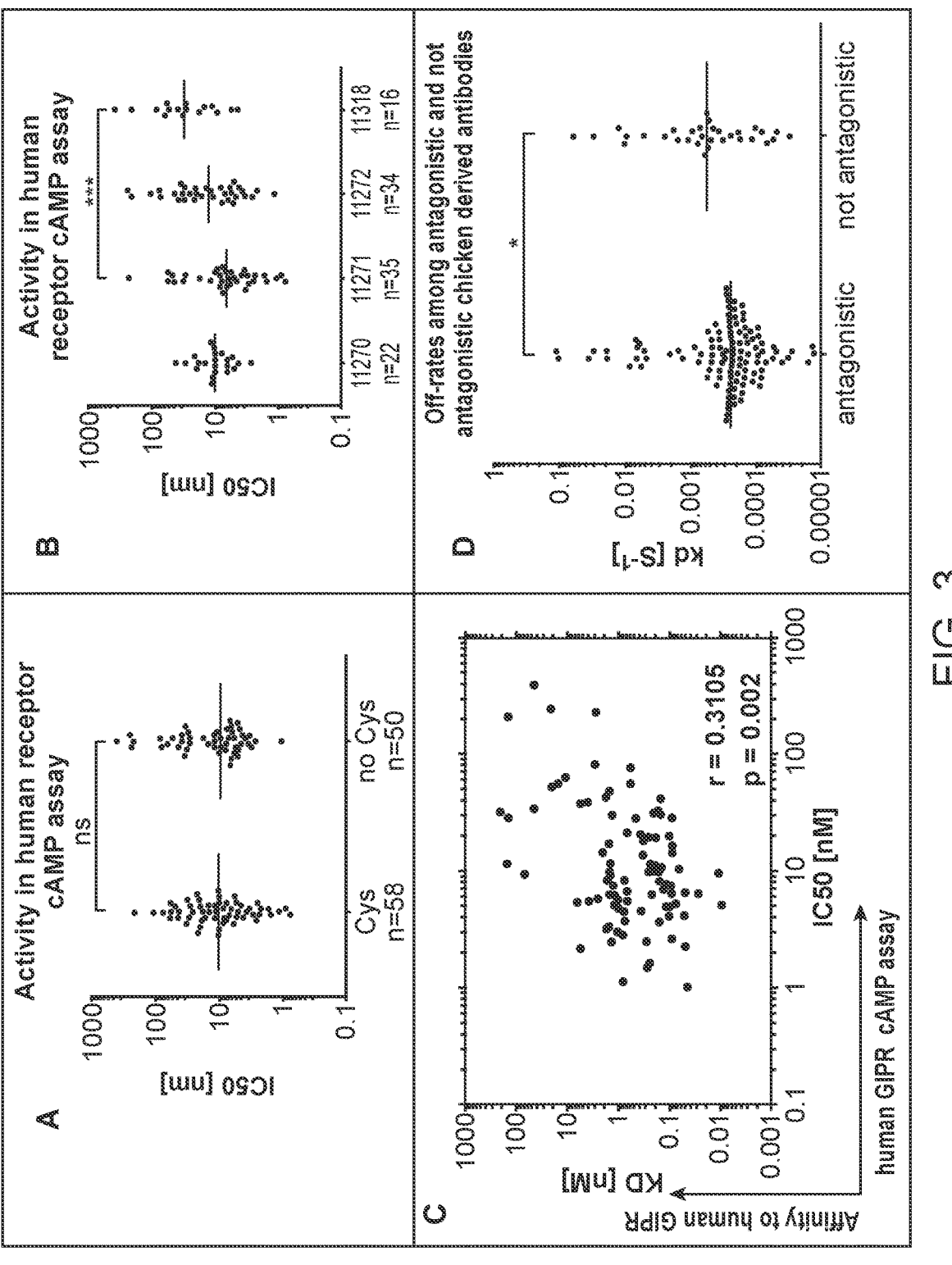
FIG. 3: Functional activity of chicken-derived anti-GIPR antibodies in cAMP assay. IC50 values for the chicken derived Abs were determined using an Alphascreen cAMP assay. A illustrates obtained values for functional antibodies broken down by cysteine content, whereas B illustrates antibodies raised in different chicken. C shows a correlation plot of the KD values versus the IC50. The red lines indicate the population medians. P-values were calculated using Kruskal-Wallis and Mann-Whitney tests. ns—not significant; *$p<0.05$; $p<0.01$; *$p<0.001$; ****$p<0.0001$.
Figure 4:
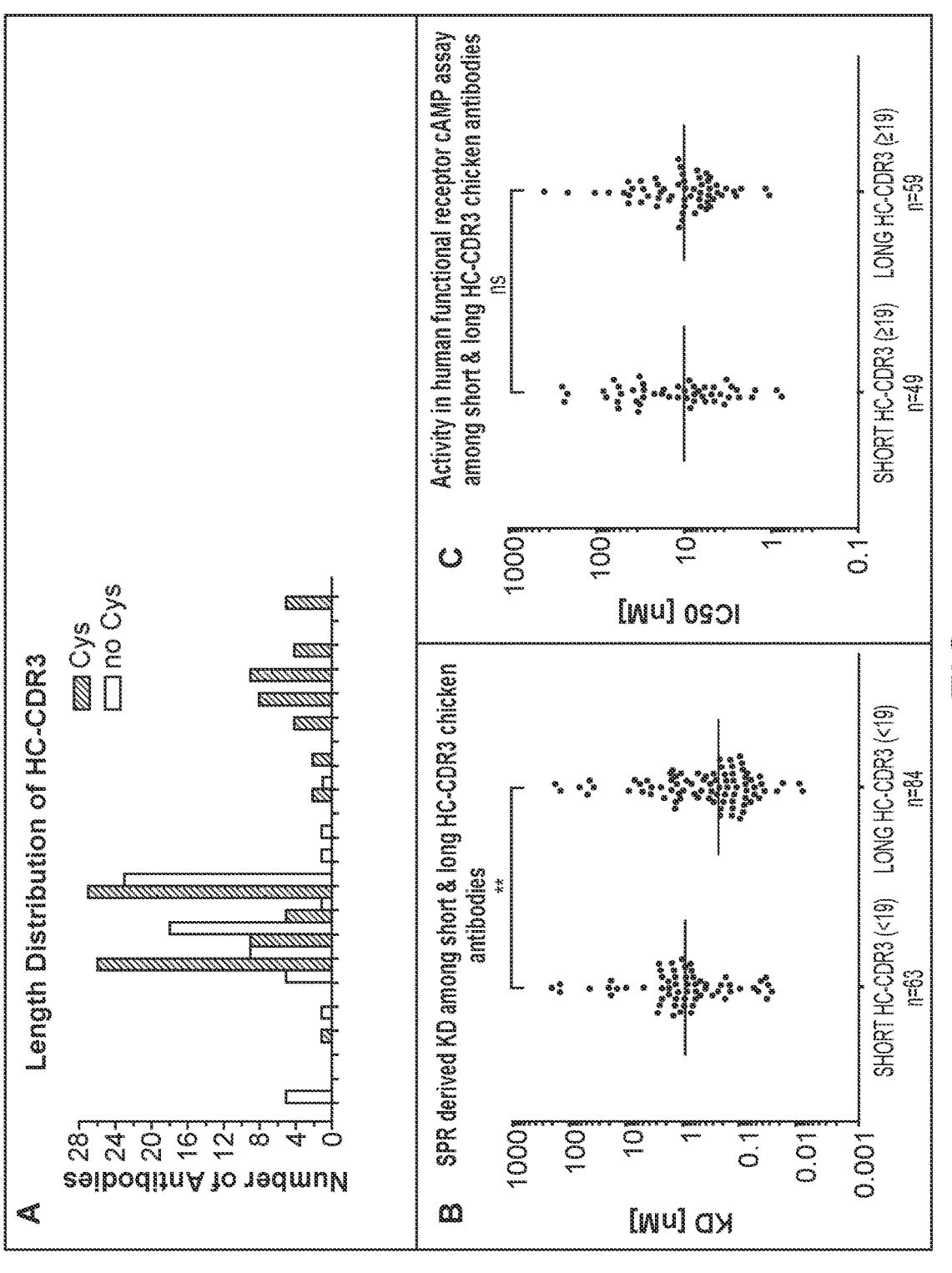
FIG. 4. HC-CDR3 length of anti-GIPR chicken antibodies and effect on affinity and function. The histogram (A) lists the HC-CDR3 length distribution of cysteine-containing (black bars) vs. cysteine-free (gray bars) chicken-derived anti-GIPR antibodies. (B and C) list the affinities (KD) and antagonistic activities (IC50) among antibodies with short ($<19$ amino acids) vs. long ($>=19$ amino acids) CDR3 sequences, respectively. The red lines indicate the population median. P-values were calculated using the Mann-Whitney test. ns—not significant; **$p<0.01$.

The IC50 of the Functional Antagonistic GIPR CAMP Assay is not Correlated to the Presence of Cysteines and Shows Weak Correlation to the Affinity The functional activity of chicken derived anti-GIPR antibodies was assessed using an AlphaScreen based cAMP in vitro assay (FIG. 3). Briefly, GIPR expressing cells are stimulated with the endogenous ligand GIP and the resulting cAMP production is quantified. Antagonistic antibodies are characterized by their ability to block the generation of cAMP. The IC50 [nM] of antagonistic antibodies was not impacted by the presence (median 10.0 nM; range 0.75 nM-211.3 nM) or absence (median 9.4 nM; range 1.3 nM-389.6 nM) of cysteines in the HC-CDR3 (FIG. 3A). The host chicken had some impact on the observed strength of functional antagonism (FIG. 3B), however the differences are only statistically significant for chicken 11271 (median 6.5 nM) versus 11318 (Median 30.8 nM), but not for other comparisons (medians: 11270: 10.0 nM; 11272: 12.7 nM).

Figure 6:
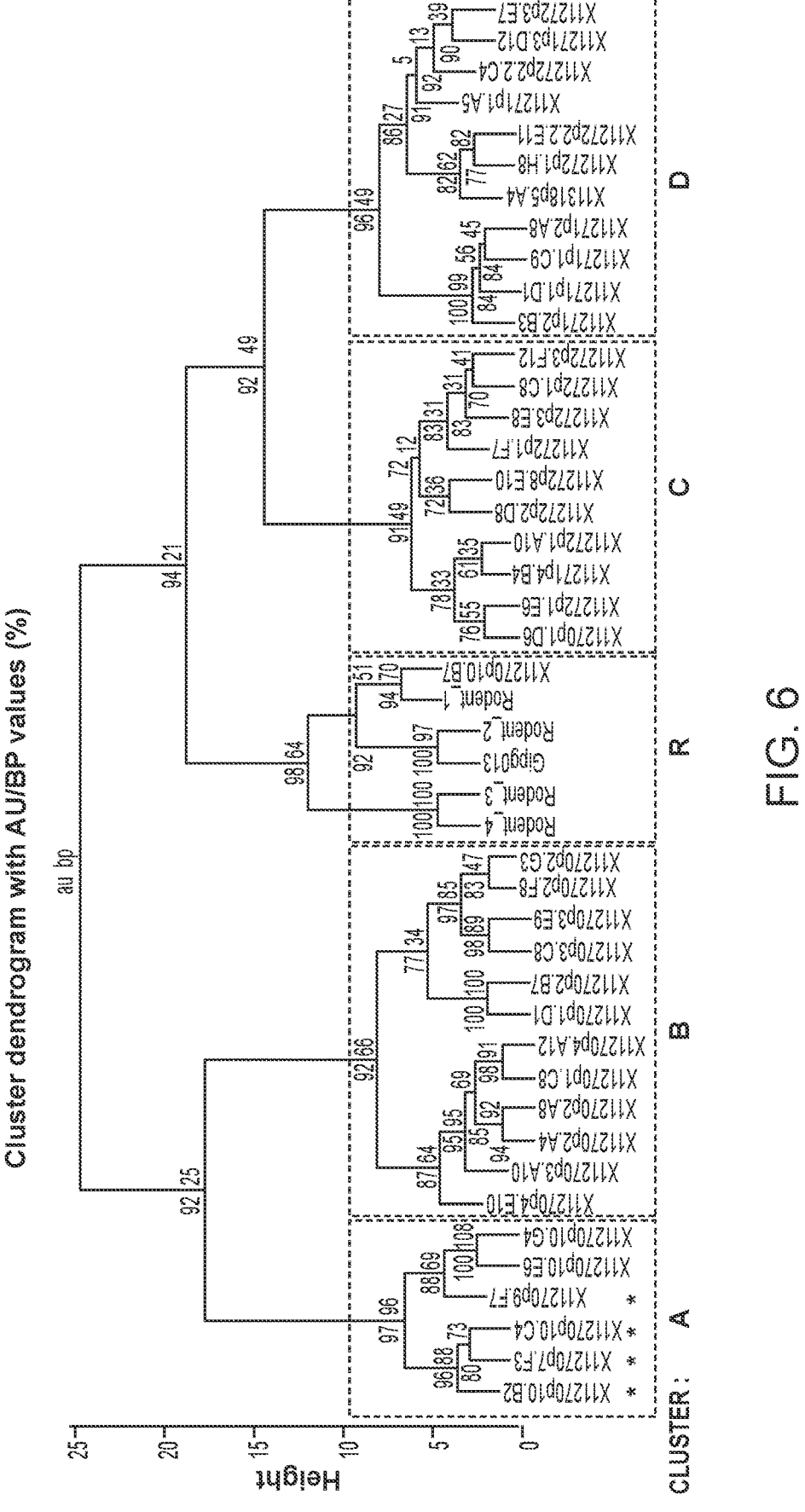
FIG. 6: Dendrogram of BLI epitope clustering data. The dendrogram representing clustering of the secondary antibodies was generated in pvclust (see Materials & Methods). The axis on the left (Height) serves as a measure for antibody dissimilarity. Using a height cut-off of 10 (dashed red line), 5 antibody clusters (A, B, C, D, R—red dashed boxes) emerge. The AU value (%) represents the approximate unbiased p-value computed by pvclust using multiscale bootstrap resampling. Clusters with high AU values are strongly supported by the data. * denominates non-antagonistic antibodies.

Biolayer Interferometry Clustering Reveals a Larger Epitope Diversity Among the Chicken Derived Antibodies than Antibodies from Other Sources Biolayer interferometry based clustering using the Fortebio Octet HTX platform was used to assess the epitope diversity of 40 chicken derived antibodies as well as four rodent raised antibodies and one phage display antibody (Gipg013) previously described in the literature[17] (FIGS. 5 & 6, Table 3). Briefly, biotinylated human-GIPR ECD was immobilized on streptavidin biosensors and saturated by binding all anti-GIPR antibodies in a first step. In a second step, all antibodies are tested for their ability to bind the GIPR-antibody 1 complex. Additional binding indicates the recognition of a distinct epitope. The clustering result, shown as a two-dimensional matrix (analysis based on method adapted from Liao-Chan et al[21]) is represented in FIG. 6. The primary antibodies are shown in columns, the secondary antibodies in rows. Rows are sorted according to their Pearson correlation coefficient so that similar antibodies are located next to each other. The column sorting was adapted to match the row sorting—which results in all self-blocking antibody combinations to be located on the diagonal (highlighted in red). The color gradient from blue (0) to white (100) was applied to highlight blocking or additional binding. Further the unsorted matrix was analyzed using pvclust in R.[22, 23] Pvclust provides hierarchical clustering of the BLI data (secondary antibodies only, FIG. 6). The 'Height' axis provides a measurement for antibody similarity. Using a cut-off of '10', 5 different epitope clusters emerge: A, B, C, D and R. The AU value (%) represents the approximate unbiased p-value computed by pvclust using multiscale bootstrap resampling. Clusters with high AU values are strongly supported by the data. Notably, all four rodent derived antibodies (Rodent_1-4) and the phage display antibody Gipg013 cross-compete for binding to the GIPR-ECD and thus fall in the same cluster (R). Hence, they recognize either the same epitope or their epitopes are overlapping in a manner that prevents parallel binding. One chicken-derived antibody (11270p10. B7) can also be found in that cluster. The emergence of the additional clusters (A-D) reveals that there are likely additional epitopes on the GIPR-ECD that could only be accessed via chicken immunization. Notably, the epitope clustering matrix (FIG. 5) is not fully symmetrical. For example, for chicken derived Abs 34 (11271p1. D1) and 14 (11270p3. C8) cross-blocking depends on the order in which the antibodies are used. When number 34 is used as the primary and 14 as the secondary antibody, additional binding is observed (normalized binding signal 128). When using 14 first and 34 second, however, cross-blocking (binding signal 25) occurs. These discrepancies may occur when the primary antibody is able to induce conformational changes in the antigen that either enables or blocks binding by a secondary antibody. Elucidating the structural basis for this antibody-GIPR binding behavior will require further research.

Figure 7:
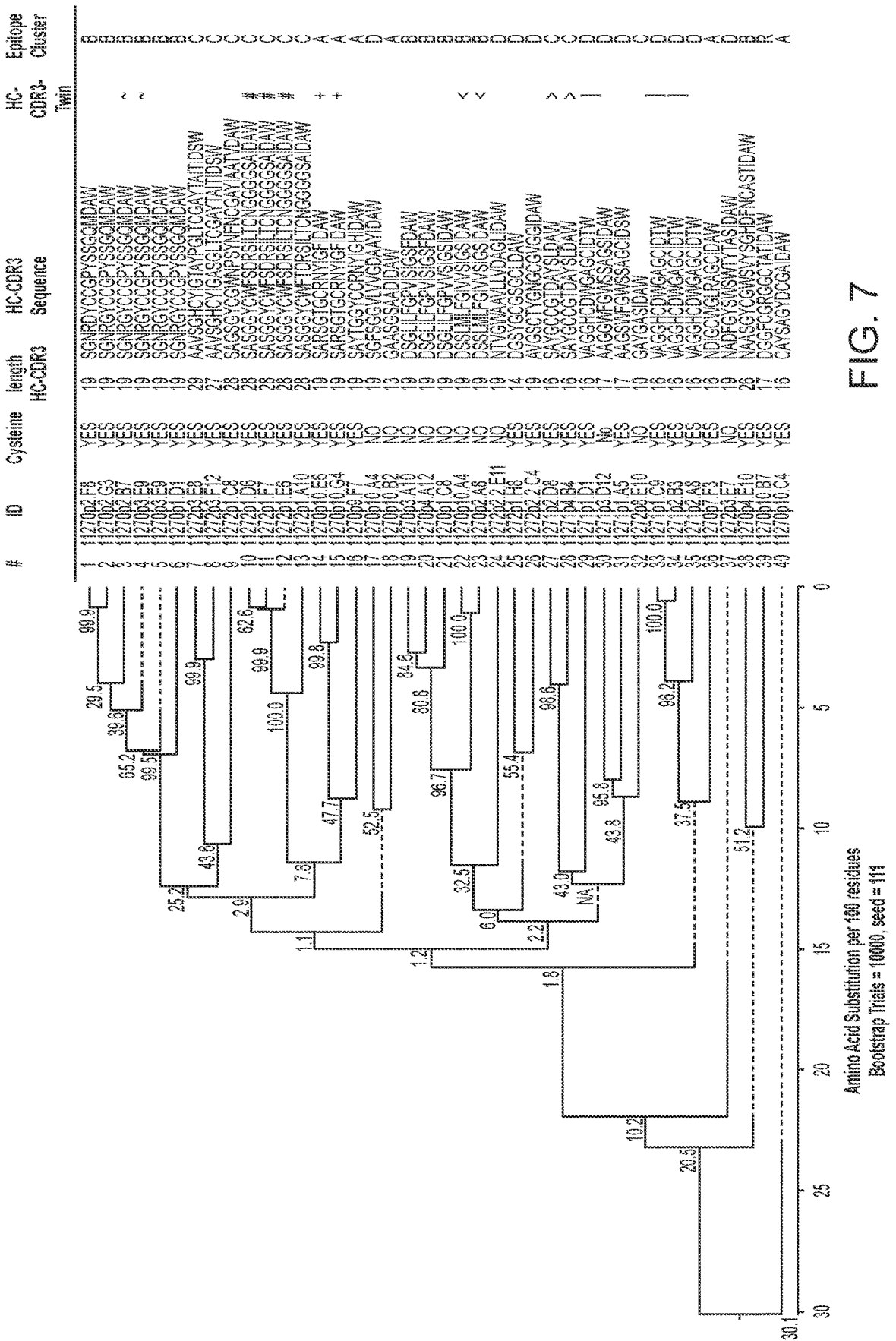
FIG. 7: Phylogenetic tree of 40 chicken derived anti-receptor G antibodies and cluster assignment. The phylogenetic tree (left panel) for the 40 chicken derived anti-receptor G antibodies used for epitope clustering was generated in MegAlign using ClustalW alignment of all full length VH sequences. Bootstrap percentage values are shown on each node. The table (right panel) lists antibody IDs, presence of cysteines, antagonistic activity as well as length and amino acid sequence of the HC-CDR3 (from top to bottom SEQ ID NOS: 1-3, 3, 4-9, 9, 9, 10, 11, 11, 12-15, 15, 16-17, 17, 18-21, 21, 22-25, 22, 22, 26-31). The symbols in the penultimate column indicate antibodies with identical HC-CDR3s. The last column lists the BLI epitope cluster assignment derived from the dendrogram shown in FIG. 6.

Among the Chicken Derived Antibodies, the Epitope Cluster is Closely Correlated to the Heavy Chain CDR3 Sequence and Function In order to validate our BLI based epitope clustering approach (FIGS. 5 & 6), we also analyzed the VH sequences of the 40 chicken-derived antibodies using ClustalW alignement[24] and MegAlign (DNAStar) for phylogenetic tree construction (FIG. 7). It became apparent that antibodies that fell into the same BLI derived epitope cluster are characterized by similar HC-CDR3 sequences. Antibodies with identical HC-CDR3 (denoted as twins) always belong to the same epitope cluster. Notably, each epitope cluster contained both cysteine-containing and cysteine-free antibodies suggesting that epitope diversity among chicken-derived antibodies is independent of the HC-CDR3 cysteines.

Due to our focus on functionally antagonistic anti-GIPR antibodies, only 4 out of the 40 tested chicken antibodies in the epitope clustering analysis were from the non-antagonistic population. However, all of them fell within the same cluster (cluster A), highlighting a correlation between the epitope and anti-GIPR antibody function.

Tables

TABLE 1

| Numerical representation of chicken derived anti-GIPR antibodies | | | |
|---|---|---|---|
| Chicken ID | Total No. of Abs Cys (%)/no Cys (%) | Antagonistic (%) Cys (%) | Not antagonistic (%) Cys (%) |
| 11270 | 36 | 27 (75%) | 9 (25%) |
| | 27 (75%)/9 (25%) | 18 (67%) | 9 (100%) |
| 11271 | 48 | 44 (92%) | 4 (8%) |
| | 26 (54%)/22 (46%) | 23 (52%) | 3 (75%) |
| 11272 | 59 | 41 (69%) | 18 (31%) |
| | 37 (63%)/22 (27%) | 26 (63%) | 11 (61%) |
| 11312 | 1 | 1 (100%) | 0 (0%) |
| | 1 (100%)/0 (0%) | 1 (100%) | 0 (0%) |
| 11318 | 28 | 18 (64%) | 10 (36%) |
| | 10 (36%)/18 (64%) | 5 (28%) | 5 (50%) |

TABLE 2

| Chicken immunization regimes | | | | |
|---|---|---|---|---|
| Chicken ID | hGIPR-Fc protein | Plasmid DNA | Cells | Final Titer (to hGIPR-Fc) |
| 11270 | Boosts 1-5, 9 | Boosts 6-8 (mGIPR) | | 1:1.5e6 |
| 11271 | Boosts 1-5, 7, 9 | Boosts: 6, 8 (mGIPR) | | 1:1.5e6 |
| 11272 | Boosts 1-5 | | | 1:1.5e6 |
| 11312 | | Boosts 1-4, 6, 8 (hGIPR) | Boost 11 hGIPR | 1:12,500 |
| | | Boosts 5, 7, 9-10 (mGIPR) | CHO cells (3e7) | |
| 11318 | Boost 12 | Boosts 1-4, 6, 8 (hGIPR) | | 1:12,500 |
| | | Boosts 5, 7, 9-11 (mGIPR) | | |

41

TABLE 3

SPR affinity and cAMP activity of anti-GIPR reference
antibodies from rodent immunization and phage display

| Antibody | SPR KD [nM] hGIPR | cAMP IC50 [nM] hGIPR |
|---|---|---|
| Gipg013 [17] | 15 | 25 |
| Rodent_1 | 1.0 | 3 |
| Rodent_2 | 6.2 | 4.2 |
| Rodent_3 | 1.8 | 3.9 |
| Rodent_4 | 7.0 | 3.8 |

Materials & Methods

Figure 8:
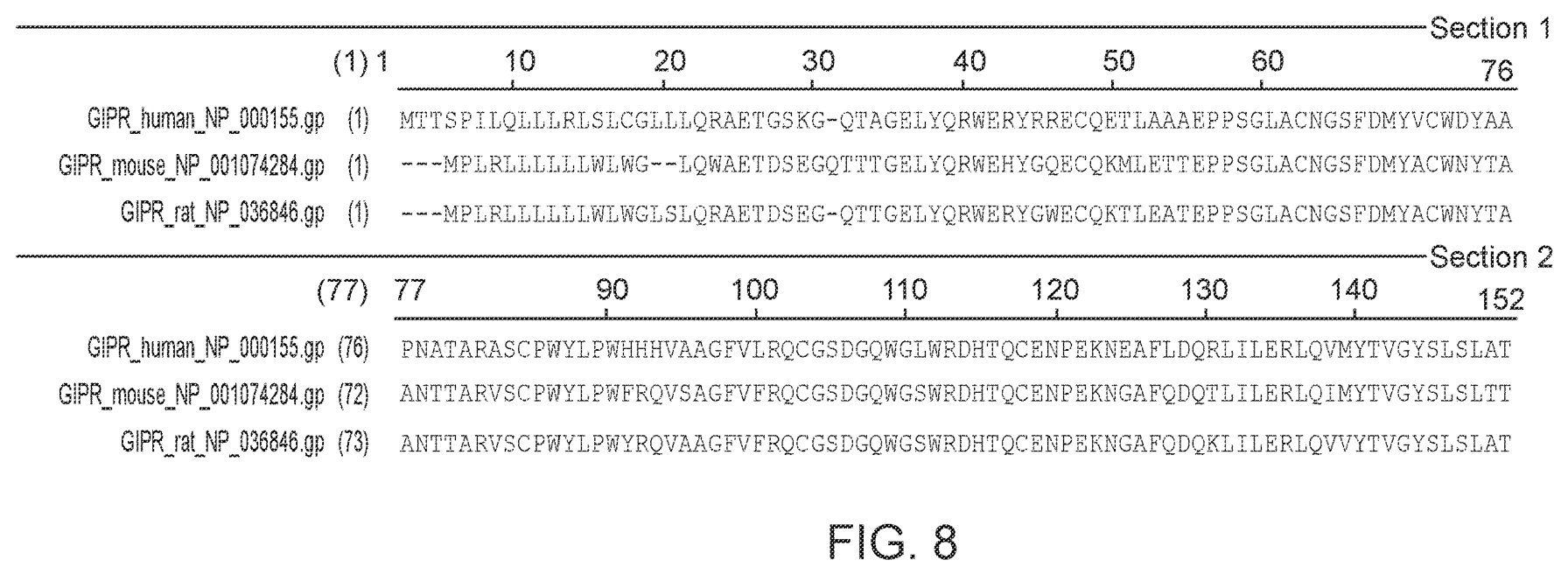

Antigen generation: Two types of GIPR-ECD fusion proteins were produced to use in this study. Human, mouse and rat-GIPR-ECD rabbit (rb) Fc fusion proteins were generated for biophysical assays, and human GIPR-ECD human Fc fusion protein (hGIPR-Fc) was used for immunization purposes. In both cases expression vectors based on pTT5 were constructed with sequences coding for the receptor extracellular domains fused to sequences for the Fc domains. Proteins were produced by transient expression in HEK293-E6 cells and purified by standard Protein A chromatography. In addition, the rb-Fc fusion proteins contained a Thrombin cleavage site between the ECD and Fc in order to facilitate removal of the Fc domain. Sequences are shown in FIG. 8.

Chicken Immunization: A total of five female white leghorn chickens were used for the program, all starting immunization at 8-9 weeks of age. Animals were immunized with hGIPR-Fc as purified protein, or full-length mouse or human GIPR cDNA, or with an alternating regimen of both DNA and protein (Table 2). Two animals were immunized with DNA and followed with a final boost either of CHO cells expressing human GIPR (chicken 11312), or hGIPR-Fc (chicken 11318). For the remaining animals, initial boosts with 200 μg protein were mixed with an equal volume of Imject Freund's complete adjuvant (VWR, PI77140) and administered intramuscularly. All subsequent boosts with 100 μg protein were mixed with an equal volume of Imject Freund's incomplete adjuvant (VWR, PI77145) and administered intramuscularly. DNA immunizations were performed in accordance with the Bio-Rad GeneGun protocol (Bio-Rad; Hercules, CA, USA). Briefly, gold particles were coated with 4 μg plasmid DNA encoding a CMV-based expression cassette containing either full-length human GIPR, or full length murine GIPR, and administered intradermally using the GeneGun at 400 PSI.

Once GIPR specific titer plateaued in the plasma, chickens were euthanized, spleens were removed and a single cell suspension prepared and cells were cryopreserved for single B cell cloning.

Polyclonal immune responses: Plasma was collected bi-weekly during the immunization to determine titer. High binding ELISA plates were coated with 2 μg/ml of hGIPR-Fc or purified Fc in PBS overnight at 4° C. Plates were blocked with 3% dry milk in PBS+0.05% Tween-20 (PBSM) for 1 hr at room temperature. Plates were washed with PBS+0.05% Tween-20 (PBST) and 50 ul of diluted plasma was added. Plasma was diluted with PBSM starting at 1:100 followed by seven, 5 fold dilutions down the ELISA plate. Plasma was incubated for 2 hours at room temperature then washed off with PBST. One hundred microliters of rabbit anti-chicken IgY HRP (Sigma, A9046) diluted 1:5000 with PBSM was added and incubated for 1 hour at room temperature. Plates were washed with PBST and developed with 50 ul of TMB and stopped with 50 ul 1N HCl. ELISA plates were read at 450 nm using the BioTek Synergy H1 Hybrid reader (Biotek; Vinooski, VT, USA).

Monoclonal Antibody Generation

Screening single B cells using the GEM assay: We used a single lymphocyte screening and recovery method, the Gel-Encapsulated Microenvironment (GEM) assay,[25, 43, 44] to isolate antigen-specific monoclonal antibodies from the GIPR immunized chickens. The GEM assay involves placing single antibody-secreting lymphocytes in proximity with reporters (which can be cells or beads). The secreted antibody diffuses locally within the GEM and has the opportunity to bind to the reporters. Bound antibody can be detected either directly through the use of a secondary antibody, or by eliciting a response in the reporter that generates a visual signal. Each GEM may contain multiple types of reporters that can be differentiated from each other based on color.

In this study, GEMs were prepared with both beads and cells. When beads were used, GIPR-Fc or Fc was coated onto white or blue beads, respectively. This approach allowed for the immediate elimination of any clones binding the Fc portion of the immunogen. CHO cells expressing GIPR were also used in the GEMs, with target specificity controlled for by the inclusion of parental CHO cells labeled with an alternative dye. Even though stable CHO lines were available expressing each of four species GIPR (human, cyno, rat, mouse), we generally opted for use of the CHO cell line expressing murine GIPR since we considered it more likely to identify pan-species cross reactive antibodies in an animal that was immunized with the human GIPR.

Expression and initial characterization of recombinant antibodies: Selected GEMs were isolated and antibody genes amplified through RT-PCR and cloned into the mammalian expression vector pF5a (Promega, C9401) in scFv-Fc format (with Fc derived from human IgG1 sequence). Plasmids containing recombinant scFv-Fc from the GEM harvests were transiently transfected into HEK 293 cells and clonal supernatants were harvested. Supernatants were tested for specificity and species cross-reactivity on parental CHO, human and murine GIPR expressing CHO cells using flow cytometry. All clones that bound both hGIPR and mGIPR CHO cells were sequenced (n=694), and unique clones (n=462) were re-transfected to generate material for further testing. Concentrations of the clones in the 2 ml supernatant were determined and binding to hGIPR-Fc confirmed in ELISA format. A more detailed flow cytometry analysis of species cross-reactivity was performed using parental, human, murine, rat and cyno GIPR expressing CHO cell. All clones were tested at a concentration of 5 ug/ml and compared to a positive control antibody.

FACS methodology: hGIPR, mGIPR and parental CHO cells were lifted from culture flasks using StemPro Accutase (Invitrogen, A1110501). Cells were counted and re-suspended at 2 million cells per milliliter in FACS buffer (PBS+1% BSA+0.1% NaN3) and 50 ul was put into each well of a 96 well U bottom plate. Supernatants were collected from 96 well transfections of HEK293 cells and spun down to remove debris. 50 ul of supernatant was added to each of the 3 cell lines, hGIPR mGIPR, and parental and incubated for 1 hour at 4° C. Cells were washed 2 times with FACS buffer and re-suspended in 100 ul of 5 ug/ml anti-human IgG Alexa 488 (Jackson Immunoresearch, 109-546-098). Cells were incubated for 45 min at 4° C. and washed 2 times with FACS buffer. Cells were re-suspended in 150 ul of FACS buffer and fluorescence data was gathered using the Attune acoustic focusing cytometer (Thermo Fisher Scientific; Waltham, MA, USA).

EC50 determination for binding strength to cellular hGIPR: Human GIPR and parental CHO cells were lifted from culture flasks using StemPro Accutase (Invitrogen, A1110501). Cells were counted and re-suspended at 2 million cells per milliliter in FACS buffer (PBS+1% BSA+ 0.1% NaN3) and 50 ul was put into each well of a 96 well U bottom plate. Supernatants were collected from 6 well transfections of HEK293 cells and spun down to remove debris. Antibodies diluted to 10 µg/ml followed by seven, three fold dilution was added to each of the cell lines, hGIPR and parental and incubated for 1 hour at 4° C. Cells were washed 2 times with FACS buffer and re-suspended in 100 µl of 5 µg/ml anti-human IgG Alexa 488 (Jackson Immunoresearch, 109-546-098). Cells were incubated for 45 min at 4° C. and washed 2 times with FACS buffer. Cells were re-suspended in 150 µl of FACS buffer and fluorescence data was gathered using the Attune acoustic focusing cytometer and the EC50 was determined using Prism v6 (Graphpad software). All antibodies were compared to a control antibody at the same concentrations.

Antibodies from previous immunization campaign: GIPR antibodies were also previously raised in classic rodent immunization and hybridoma campaigns (both rat and mouse immunizations). Animals were immunized using GIPR-ECD-Fc fusion protein, cell lines over-expressing GIPR or GIPR specific cDNA. Overall yields of antibodies binding to and antagonizing GIPR were low (JDK & RA, unpublished observations), prompting the switch to chicken immunization. For comparative purposes, screening data for a selection of rodent hybridoma supernatants is shown in FIG. 2A.

In the epitope clustering analysis shown in FIG. 5, a total of 5 anti GIPR recombinant antagonist antibodies were included to compare them to the chicken panel. 4 (Rodent_1-4) were generated at BI using hybridoma technology, Rodent_1 is derived from a mouse, whereas Rodent_2-4 are products of rat immunization. The antibody Gipg013 is the result of a phage display campaign described by Ravn et al.[17] SPR affinities and cAMP IC50 values for those recombinant antibodies are listed in Table 3. All recombinant antibodies comprise the V-regions fused to human IgG1 constant regions and were expressed by using the transient CHO-3E7 system[45] and purified by routine Protein A chromatography. The biophysical characteristics (SPR KD & IC50 in cAMP assay) of those recombinant anti-GIPR antibodies are listed in Table 3.

Biacore Methodology: All affinity measurements were performed and analyzed using a Biacore T200 (GE Healthcare; Chicago, IL, USA) employing a single cycle kinetics protocol. Briefly, test antibodies were captured on CM5 chips (GE Healthcare, BR100012) using the human (for Abs with human Fc) or mouse (for Abs with mouse or rat Fc) antibody capture kits (GE Healthcare, BR100838 & BR100839). Human, mouse or rat-GIPR-ECD (Thrombin cleaved from respective GIPR-ECD-rb-Fc antigen) were subsequently flown over the sensor surface at 5 different concentrations (0.125 µg/ml, 0.25 µg/ml, 0.5 µg/ml, 1 µg/ml and 2 µg/ml). The resulting curve was fitted in the Biacore T200 Evaluation software version 2.0 using a 1:1 fit in order to obtain KD values.

Functional GIPR cAMP assay: The antagonistic activity of antibodies was tested using the AlphaScreen Functional cAMP assay kit (Perkin-Elmer, 6760625R) according to the manufacturer's instructions. A CHO cell line over-expressing human GIPR was employed. Briefly, 10000 cells/50 µl/well were seeded in 384w plates and incubated for 24 h at 37° C. and 5% CO2. Then cells were transferred into 100 µl assay buffer supplemented with serial dilutions of the antibodies and kept for 15 mins at 26° C. Subsequently, 100 pM of the receptor agonist GIP were added with a further incubation step of 30 min at 26° C. In parallel, a cAMP standard curve was prepared according to the manufacturer's instructions. 10 µl of the lysis/detection buffer, anti-cAMP acceptor beads, streptavidin donor beads and biotinylated cAMP mixture were added to each well and incubated for 2 h at RT in the dark. A serial dilution of the GIPR agonist human GIP (Sigma, G2269) was used as a positive control. Plates were measured using an Envision reader (Perkin-Elmer; Waltham, MA, USA). CAMP concentrations were interpolated from the standard curves and obtained values were plotted against the antibody concentrations. Each sample was measured in duplicate. A curve (4 parametric logistic dose response model) was fitted to obtain IC50 values.

Epitope clustering analysis: Prior to epitope clustering, the human GIPR-ECD-rb-Fc fusion protein was biotinylated using the EZ-Link Sulfo NHS Biotin kit (Thermo Fisher Scientific, 21217) according to manufacturer's instructions. Measurements were performed using a Fortebio Octet HTX (Pall; Port Washington, NY, USA) high throughput biolayer interferometry system and streptavidin coated biosensors (Pall, 18-5020) on which the antigen was immobilized. Antibodies were binned in-tandem—sensors were incubated with the first antibody, followed by a baseline and incubation with the second antibody. An antibody not binding to the antigen was used as a control. Antibodies were diluted to 25 µg/ml in PBS prior to performing the assay. Biosensors were regenerated in 10 mM Glycine pH 3. The Octet Data Analysis software version 8 was used to process the data and create a matrix. The obtained nM shifts were normalized by dividing them by the value obtained using only the secondary antibody and multiplied by 100. The highest self-binding signal is used to judge the threshold for competition or additional binding. Primary antibodies are arranged in columns, secondary antibodies in columns. This data matrix was then analyzed using a method adapted from Liao-Chan et al.[21] Briefly, in Excel, the rows were sorted using the PEARSON function in a way that neighboring antibodies had the highest correlation coefficient. In addition, the unsorted matrix, with secondary antibody signals transposed into columns, were clustered using pvclust[22] in R version 6.1.3.[23] Prior to clustering, the matrix was normalized using the 'scale' function in R. In pvclust, clustering was performed using correlation as a distance measure and the Ward function as the clustering method. Specifically, the following command was used:

result←pvclust(scaled_data, method.hclust="ward.D2", method.dist="correlation", nboot=10000)

Sequence Analysis: VH sequences of the chicken derived antibodies were aligned using MegAlign (DNAStar; Madison, WI, USA) and the ClustalW method.[24] MegAlign was also used to construct the phylogenetic tree shown in FIG. 7.

Data visualization & statistical analyses: Figures were created and using Prism v6 (Graphpad Software Inc; La Jolla, CA, USA), as were statistical analyses. P value calculations were performed using the non-paired, non-parametric Mann-Whitney (2-group comparisons) and Kruskal-Wallis (multi-group comparisons) tests.

Discussion

GPCRs, owing to their instability outside of the membrane's lipid bilayer and typically small extracellular domains that can serve as antigens, are considered by many to be difficult targets for generating antibody therapeutics. We have successfully used chicken immunization to generate a highly diverse set of functional (antagonistic) antibodies against GIPR that cover a broad epitope space. The chicken hosts proved vastly superior in comparison to previously run classic rodent hybridoma campaigns from which we obtained a very small number of antagonistic antibodies.

Chickens readily produce antibodies that are cross reactive to mammalian orthologs. In the case of GIPR, chickens that were immunized and screened (in GEMs)[25] exclusively using human GIPR did indeed generate antibodies that were cross-reactive with murine GIPR, albeit at a relatively low frequency (~5%), which can be considered a "baseline" cross-reactivity rate for this particular target. Protocol adjustments were made that included immunizing with murine GIPR (DNA) as well as screening in GEMs with mGIPR-expressing cells, which combined to significantly enhance the hit rate for human/murine cross-reactive mAbs. It should be noted that while DNA immunization appeared to be useful in "pushing" the response towards species cross-reactivity, the two birds that were immunized exclusively with DNA until the final boost (chickens 11312 and 11318) did not achieve a final titer that was comparable to the other birds that received some protein boosts, and the antibodies recovered were of overall lower affinities. The alternating DNA/protein immunization strategy however was quite effective in producing a diverse panel of cross-reactive antibodies.

Mouse/human cross-reactive antibodies are not generally recovered from mice because they represent self-reactive specificities that are typically eliminated from the host animal, so it is somewhat surprising that the few murine and rat derived GIPR antibodies that were obtained did in fact cross-react to mGIPR. However, according to our epitope clustering investigations, all rodent derived antibodies are located within the same cluster (cluster "R"). One chicken-derived antibody was also found in this group. No rodent clones were identified to any of the other 4 non-overlapping epitope clusters that were defined by the panel of chicken antibodies. Many of the antibodies in each of these epitope clusters cross-react with GIPR from all four species tested (mouse, rat, cyno, human) and thus can be considered to define "pan-mammalian" epitopes. The absence of such specificities in the rodent panels is likely attributable to the influence of self-tolerance in the host animals. The strong sequence conservation among the rodent and human GIPR-ECD is a challenge in raising diverse sets of antibodies because the human antigen does not elicit a very strong immune response in either mouse or rat, and this limits the epitope space that can be covered by rodent immunization. Chicken immunization, on the other hand, has clearly enabled the generation of antibodies with much larger epitope diversity, which is likely driven by the chicken's lack of a GIPR ortholog. The ability of chicken immunization to expand the epitope repertoire for other antigens has also recently been described by Abdiche et al.[19]

It is not clear why such a high frequency of antagonistic antibodies were obtained through the chicken immunization performed in this study, since no special selection was used to enrich for biological activity. The cell-based GEM screen did bias towards antibodies that recognize native conformation GIPR and were also species cross-reactive, but a bioassay for activity was not used in the GEMs. All cAMP assays were performed after the mAbs were recovered. In the case of GIPR it may have been serendipitous that the selection strategy we used resulted in a mAb panel that was weighted towards receptor antagonism. While this may not be the case with a different receptor where epitopes associated with antagonism are more rare, it is reasonable to assume that the expanded epitope coverage that is generated through chicken immunization will be generally beneficial in the pursuit of biologically active antibodies to a variety of human targets.

Additional cysteines and disulfide bonds, a particular feature of chicken-derived antibodies utilized to stabilize long heavy chain CDR3 loops[20], may be considered liabilities for biopharmaceutical development. The immunogenic potential of these structures in humans is unknown at present and as such may pose a challenge for humanization. Replacing the cysteines via mutagenesis may have an unpredictable impact on the antibodies' affinity, binding mode or may even disrupt antigen recognition altogether. Further, additional cysteines can result in non-classical disulfide bond formation or result in increased proportions of free sulfhydryl groups, which may cause the emergence of difficult to control antibody subpopulations during manufacturing; hamper formulation development or promote antibody aggregation.[26-29] Selecting antibodies without these potential liabilities is therefore crucial to allow a smooth drug development process. While the majority (60%) of our anti-GIPR antibodies contained cysteines in the heavy chain CDR3, we found comparable fractions of antagonism among both cysteine-containing and cysteine-free antibodies. The median KDs for the cysteine-containing antibodies was lower than for the cysteine-free population, which may be a result of the longer CDR3 loops enabling optimal binding to the GIPR-ECD. Nevertheless, the overall lowest KD values were found among antibodies in the cysteine-free fraction and the presence of cysteines had no discernible impact on the observed IC50 in the functional GIPR cAMP assay. Additionally, each identified epitope cluster contained at least one cysteine-free antibody suggesting that the presence of longer CDR3s and disulfide-bonds is not an absolute necessity to obtain epitope diversity in chicken derived antibodies. We conclude that screening a sufficiently high number of antibodies raised in chicken enables the selection of cysteine-free antibodies with desired functional profiles if this feature is desirable for a particular antibody development project. Furthermore, recent advances in the development of a genetically engineered chicken that produces human sequence antibodies may provide a viable alternative to take advantage of chicken host immune recognition without introducing potential sequence liabilities.[30-32]

Our epitope clustering experiments revealed several interesting points. Cluster assignment obtained from the biolayer interferometry studies was well supported by the antibody sequence data, in particular the heavy chain CDR3 sequence. Our finding that chicken-derived antibodies containing similar or identical heavy chain CDR3 sequences fall in the same BLI clusters and therefore recognize the same epitope underlines that this part of the antibody structure, which possesses the highest sequence diversity, serves as the key determinant for specificity and selectivity.[33] Notably, we also saw a relationship between functional antagonism and epitope cluster. The four non-antagonistic antibodies clustered together, revealing that there are specific functional (allowing antibody mediated antagonism when bound) and non-functional epitopes on the GIPR-ECD. However, two functional, i.e. antagonistic, antibodies also fell within this cluster. Both share a unique HC-CDR3 sequence distinct from the non-functional antibodies in the cluster. This suggests that the detailed structure of the antibody paratope, i.e.

the overall combined architecture of CDRs and frameworks, has an impact on antagonistic functionality when bound to a particular epitope of the GIPR-ECD. Detailed investigations into the antibody-receptor protein-protein interactions will be required to elucidate the underlying principles of this behavior.

Finally, the epitope clustering results appeared to be asymmetrical for several antibodies, meaning that whether or not an antibody pair competes for the binding of the GIPR-ECD is dependent on which antibody was used first. Such asymmetries in epitope binning analyses have been reported in a number of studies in the literature, across different types of epitope mapping methodologies.[21, 34-38] Liao Chan et al[21] have attributed these observations to the possibility that the first epitope-paratope interaction blocks the second one due to steric, allosteric or electrostatic effects. Because of subtle differences in antibody sequences and antigen binding modes, the inverse sequential binding of the same antibody pair may present a different binning result. In the context of our antigen, the class B GPCR GIPR, it is conceivable that an antibody binding the ECD induces conformational changes—in the same manner that the endogenous ligand GIP rearranges the secondary structure of the ECD upon binding the receptor.[9, 39-42] Such a subtle structural change may either enable or prevent the binding of a second antibody and help explain the observed clustering asymmetry.

In conclusion, we recommend considering using chickens as alternative hosts in antibody generation campaigns, particularly when aiming to access difficult antigenic targets, such as GPCRs, where high levels of rodent-human sequence conservation may limit the antibody yield from classic mouse or rat hybridoma approaches. In our specific case, which aimed at raising functionally antagonist antibodies against the human GIP receptor, chicken immunization resulted in a much larger number of antibodies overall, a higher fraction of antagonistic antibodies and greater epitope diversity than rodent hybridoma technology.

REFERENCES

1. Baggio L L, Drucker D J. Biology of incretins: GLP-1 and GIP. Gastroenterology 2007; 132:2131-57.
2. McIntosh C H S, Widenmaier S, Kim S-J. Glucose-dependent insulinotropic polypeptide (Gastric Inhibitory Polypeptide; GIP). Vitamins and hormones 2009; 80:409-71.
3. Christensen M, Vedtofte L, Holst J J, Vilsbøll T, Knop F K. Glucose-dependent insulinotropic polypeptide: a bifunctional glucose-dependent regulator of glucagon and insulin secretion in humans. Diabetes 2011; 60:3103-9.
4. Irwin N, Gault V, Flatt P R. Therapeutic potential of the original incretin hormone glucose-dependent insulinotropic polypeptide: diabetes, obesity, osteoporosis and Alzheimer's disease? Expert Opin Investig Drugs 2010; 19:1039-48.
5. Flatt P R. Dorothy Hodgkin Lecture 2008. Gastric inhibitory polypeptide (GIP) revisited: a new therapeutic target for obesity-diabetes? Diabet Med 2008; 25:759-64.
6. Meier J J, Nauck M A, Schmidt W E, Gallwitz B. Gastric inhibitory polypeptide: the neglected incretin revisited. Regul Pept 2002; 107:1-13.
7. Nauck M A, Baller B, Meier J J. Gastric inhibitory polypeptide and glucagon-like peptide-1 in the pathogenesis of type 2 diabetes. Diabetes 2004; 53 Suppl 3: S190-6.
8. Usdin T B, Mezey E, Button D C, Brownstein M J, Bonner T I. Gastric inhibitory polypeptide receptor, a member of the secretin-vasoactive intestinal peptide receptor family, is widely distributed in peripheral organs and the brain. Endocrinology 1993; 133:2861-70.
9. Cordomí A, Ismail S, Matsoukas M-T, Escrieut C, Gherardi M-J, Pardo L, et al. Functional elements of the gastric inhibitory polypeptide receptor: Comparison between secretin- and rhodopsin-like G protein-coupled receptors. Biochem Pharmacol 2015; 96:237-46.
10. Miller L J, Dong M, Harikumar K G, Gao F. Structural basis of natural ligand binding and activation of the Class II G-protein-coupled secretin receptor. Biochem Soc Trans 2007; 35:709-12.
11. Hollenstein K, de Graaf C, Bortolato A, Wang M-W, Marshall F H, Stevens R C. Insights into the structure of class B GPCRs. Trends Pharmacol Sci 2014; 35:12-22.
12. Miyawaki K, Yamada Y, Ban N, Ihara Y, Tsukiyama K, Zhou H, et al. Inhibition of gastric inhibitory polypeptide signaling prevents obesity. Nat Med 2002; 8:738-42.
13. Yamada C, Yamada Y, Tsukiyama K, Yamada K, Yamane S, Harada N, et al. Genetic inactivation of GIP signaling reverses aging-associated insulin resistance through body composition changes. Biochem Biophys Res Commun 2007; 364:175-80.
14. Pathak V, Gault V A, Flatt P R, Irwin N. Antagonism of gastric inhibitory polypeptide (GIP) by palmitoylation of GIP analogues with N- and C-terminal modifications improves obesity and metabolic control in high fat fed mice. Mol Cell Endocrinol 2015; 401:120-9.
15. Gault V A, McClean P L, Cassidy R S, Irwin N, Flatt P R. Chemical gastric inhibitory polypeptide receptor antagonism protects against obesity, insulin resistance, glucose intolerance and associated disturbances in mice fed high-fat and cafeteria diets. Diabetologia 2007; 50:1752-62.
16. McClean P L, Irwin N, Cassidy R S, Holst J J, Gault V A, Flatt P R. GIP receptor antagonism reverses obesity, insulin resistance, and associated metabolic disturbances induced in mice by prolonged consumption of high-fat diet. Am J Physiol Endocrinol Metab 2007; 293: E1746-55.
17. Ravn P, Madhurantakam C, Kunze S, Matthews E, Priest C, O'Brien S, et al. Structural and pharmacological characterization of novel potent and selective monoclonal antibody antagonists of glucose-dependent insulinotropic polypeptide receptor. J Biol Chem 2013; 288:19760-72.
18. Hutchings C J, Koglin M, Marshall F H. Therapeutic antibodies directed at G protein-coupled receptors. mAbs 2010; 2:594-606.
19. Abdiche Y N, Harriman R, Deng X, Yeung Y A, Miles A, Morishige W, et al. Assessing kinetic and epitopic diversity across orthogonal monoclonal antibody generation platforms. mAbs 2016; 8:264-77.
20. Wu L, Oficjalska K, Lambert M, Fennell B J, Darmanin-Sheehan A, Shúilleabháin D N, et al. Fundamental Characteristics of the Immunoglobulin V H Repertoire of Chickens in Comparison with Those of Humans, Mice, and Camelids. J Immunol 2012; 188:322-33.
21. Liao-Chan S, Zachwieja J, Gomez S, Duey D, Lippincott J, Theunissen J-W. Monoclonal antibody binding-site diversity assessment with a cell-based clustering assay. J Immunol Methods 2014; 405:1-14.
22. Suzuki R, Shimodaira H. Pvclust: an R package for assessing the uncertainty in hierarchical clustering. Bioinformatics 2006; 22:1540-2.

23. Team R C. R: A language and environment for statistical computing. R Foundation for Statistical Computing. Vienna, Austria, 2015.

24. Larkin M A, Blackshields G, Brown N P, Chenna R, McGettigan P A, McWilliam H, et al. Clustal W and Clustal X version 2.0. Bioinformatics 2007; 23:2947-8.

25. Mettler Izquierdo S, Varela S, Park M, Collarini E J, Lu D, Pramanick S, et al. High-efficiency antibody discovery achieved with multiplexed microscopy. Microscopy (Oxford, England) 2016; 65:341-52.

26. Liu H, May K. Disulfide bond structures of IgG molecules. mAbs 2012; 4:17-23.

27. Liu H, Chumsae C, Gaza-Bulseco G, Hurkmans K, Radziejewski C H. Ranking the susceptibility of disulfide bonds in human IgG1 antibodies by reduction, differential alkylation, and LC-MS analysis. Anal Chem 2010; 82:5219-26.

28. Brych S R, Gokarn Y R, Hultgen H, Stevenson R J, Rajan R, Matsumura M. Characterization of antibody aggregation: role of buried, unpaired cysteines in particle formation. J Pharm Sci 2010; 99:764-81.

29. Hutterer K M, Hong R W, Lull J, Zhao X, Wang T, Pei R, et al. Monoclonal antibody disulfide reduction during manufacturing: Untangling process effects from product effects. mAbs 2013; 5:608-13.

30. Schusser B, Collarini E J, Yi H, Izquierdo S M, Fesler J, Pedersen D, et al. Immunoglobulin knockout chickens via efficient homologous recombination in primordial germ cells. Proc Natl Acad Sci USA 2013; 110:20170-5.

31. Leighton P A, Schusser B, Yi H, Glanville J, Harriman W. A Diverse Repertoire of Human Immunoglobulin Variable Genes in a Chicken B Cell Line is Generated by Both Gene Conversion and Somatic Hypermutation. Front Immunol 2015; 6.

32. Schusser B, Yi H, Collarini E J, Izquierdo S M, Harriman W D, Etches R J, et al. Harnessing gene conversion in chicken B cells to create a human antibody sequence repertoire. PLoS ONE 2013; 8: e80108.

33. Xu J L, Davis M M. Diversity in the CDR3 region of V(H) is sufficient for most antibody specificities. Immunity 2000; 13:37-45.

34. Abdiche Y N, Miles A, Eckman J, Foletti D, Van Blarcom T J, Yeung Y A, et al. High-throughput epitope binning assays on label-free array-based biosensors can yield exquisite epitope discrimination that facilitates the selection of monoclonal antibodies with functional activity. PLoS ONE 2014; 9: e92451.

35. Abdiche Y N, Malashock D S, Pinkerton A, Pons J. Exploring blocking assays using Octet, ProteOn, and Biacore biosensors. Anal Biochem 2009; 386:172-80.

36. Abdiche Y N, Lindquist K C, Stone D M, Rajpal A, Pons J. Label-free epitope binning assays of monoclonal antibodies enable the identification of antigen heterogeneity. J Immunol Methods 2012; 382:101-16.

37. Nagata S, Numata Y, Onda M, Ise T, Hahn Y, Lee B, et al. Rapid grouping of monoclonal antibodies based on their topographical epitopes by a label-free competitive immunoassay. J Immunol Methods 2004; 292:141-55.

38. Miller P L, Wolfert R L, Diedrich G. Epitope binning of murine monoclonal antibodies by a multiplexed pairing assay. J Immunol Methods 2011; 365:118-25.

39. Venneti K C, Malthouse J P G, O'Harte F P M, Hewage C M. Conformational, receptor interaction and alanine scan studies of glucose-dependent insulinotropic polypeptide. Biochim Biophys Acta 2011; 1814:882-8.

40. Underwood C R, Parthier C, Reedtz-Runge S. Structural basis for ligand recognition of incretin receptors. Vitamins and hormones 2010; 84:251-78.

41. Tikhele S H, Pissurlenkar R R S, Srivastava S, Saran A, Coutinho E C. Mapping interactions of gastric inhibitory polypeptide with GIPR N-terminus using NMR and molecular dynamics simulations. J Pept Sci 2010; 16:383-91.

42. Pal K, Melcher K, Xu H E. Structure and mechanism for recognition of peptide hormones by Class B G-protein-coupled receptors. Acta Pharmacol Sin 2012; 33:300-11.

43. Harriman W D. Gel microdrop composition and method of using the same. Crystal Bioscience Inc., 2013.

44. Harriman W D. Gel microdrop composition and method of using the same. Crystal Bioscience Inc., 2011.

45. Durocher Y, Loignon M. Process, Vectors and Engineered Cell Lines for Enhanced Large-Scale Transfection. 2009.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An antibody that binds to the human glucose-dependent insulinotropic polypeptide (GIP) receptor, wherein the antibody comprises:
    a variable domain comprising:
        i. heavy chain CDR1, CDR2 and CDR3 regions that are identical to the heavy chain CDR1, CDR2 and CDR3 regions of an antibody selected from FIG. 9; and
        ii. light chain CDR1, CDR2 and CDR3 regions that are identical to the light chain CDR1, CDR2 and CDR3 regions of the antibody, selected from FIG. 10.

2. The antibody of claim 1, wherein the antibody comprises:
    a heavy chain variable domain comprising an amino acid sequence that is at least 90% identical to the amino acid sequence of any of SEQ ID NOS: 35-74; and
    a light chain variable domain comprising an amino acid sequence that is at least 90% identical to the amino acid sequence of any of SEQ ID NOS: 75-114.

3. The antibody of claim 1, wherein the antibody inhibits GIP receptor signaling.

4. The antibody of claim 1, wherein the heavy chain variable domain and the light chain variable domain are present in separate polypeptides.

5. The antibody of claim 1, wherein the heavy chain variable domain and the light chain variable domain are present in a single polypeptide.

6. The antibody of claim 1, wherein the antibody binds the human GIP receptor with an affinity in the range of $10^7$ M$^{-1}$ to $10^{12}$ M$^{-1}$.

7. The antibody of claim 1, wherein the antibody comprises a covalently linked non-peptide synthetic polymer.

8. The antibody of claim 7, wherein the synthetic polymer is poly (ethylene glycol) polymer.

9. The antibody of claim 1, wherein the antibody comprises a covalently linked lipid or fatty acid moiety.

10. The antibody of claim 1, wherein the antibody comprises a covalently linked polysaccharide or carbohydrate moiety.

11. The antibody of claim 1, wherein the antibody is a single-chain Fv (scFv) antibody.

12. The antibody of claim 10, wherein the scFv is multimerized.

13. A pharmaceutical composition comprising:

a) the antibody of claim 1; and b) a pharmaceutically acceptable carrier.

14. The pharmaceutical composition of claim 13, wherein the antibody is encapsulated in a liposome.

15. A method for inhibiting GIP receptor signaling, comprising contacting a cell comprising a GIP receptor with an antibody of claim 1.

16. A method of inhibiting the GIP receptor in a subject, comprising administering to the subject an effective amount of the antibody of claim 1.

\* \* \* \* \*